United States Patent
Sherman et al.

(10) Patent No.: US 7,131,953 B2
(45) Date of Patent: *Nov. 7, 2006

(54) CPR ASSIST DEVICE ADAPTED FOR ANTERIOR/POSTERIOR COMPRESSIONS

(75) Inventors: Darren R. Sherman, Sunnyvale, CA (US); Kenneth H. Mollenauer, Saratoga, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 344 days.

This patent is subject to a terminal disclaimer.

(21) Appl. No.: 10/750,937

(22) Filed: Dec. 31, 2003

(65) Prior Publication Data

US 2004/0225238 A1    Nov. 11, 2004

Related U.S. Application Data

(63) Continuation of application No. 10/427,645, filed on Apr. 30, 2003, now Pat. No. 6,939,315, which is a continuation of application No. 09/866,377, filed on May 25, 2001, now Pat. No. 6,616,620.

(51) Int. Cl.
*A61H 31/00* (2006.01)

(52) U.S. Cl. .......................................... 601/41; 601/44
(58) Field of Classification Search .............. 601/41, 601/44, 89, 93, 97, 104–107, 134, 135, 143, 601/144, 148

See application file for complete search history.

(56) References Cited

U.S. PATENT DOCUMENTS

| | | | |
|---|---|---|---|
| 651,962 A | 6/1900 | Boghean ...................... 501/41 |
| 2,071,215 A | 2/1937 | Petersen | |
| 2,486,667 A * | 11/1949 | Meister ........................ 601/41 |
| 2,699,163 A | 1/1955 | Engstrom | |
| 2,754,817 A | 7/1956 | Nemeth | |
| 2,853,998 A | 9/1958 | Emerson | |
| 2,899,955 A | 8/1959 | Huxley, III et al. | |
| 3,042,024 A | 7/1962 | Mendelson | |
| 3,120,228 A | 2/1964 | Huxley, III | |
| 3,368,550 A | 2/1968 | Glascock | |
| 3,461,860 A | 8/1969 | Barkalow et al. | |
| 3,481,327 A | 12/1969 | Drennen | |
| 3,777,744 A | 12/1973 | Fryfogle | |
| 3,782,371 A | 1/1974 | Dorouineau ................. 128/28 |
| 4,004,579 A | 1/1977 | Dedo ............................ 128/28 |
| 4,338,924 A | 7/1982 | Bloom ......................... 128/28 |
| 4,349,015 A | 9/1982 | Alferness ..................... 128/28 |
| 4,397,306 A | 8/1983 | Weisfeldt et al. ............ 128/28 |
| 4,570,615 A | 2/1986 | Barkalow ..................... 128/28 |
| 4,664,098 A | 5/1987 | Woudenberg et al. ........ 128/53 |
| 4,770,164 A | 9/1988 | Lach et al. ................... 128/28 |
| 4,915,095 A | 4/1990 | Chun ........................... 128/28 |
| 4,928,674 A | 5/1990 | Halperin et al. ........... 128/30.2 |
| 5,056,505 A | 10/1991 | Warwick et al. .......... 128/30.2 |
| 5,098,369 A | 3/1992 | Heilman et al. ............. 600/16 |
| 5,184,606 A | 2/1993 | Csorba ........................ 128/28 |

(Continued)

FOREIGN PATENT DOCUMENTS

WO    WO 97/22327    6/1997

(Continued)

*Primary Examiner*—Danton DeMille
(74) *Attorney, Agent, or Firm*—K. David Crockett; Crockett & Crockett

(57) ABSTRACT

A resuscitation device for automatic compression of a victim's chest using a compression belt operably attached to a platform upon which a patient rests. In use, the compression belt is wrapped around the patient and at least one spindle operably attached to the platform.

7 Claims, 44 Drawing Sheets

U.S. PATENT DOCUMENTS

| | | | |
|---|---|---|---|
| 5,217,010 A | 6/1993 | Tsitlik et al. | 128/419 PG |
| 5,222,478 A | 6/1993 | Scarberry et al. | 128/30.2 |
| 5,257,619 A | 11/1993 | Everete | 128/28 |
| 5,277,194 A | 1/1994 | Hosterman et al. | 128/721 |
| 5,287,846 A | 2/1994 | Capjon et al. | 128/28 |
| 5,295,481 A | 3/1994 | Geeham | 601/43 |
| 5,327,887 A | 7/1994 | Nowakowski | 128/204.21 |
| 5,359,999 A | 11/1994 | Kinsman | 128/204.21 |
| 5,370,603 A | 12/1994 | Newman | 601/41 |
| 5,372,487 A | 12/1994 | Pekar | 417/480 |
| 5,399,148 A | 3/1995 | Waide et al. | 601/41 |
| 5,405,362 A | 4/1995 | Kramer | 607/5 |
| 5,474,533 A | 12/1995 | Ward et al. | 604/26 |
| 5,490,820 A | 2/1996 | Schock et al. | 601/41 |
| 5,520,622 A * | 5/1996 | Bastyr et al. | 602/16 |
| 5,630,789 A | 5/1997 | Schock et al. | 601/41 |
| 5,664,563 A | 9/1997 | Schroeder et al. | 128/204.25 |
| 5,738,637 A | 4/1998 | Kelly et al. | 601/41 |
| 5,769,800 A | 6/1998 | Gelfand et al. | 601/151 |
| 6,066,106 A * | 5/2000 | Sherman et al. | 601/41 |

FOREIGN PATENT DOCUMENTS

WO      WO 9909929 A1 * 3/1999

* cited by examiner

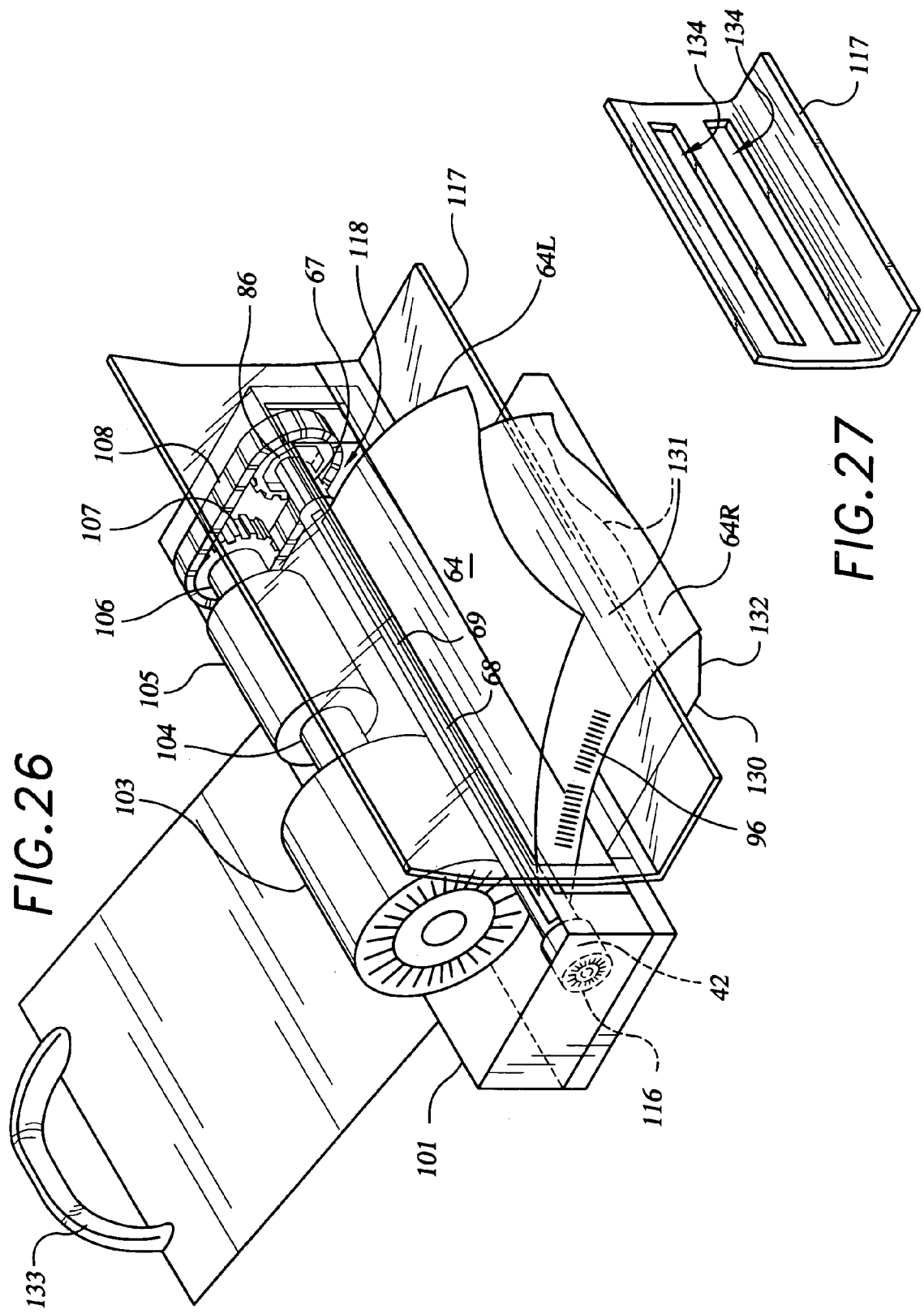

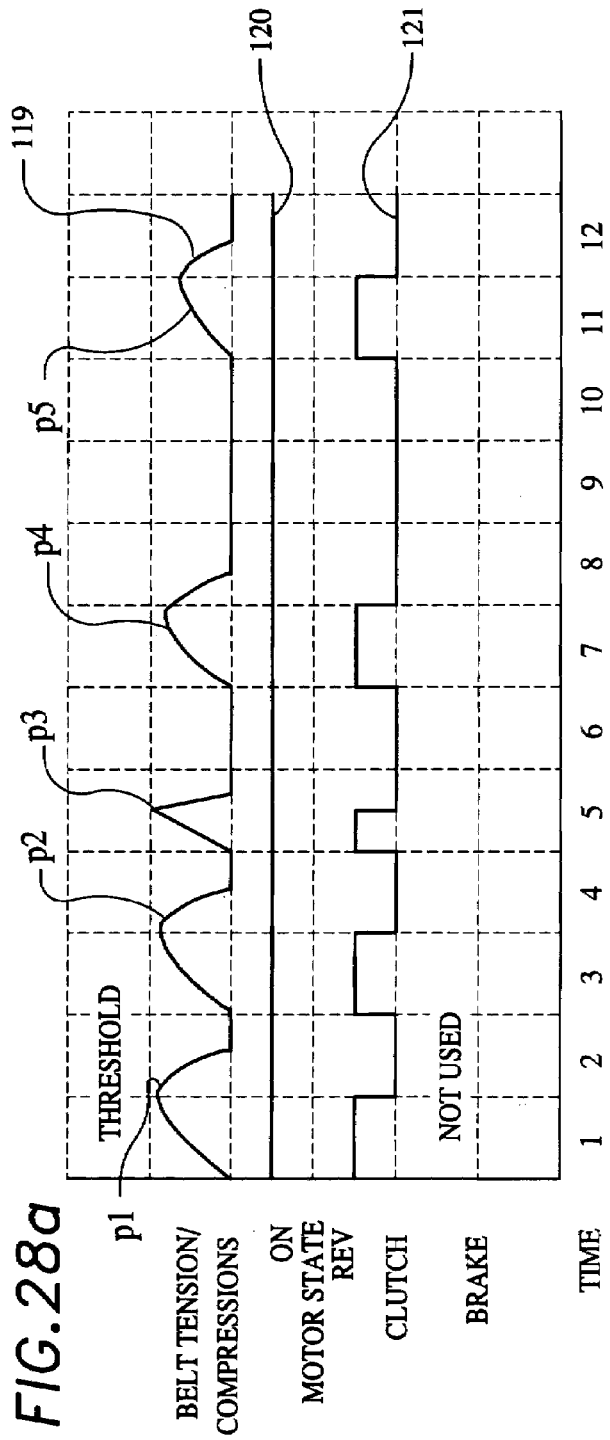

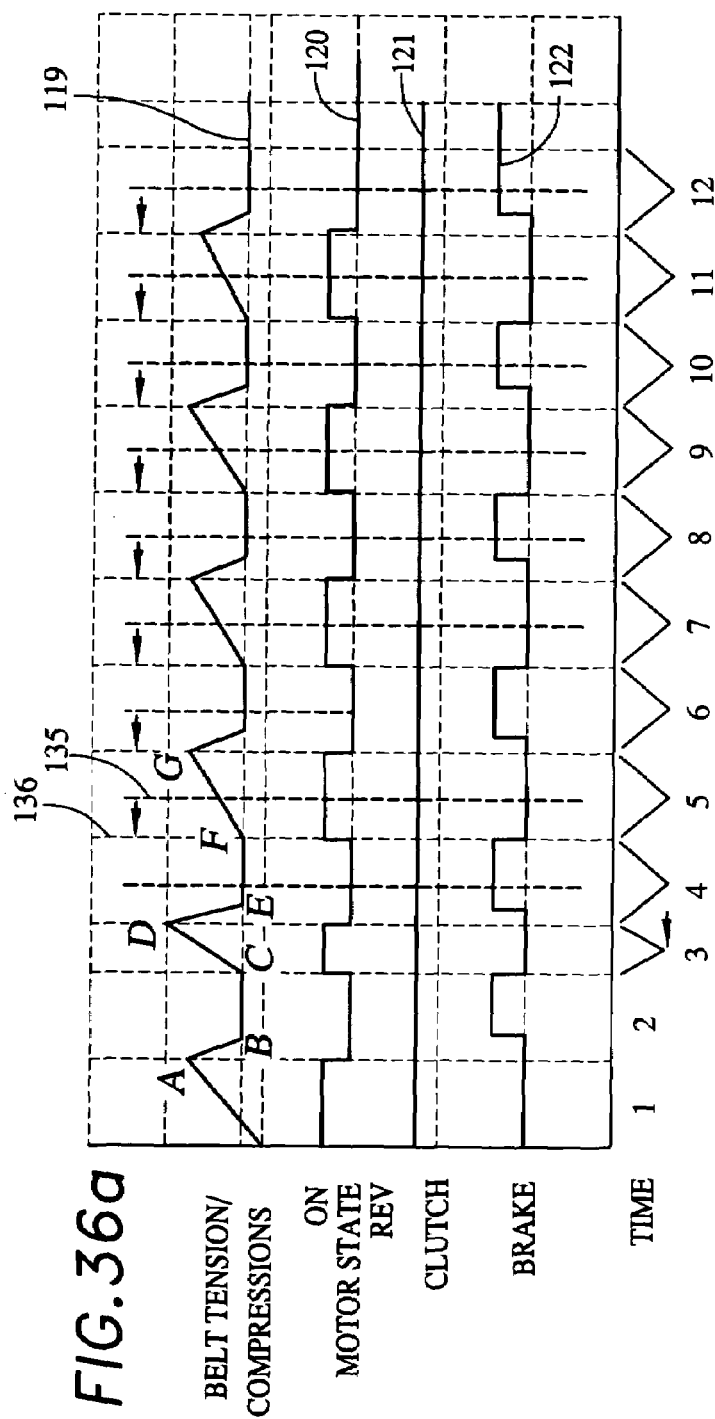

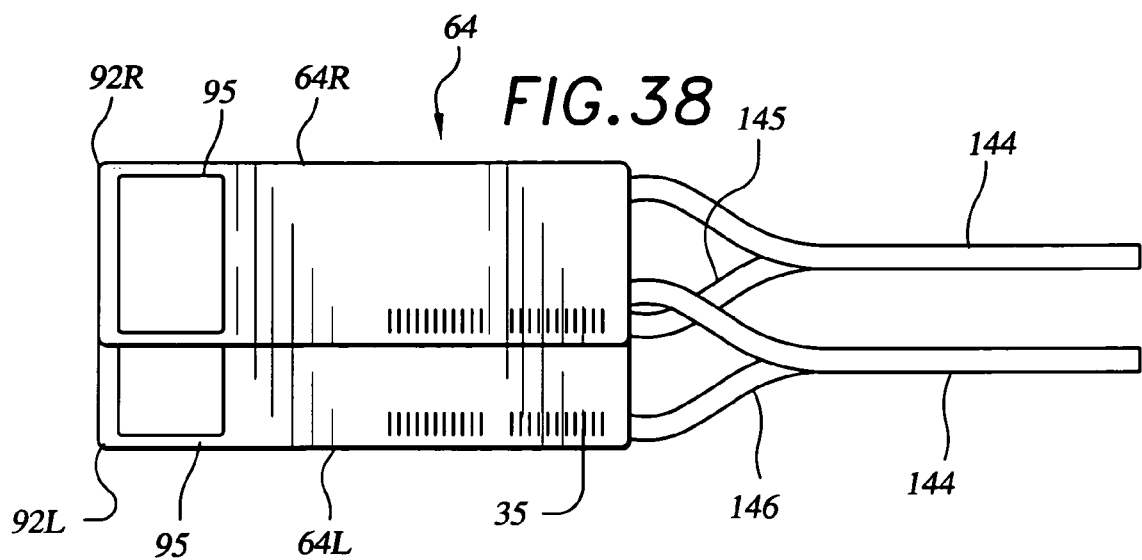
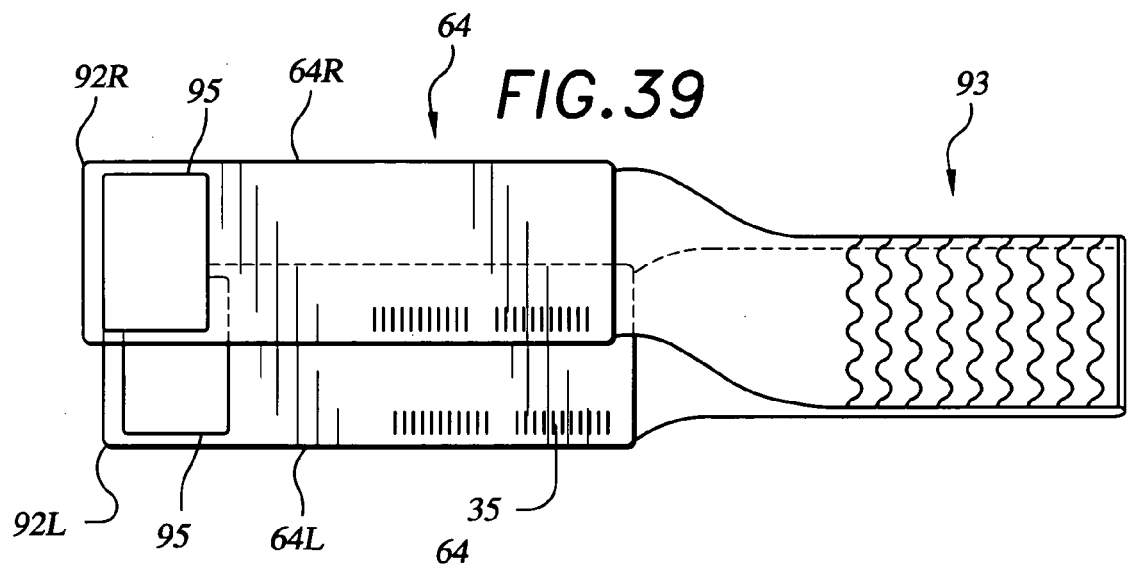
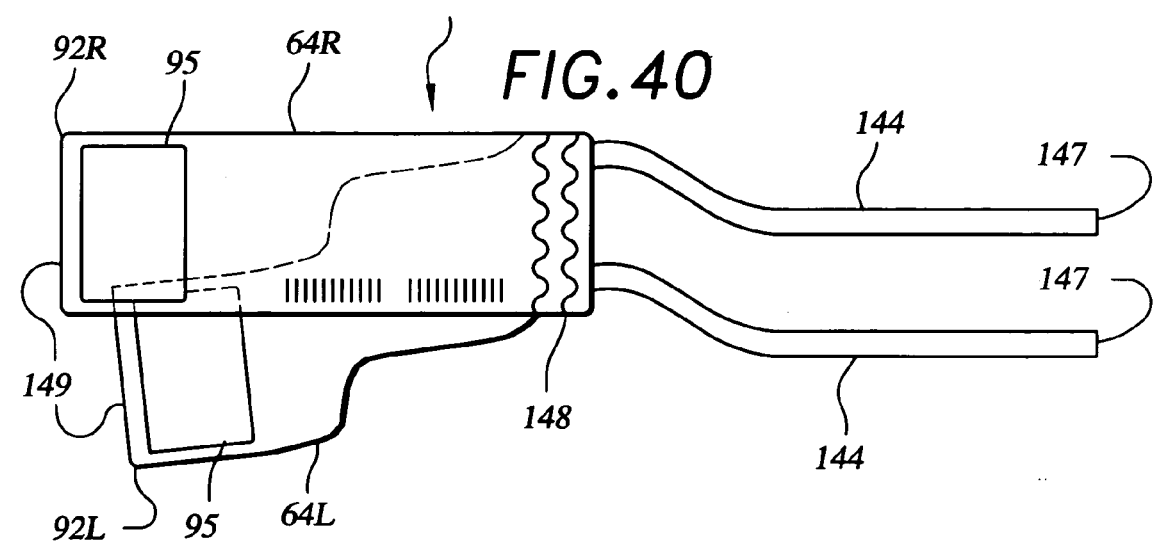

CPR ASSIST DEVICE ADAPTED FOR ANTERIOR/POSTERIOR COMPRESSIONS

This application is a continuation of U.S. application Ser. No. 10/427,645, filed Apr. 30, 2003, now U.S. Pat. No. 6,939,315 which is a continuation of U.S. application Ser. No. 09/866,377, filed May 25, 2001, now U.S. Pat. No. 6,616,620.

FIELD OF THE INVENTIONS

This invention relates to emergency medical devices and methods and the resuscitation of cardiac arrest patients.

BACKGROUND OF THE INVENTIONS

Cardiopulmonary resuscitation (CPR) is a well known and valuable method of first aid. CPR is used to resuscitate people who have suffered from cardiac arrest after heart attack, electric shock, chest injury and many other causes. During cardiac arrest, the heart stops pumping blood, and a person suffering cardiac arrest will soon suffer brain damage from lack of blood supply to the brain. Thus, CPR requires repetitive chest compression to squeeze the heart and the thoracic cavity to pump blood through the body. Very often, the patient is not breathing, and mouth to mouth artificial respiration or a bag valve mask is used to supply air to the lungs while the chest compression pumps blood through the body.

It has been widely noted that CPR and chest compression can save cardiac arrest patients, especially when applied immediately after cardiac arrest. Chest compression requires that the person providing chest compression repetitively push down on the sternum of the patient at 80 to 100 compressions per minute. CPR and closed chest compression can be used anywhere, wherever the cardiac arrest patient is stricken. In the field, away from the hospital, it may be accomplished by ill-trained bystanders or highly trained paramedics and ambulance personnel.

When a first aid provider performs chest compression effectively, blood flow in the body is typically about 25 to 30% of normal blood flow. This is enough blood flow to prevent brain damage. However, when chest compression is required for long periods of time, it is difficult if not impossible to maintain adequate compression of the heart and rib cage. Even experienced paramedics cannot maintain adequate chest compression for more than a few minutes. Hightower, et al., Decay In Quality Of Chest Compressions Over Time, 26 Ann. Emerg. Med. 300 (September 1995). Thus, long periods of CPR, when required, are not often successful at sustaining or reviving the patient. At the same time, it appears that, if chest compression could be adequately maintained, cardiac arrest victims could be sustained for extended periods of time. Occasional reports of extended CPR efforts (45 to 90 minutes) have been reported, with the victims eventually being saved by coronary bypass surgery. See Tovar, et al., Successful Myocardial Revascularization and Neurologic Recovery, 22 Texas Heart J. 271 (1995).

In efforts to provide better blood flow and increase the effectiveness of bystander resuscitation efforts, modifications of the basic CPR procedure have been proposed and used. Of primary concern in relation to the devices and methods set forth below are the various mechanical devices proposed for use in main operative activity of CPR, namely repetitive compression of the thoracic cavity.

The device shown in Barkolow, Cardiopulmonary Resuscitator Massager Pad, U.S. Pat. 4,570,615 (Feb. 18, 1986), the commercially available Thumper device, and other such devices, provide continuous automatic closed chest compression. Barkolow and others provide a piston which is placed over the chest cavity and supported by an arrangement of beams. The piston is placed over the sternum of a patient and set to repeatedly push downward on the chest under pneumatic power. The patient must first be installed into the device, and the height and stroke length of the piston must be adjusted for the patient before use, leading to delay in chest compression. Other analogous devices provide for hand operated piston action on the sternum. Everette, External Cardiac Compression Device, U.S. Pat. No. 5,257,619 (Nov. 2, 1993), for example, provides a simple chest pad mounted on a pivoting arm supported over a patient, which can be used to compress the chest by pushing down on the pivoting arm. These devices are not clinically more successful than manual chest compression. See Taylor, et al., External Cardiac Compression, A Randomized Comparison of Mechanical and Manual Techniques, 240 JAMA 644 (August 1978).

Other devices for mechanical compression of the chest provide a compressing piston which is secured in place over the sternum via vests or straps around the chest. Woudenberg, Cardiopulmonary Resuscitator, U.S. Pat. No. 4,664,098 (May 12, 1987) shows such a device which is powered with an air cylinder. Waide, et al., External Cardiac Massage Device, U.S. Pat. No. 5,399,148 (Mar. 21, 1995) shows another such device which is manually operated. In another variation of such devices, a vest or belt designed for placement around the chest is provided with pneumatic bladders which are filled to exert compressive forces on the chest. Scarberry, Apparatus for Application of Pressure to a Human Body, U.S. Pat. No. 5,222,478 (Jun. 29, 1993), and Halperin, Cardiopulmonary Resuscitation and Assisted Circulation System, U.S. Pat. No. 4,928,674 (May 29, 1990), show examples of such devices. Lach, et al., Resuscitation Method and Apparatus, U.S. Pat. No. 4,770,164 (Sep. 13, 1988), proposed compression of the chest with wide band and chocks on either side of the back, applying a side-to-side clasping action on the chest to compress the chest.

Several operating parameters are required for a successful resuscitation device. Chest compression must be accomplished vigorously if it is to be effective because very little of the effort exerted in chest compression actually compresses the heart and large arteries of the thorax and most of the effort goes into deforming the chest and rib cage. The force needed to provide effective chest compression, however, creates risk of other injuries. It is well known that placement of the hands over the sternum is required to avoid puncture of the heart during CPR. See Jones and Fletter, Complications After Cardiopulmonary Resuscitation, 12 Am. J. Emerg. Med. 687 (November 1994), which indicates that lacerations of the heart, coronary arteries, aortic aneurysm and rupture, fractured ribs, lung herniation, stomach and liver lacerations have been caused by CPR. Thus the risk of injury attendant to chest compression is high, and clearly may reduce the chances of survival of the patient vis-à-vis a resuscitation technique that could avoid those injuries. Further, chest compression will be completely ineffective for very large or obese cardiac arrest patients because the chest cannot be compressed enough to cause blood flow. Additionally, chest compression via pneumatic devices is hampered in its application to females due to the lack of provision for protecting the breasts from injury and applying compressive force to deformation of the thoracic cavity rather than the breasts.

CPR and chest compression should be initiated as quickly as possible after cardiac arrest to maximize its effectiveness and avoid neurologic damage due to lack of blood flow to the brain. Hypoxia sets in about two minutes after cardiac arrest, and brain damage is likely after about four minutes without blood flow to the brain. Further, the severity of neurologic defect increases rapidly with time. A delay of two or three minutes significantly decreases the chance of survival and increases the probability and severity of brain damage. However, CPR and ACLS are unlikely to be provided within this time frame. Response to cardiac arrest is generally considered to occur in four phases, including action by Bystander CPR, Basic Life Support, Advanced Cardiac Life Support, and the Emergency Room. Bystander CPR occurs, if at all, within the first few minutes after cardiac arrest. Basic Life Support is provided by First Responders who arrive on scene about 4 to 6 minutes after being dispatched to the scene. First responders include ambulance personnel, emergency medical technicians, firemen and police. They are generally capable of providing CPR but cannot provide drugs or intravascular access, defibrillation or intubation. Advanced Life Support is provided by paramedics or nurse practitioners who generally follow the first responders and arrive about 8 to 15 minutes after dispatch. ALS is provided by paramedics, nurse practitioners or emergency medical doctors who are generally capable of providing CPR, and drug therapy, including intravenous drug delivery, defibrillation and intubation. The ALS providers may work with a patient for twenty to thirty minutes on scene before transporting the patient to a nearby hospital. Though defibrillation and drug therapy are often successful in reviving and sustaining the patient, CPR is often ineffective even when performed by well trained first responders and ACLS personnel because chest compression becomes ineffective as the providers become fatigued. Thus, the initiation of CPR before arrival of first responders is critical to successful life support. Moreover, the assistance of a mechanical chest compression device during the Basic Life Support and Advanced Life Support stages is needed to maintain the effectiveness of CPR.

SUMMARY

The devices described below provide for circumferential chest compression using a device which is compact, portable or transportable, self-powered with a small power source, and easy to use by bystanders with little or no training. Additional features may also be provided in the device to take advantage of the power source and the structural support board contemplated for a commercial embodiment of the device.

The device includes a broad belt which wraps around the chest and is buckled in the front of the cardiac arrest patient. The belt is repeatedly tightened around the chest to cause the chest compression necessary for CPR. The buckles and/or front portion of the belt are anatomically accommodating for the female breast, or for the obese person, so that the device is effective for women as well as men. The buckle may include an interlock which must be activated by proper attachment before the device will activate, thus preventing futile belt cycles. The operating mechanism for repeatedly tightening the belt is provided in a support board or in a small box locatable at the patient's side, and comprises a rolling mechanism which takes up the intermediate length of the belt to cause constriction around the chest. The roller is powered by a small electric motor, and the motor is powered by batteries and/or standard electrical power supplies such as 120V household electrical sockets or 12V DC automobile power sockets (car cigarette lighter sockets). The belt is contained in a cartridge which is easily attached and detached from the motor box. The cartridge itself may be folded for compactness. The motor is connected to the belt through a transmission that includes a cam brake and a clutch, and is provided with a controller which operates the motor, clutch and cam brake in several modes. One such mode provides for limiting belt travel according to a high compression threshold, and limiting belt travel to a low compression threshold. Another such mode includes holding the belt taut against relaxation after tightening the belt, and thereafter releasing the belt. Respiration pauses, during which no compression takes place to permit CPR respiration, can be included in the several modes. In other embodiments, the motor is connected to the belt through a transmission that includes a non-reversing coupling, permitting simplified operation of the system, and brakes are connected to the system through take-offs from the drive train. Thus, numerous inventions are incorporated into the portable resuscitation device described below.

The portable resuscitation device may incorporate a number of features and accessories that aid in the administration of CPR and other therapy. Bystanders may be unable to confidently determine if chest compression is needed, or when it should be stopped. Accordingly, the device may be combined with an interlock system including a heart monitor or EKG which diagnoses the condition of the patient, and circuitry or a computer which initiates, permits or forbids belt operation accordingly. The power supply provided for belt constriction may also be used to provide power for defibrillation (an appropriate treatment for many cardiac arrests). Again, bystanders will most likely not be capable of determining when defibrillation is appropriate, and the defibrillation portion of the device may be provided with an interlock system including the heart monitor or EKG which diagnoses the condition of the patient and circuitry which initiates, permits, or forbids defibrillation. Expert systems implemented through the circuitry or computer modules can accomplish these functions.

Automatic, computer driven therapy of this nature may provide early and appropriate life saving response to many cardiac arrest patients who would otherwise die. However, some situations in which the device might be used call for expert supervision of the CPR process by emergency medical technicians, emergency room doctors, or cardiologists. To this end, the expert systems mentioned above may be replaced with the expert diagnosis and decision-making of medical personnel through a telemetry system housed within the support board of the device. The support board can include a telemetry system which automatically dials medical personnel in a nearby hospital, emergency medical crew, ambulance, or even a central diagnostic and control facility. Interlocks, limit switches and other typical sensors can be used to sense the proper position and closure of the belt about the chest of the patient. Heart monitors and EKG electrodes can sense the heart rate and EKG of the victim. Using communication equipment within the device, this information can be communicated from the device to medical personnel remote from the victim. Through the same system, the medical personnel can communicate with the device to initiate, permit or prohibit belt constriction or defibrillation, as dictated by preferred medical procedures. Communication can be established through normal telephone lines and a cordless telephone, or through a cellular telephone system, paging system, internet or any other communications system. The device can be programmed with location information, or provided with GPS capabilities to determine the location of the device, and this information can be automatically transmitted to an emergency response system such as the 911 system when the system is placed in use.

BRIEF DESCRIPTION OF THE DRAWINGS

FIG. 26 illustrates the configuration of the motor and clutch within the motor box.

FIG. 27 shows a shield which is interposed between the motor box and the patient.

FIG. 28 is a table of the motor and clutch timing in a basic embodiment.

FIG. 28a is a diagram of the pressure changes developed by the system operated according to the timing diagram of FIG. 28.

FIG. 36 is table of the motor and clutch timing for operation of the compression belt in an embodiment in which the system timing is reset each time an upper threshold is achieved.

FIG. 36a is a diagram of the pressure changes developed by the system operated according to the timing diagram of FIG. 36.

FIG. 38 illustrates an alternative embodiment of the chest compression belt with single layer pull straps connecting the belt to the drive spool.

FIG. 39 illustrates an embodiment of the chest compression belt with non-torquing spooling segment connecting the belt to the drive spool.

FIG. 40 illustrates an embodiment of the chest compression belt with single layer pull straps connecting the belt to the drive spool.

DETAILED DESCRIPTION OF THE INVENTIONS

Figure 1:
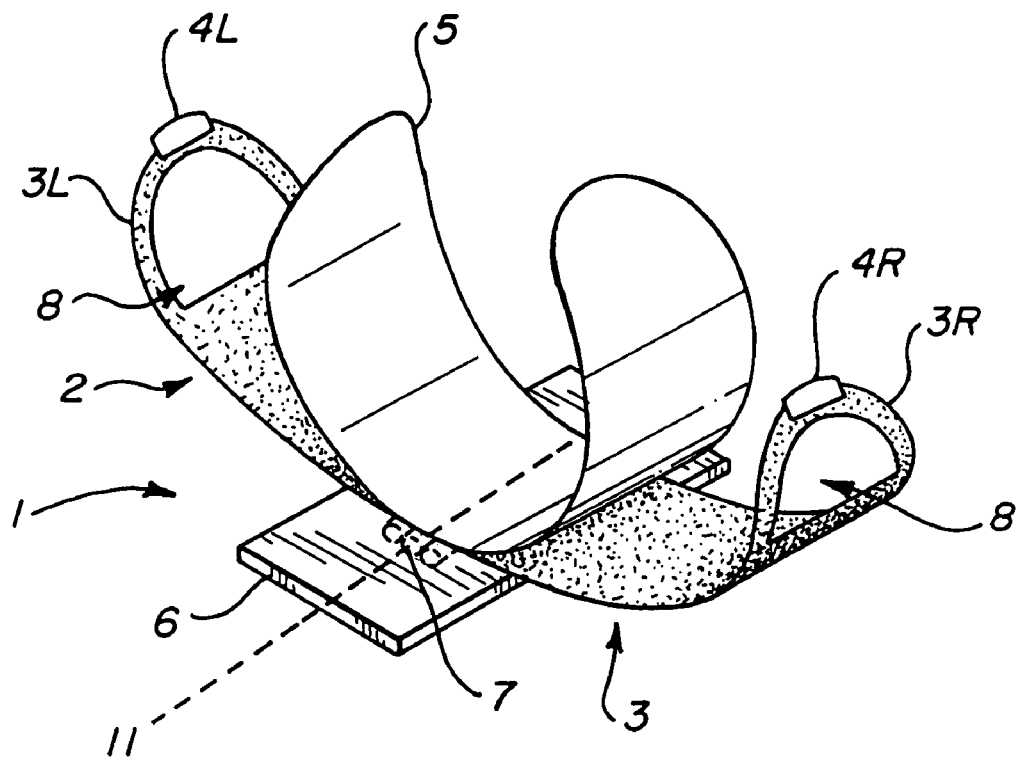
FIG. 1 is an overview of the resuscitation device, showing the inner and outer vests partially open.

FIG. 1 shows a simplified version of the resuscitation device 1. The mechanisms used for compressing the chest includes compression assembly 2 which includes a chest compression belt 3 with buckles 4L and 4R, a friction liner 5, a support board 6 and a motor driven spool assembly 7. The support board 6 is placed under a cardiac arrest victim, and the compression belt 3 and friction liner 5 are wrapped around the victim's chest. The chest compression belt, having a left side 3L and a right side 3R, is buckled over the victim's chest by latching the buckles 4L and 4R together. In this configuration, the friction liner 5 will fit between the chest compression belt 3 and the victim and any clothes worn by the victim. The compression belt may be made of any strong material, and sail cloth has proven adequate for use. The compression belt may also be referred to as a vest, corset, girdle, strap or band. The friction liner may be made of Teflon®, Tyvek® or any other low friction material (by low friction, we mean a material that will permit sliding of the compression belt with less friction than expected between the belt and the victims clothing or bare skin). The friction liner may be made with any suitable lining material, as its purpose is to protect the victim from rubbing injury caused by the compression belt, and it may also serve to limit frictional forces impeding the compression belt operation. The friction liner can be provided in the form of a belt, vest, corset, girdle, strap or band, and may partially or completely encircle the chest.

Figure 2:
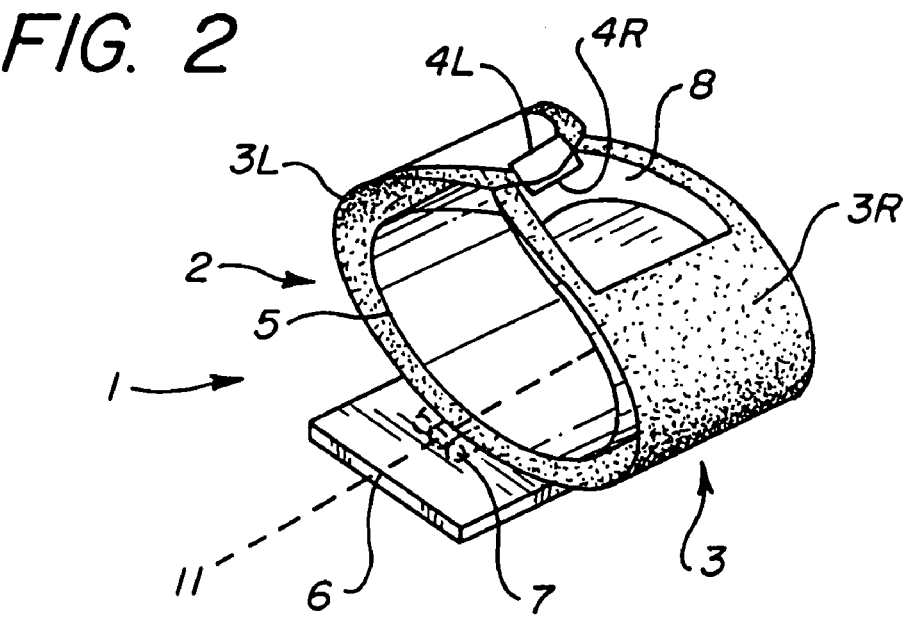
FIG. 2 is an overview of the resuscitation device in the buckled configuration.
Figure 3:
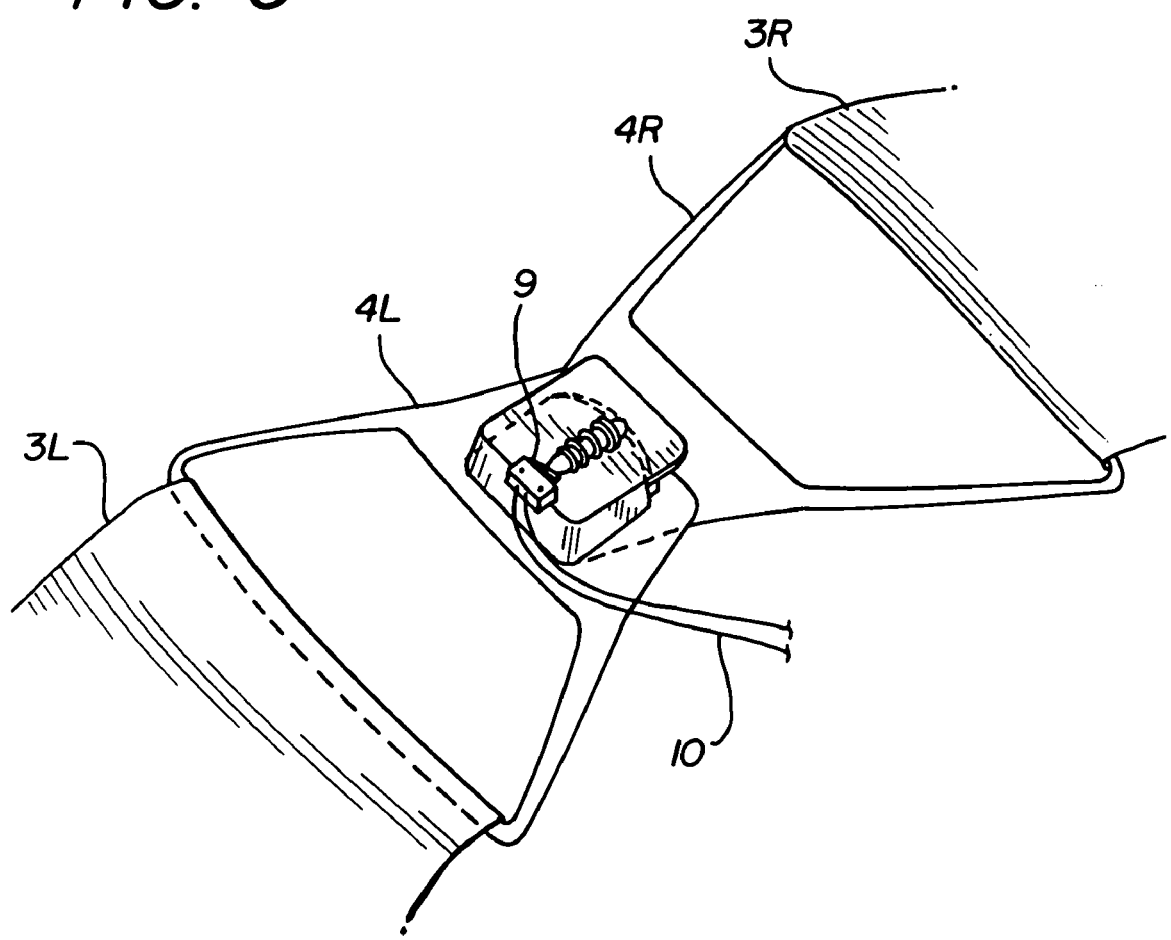
FIG. 3 is a detail view of the buckle used to close the device about a victim.
Figure 13A:
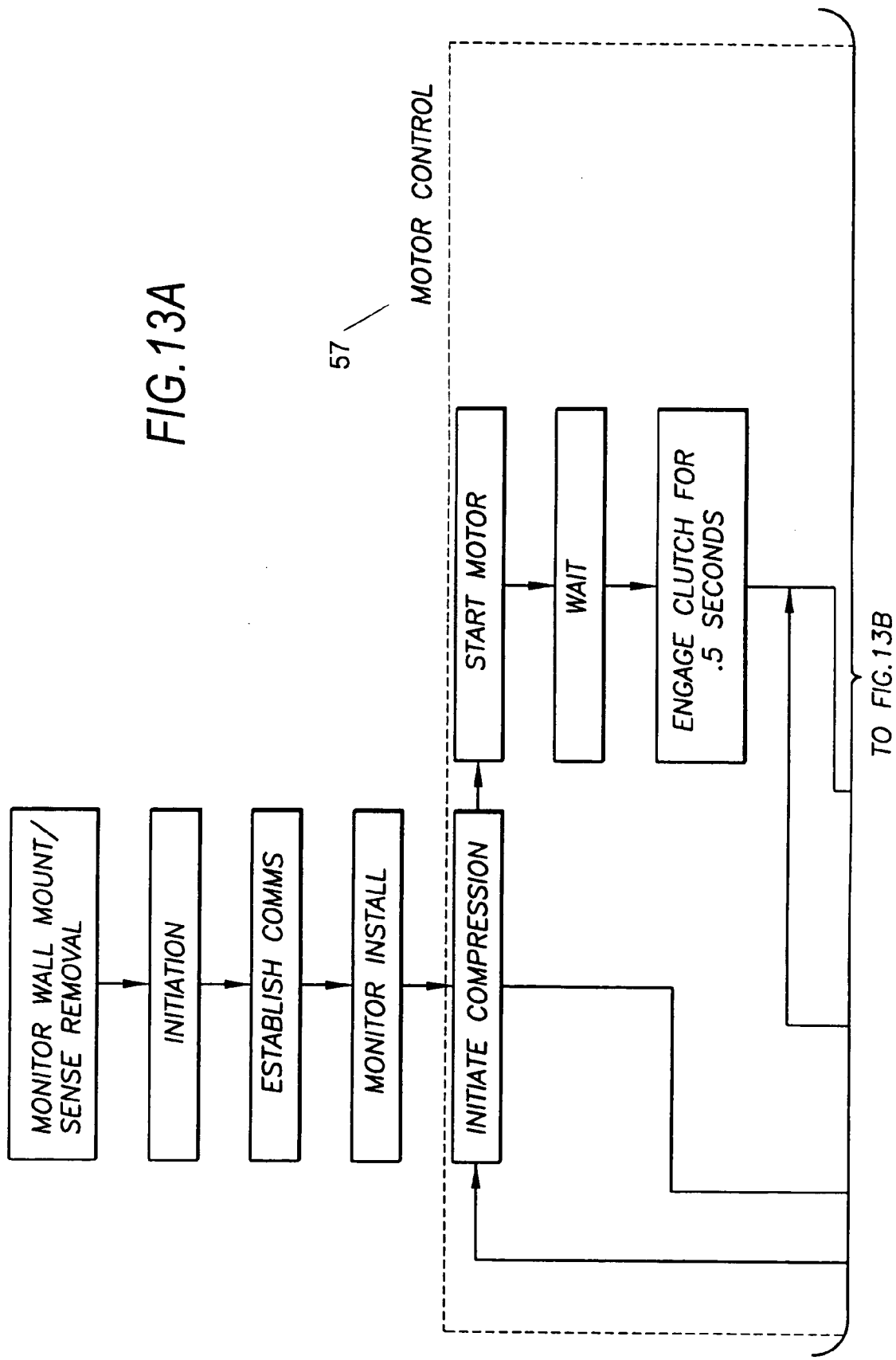
FIG. 13 is a block diagram of the motor control system.
Figure 13B:
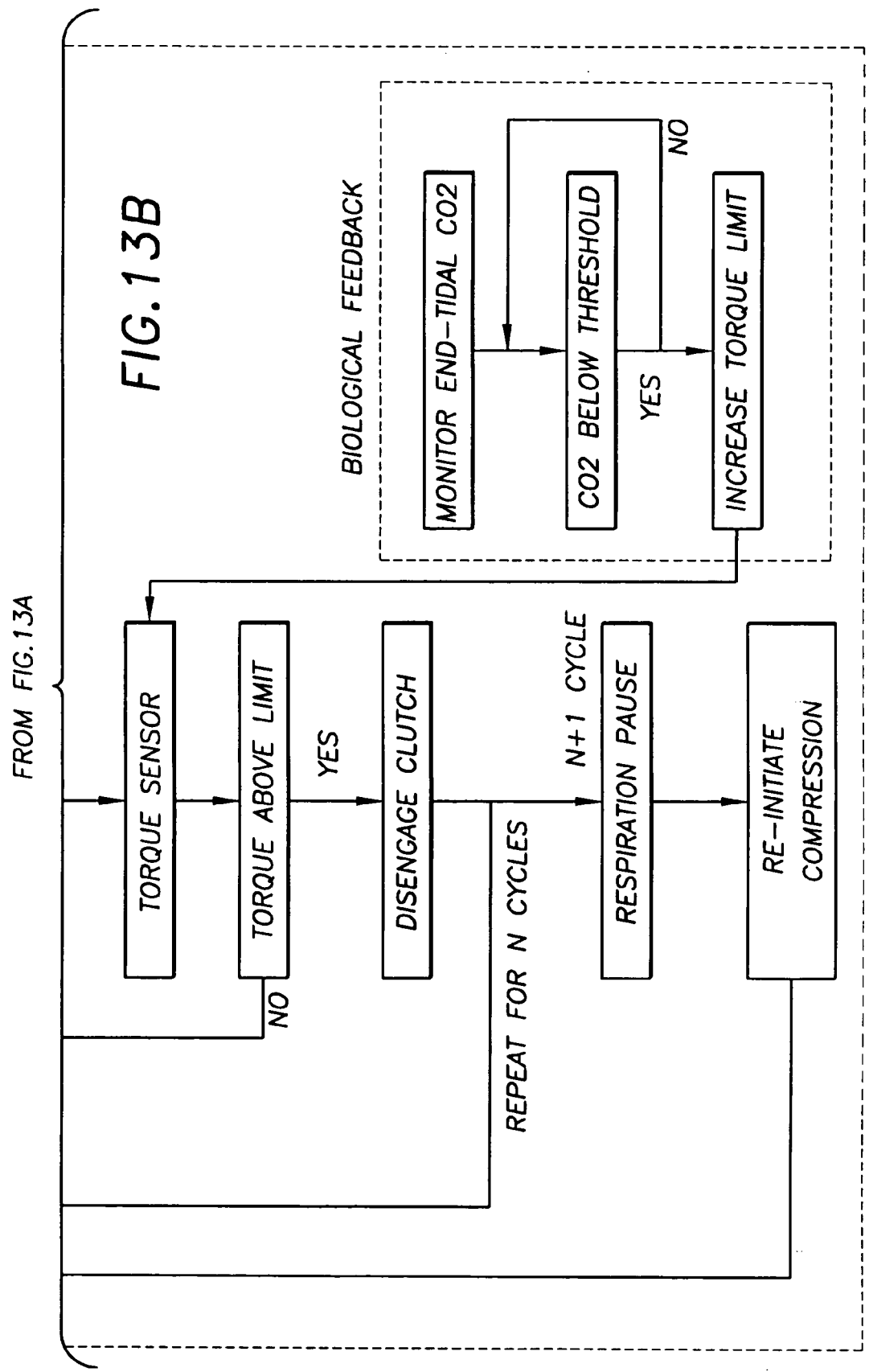

The front of the compression belt 3, including the buckles 4L and 4R, are configured to provide a broad pressure point over the sternum of the victim. This is illustrated in FIG. 2. Large openings 8 may be provided to accommodate female breasts and obese male breasts. The underside of the buckles 4L and 4R are smooth and broad, to distribute compressive force evenly over a wide area of the chest corresponding to the sternum. The point at which the buckle attaches to the chest compression belt may vary considerably, from the front of the chest to the back of the compression assembly, and the openings 8 may be provided in the buckles rather than the belt itself. FIG. 3 shows a detail of the buckles 4 used to fasten the compression belt about the chest of the victim. The buckle may be of any type, and preferably includes a latch sensing switch 9 operably connected through wire 10 to the motor control system (see FIG. 13) to indicate that the device has been buckled about the victims chest and is ready for the initiation of compression cycles. The buckles shown in FIG. 3 are D-ring shaped buckles with large openings 8, attached to the compression belt 3. Other fasteners and fastening means may be used.

Figure 4:
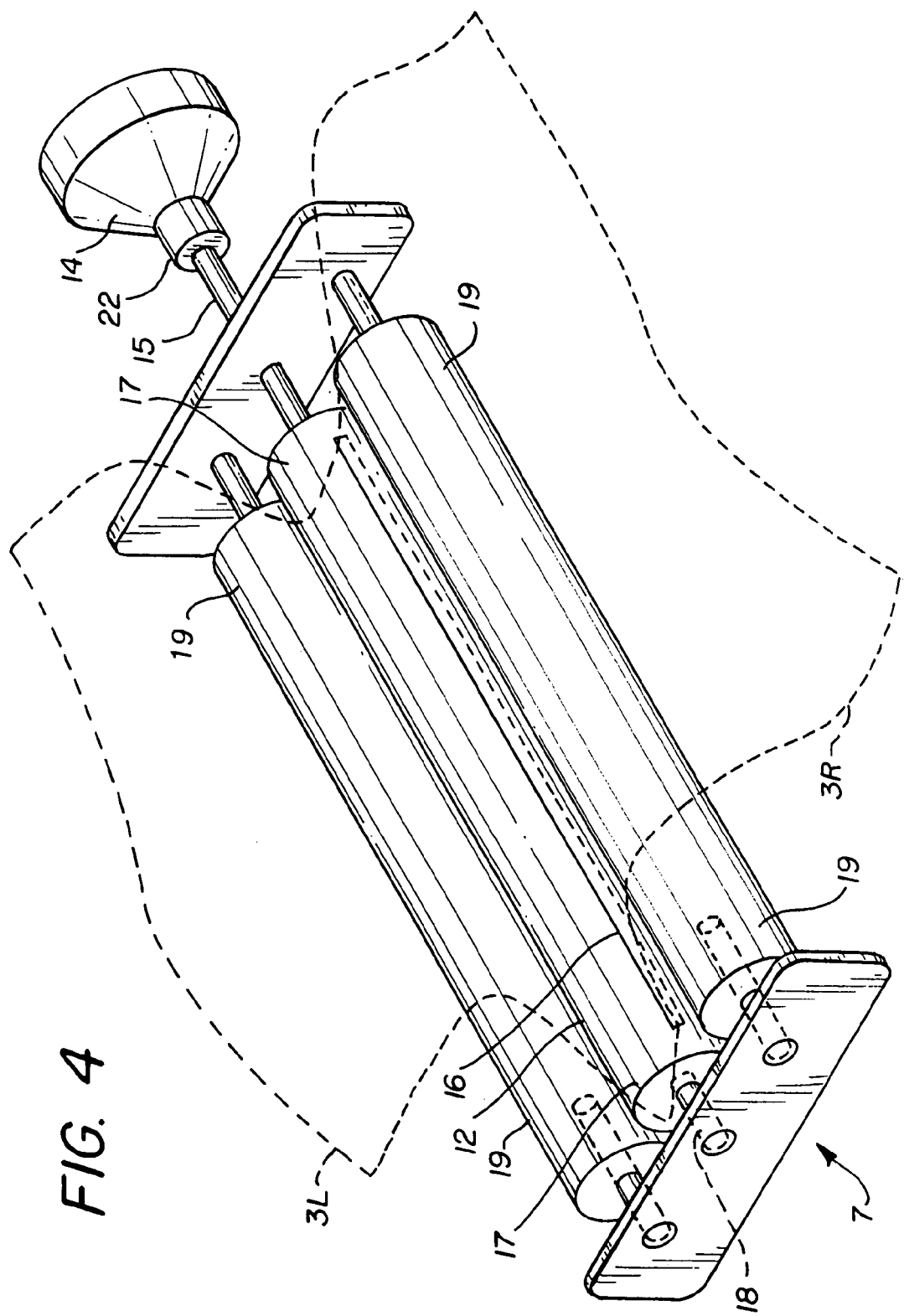
FIG. 4 shows the spool assembly used to operate the compression belt.

The chest compression belt 3 is repeatedly tightened about the chest of a victim through the action of one or more tightening spools which make up the spool assembly 7 located within the support board 6. The spool assembly, illustrated in FIG. 4, includes at least one spool or reel connected to the compression belt 3 at the back of the belt, preferably near the center or saggital line 11 (See FIGS. 1 and 2) of the compression belt (although it may be located on the front or side of compression belt). FIG. 4 shows a view of the spool assembly 7 and its attachment to the compression belt 3. A spool assembly includes a single drive spool 12 operably connected to the motor 14 through drive shaft 15. The compression belt is secured to the drive spool shaft in any suitable manner. In this case a longitudinal slot 16 is provided in the drive spool 12. The slot extends radially or chordally through the drive spool and extends axially for a length corresponding to the width of the compression belt, leaving the ends 17 of the drive spool solid for connection to the drive shaft 15 and journal shaft 18. The belt is slipped through the slot to create a secure connection between the belt and the drive spool. When secured in this manner, the rotation of the drive spool 12 will take up the right side of the compression belt 3R and the left side of the compression belt 3L and roll them up onto the spool, thus tightening the compression belt about the chest of the victim wearing the device. Spindles or alignment rollers 19 provide for alignment and low friction feed of the belt onto the roll created by operation of the drive shaft.

Figure 5:
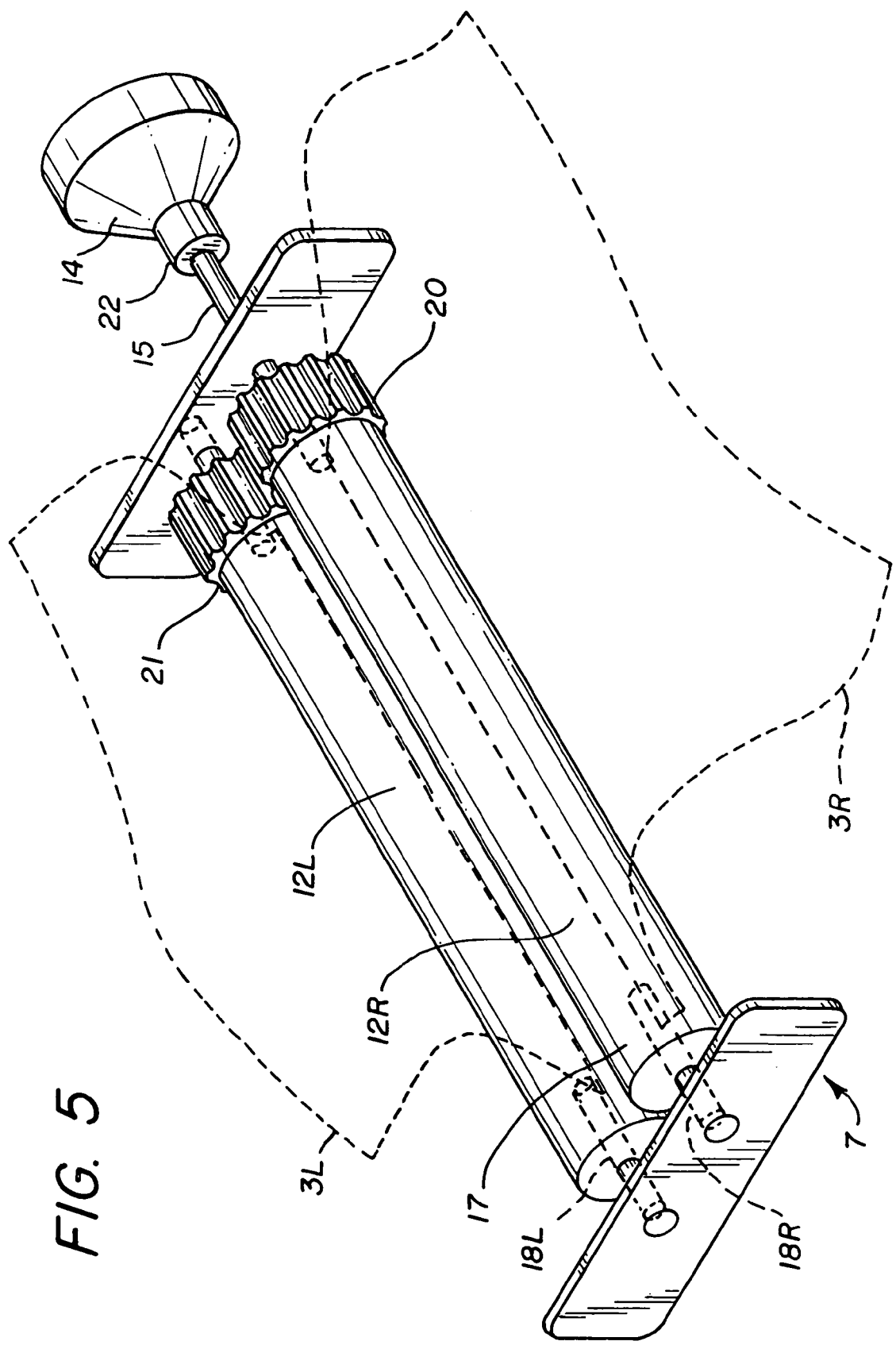
FIG. 5 shows an alternative embodiment of the spool assembly used to operate the compression belt.

Many alternative embodiments can be envisioned for the rolling mechanism, and one such alternative is illustrated in FIG. 5. Spools 12L and 12R are aligned in parallel and interconnected by a transmission gear 20 and planetary gear 21 and journaled upon shafts 18L and 18R. The drive shaft 15 is attached to spool 12R (or spool 12L) and operably attached to motor 14. The motor turns the shaft 15 and spool 12R in a counterclockwise direction to pull the right side of the compression belt 3R to the left and roll onto the spool. The transmission gear 20 acts upon the planetary gear 21 to cause clockwise rotation of spool 12L, which in turn pulls and wraps the left side of the compression belt 3L onto the spool 12L.

Thus, many embodiments of mechanisms which can cause repeated cyclic tightening of the compression vest about the chest of the victim may be envisioned. The compression belt serves to radially compress the chest through the cooperative action of the belt, board, and buckle, and to disperse the compressive force around the chest.

The motor is energized to rotate the spools and cause the compression belt to constrict around the chest of a victim. A motor such as a battery operated hand drill motor provides adequate chest compression for the purposes of CPR. To cause repetitive constriction of the compression belt 3, the motor 14 must be attached via a clutch 22 or other such mechanism. The motor 14 may be attached to the drive shaft 15 through a torque slipping clutching mechanism which engages the drive shaft until a high torque is achieved (indicating great resistance to further constriction, and thus indicating that the victim's chest has been compressed), and releases automatically upon such high torque, only to re-engage after the belt has been expanded in response to the normal elastic expansion of the victim's chest. In this manner, repetitive compression is achieved without need to repeatedly energize and de-energize the motor, thereby extending the length of operating time for any given battery supply. Alternatively, the motor may be repeatedly energized and de-energized, with the spools spinning freely during periods in which the belt is de-energized, wherein the clutch mechanism 22 will be similar to clutch mechanisms used on electric drills (which engage during operation of the drill but spin freely when the drill is de-energized). While the natural elastic expansion of the chest should make it unnecessary to drive the belt toward a loose condition, positive loosening may be achieved by reversing the motor or reversing the action of the motor through appropriate clutch or gear mechanisms. Timing of compressions is regulated through a computer module or a simple relay (windshield wiper style relays), and preferably will conform to standard of the Advanced Cardiac Life Support guidelines or Cardiopulmonary Resuscitation guidelines, or any other medically acceptable resuscitation regime. Current guidelines put forth by the American Heart Association call for 60 to 100 chest compressions per minute.

The motor is preferably battery powered, with provisions for taking power from any available power source. Batteries 23 may be stored within the support board 6. Three volt batteries of convenient size, already available for use with numerous power tools, provide about five minutes of compression per battery, while twelve-volt batteries (1700 mA-h per battery) have provided about ten minutes of compression per battery. A thirty minute total battery capacity is desirable (corresponding to the estimated average time between cardiac arrest and transport to the hospital). Accordingly, several batteries may be installed within the support board and electrically connected to the motor and its controller. The batteries are provided with a trickle charge through a charger socket and charger plugged into 120V AC power when the device is not in use. (It is intended that the device be installed in factories, office buildings, airplanes and other facilities with relatively stable sources of power, and that the unit remain plugged in and charging when not in use.) If AC power is readily available at the site of use, the device may continue to run on AC power to preserve the batteries for later use. The unit may also be plugged into an automobile power jack with an appropriate auto adapter, thus providing for use where an automobile is the only source of power, and for extended use in an ambulance.

Figure 6:
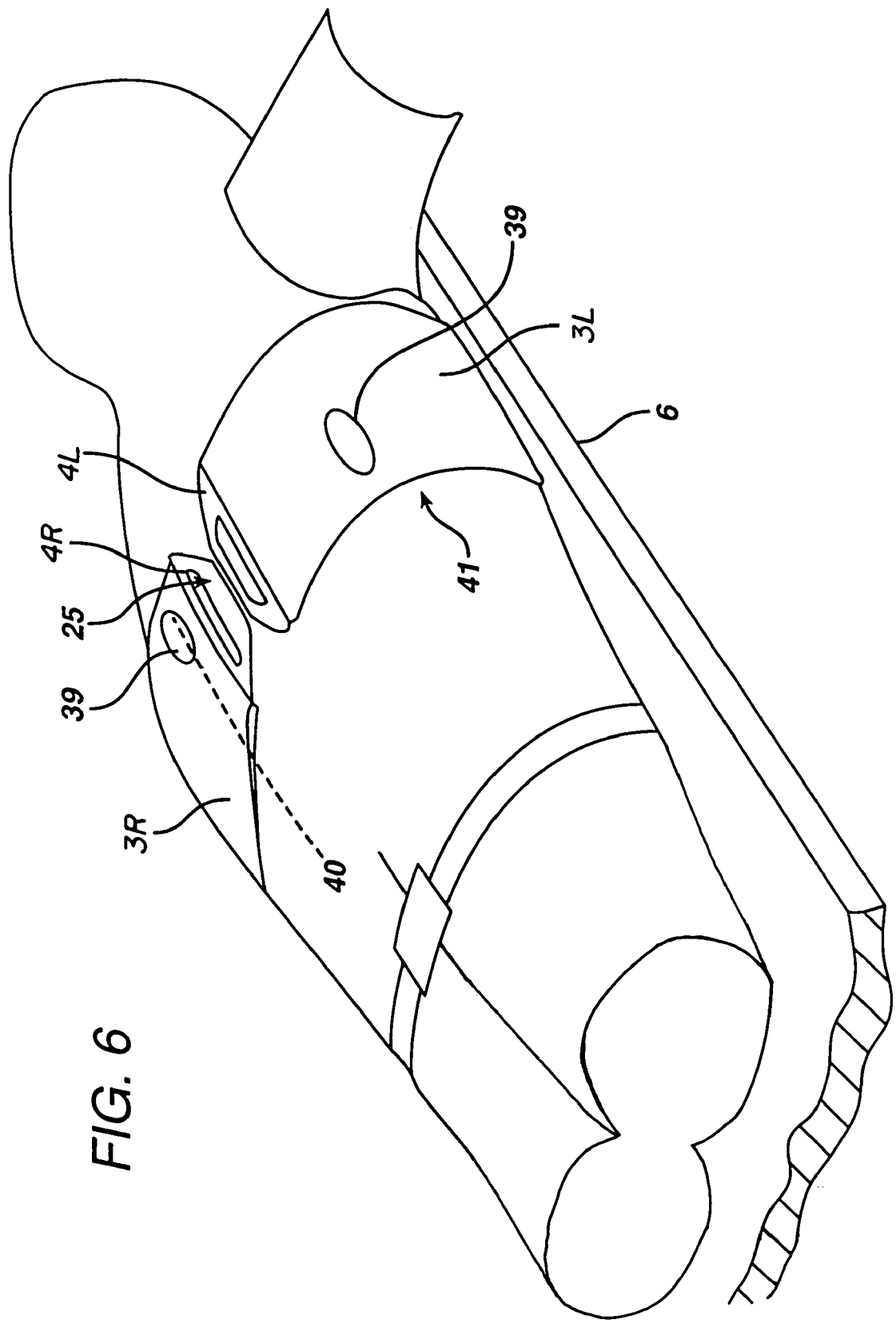
FIG. 6 is a view of the resuscitation device properly positioned on a victim.

FIG. 6 shows the resuscitation device installed on a cardiac arrest victim. The support board 6 is placed under the victim, and the right 3R and left 3L portions of the compression belt are wrapped around the victim's chest and buckled over the front of the chest, indicated by arrow 25. Once in place, the system may be put into operation by manually starting the motors or by automatic initiation given the proper feedback from sensors located on the device, including the buckle latch sensors.

Figure 7:
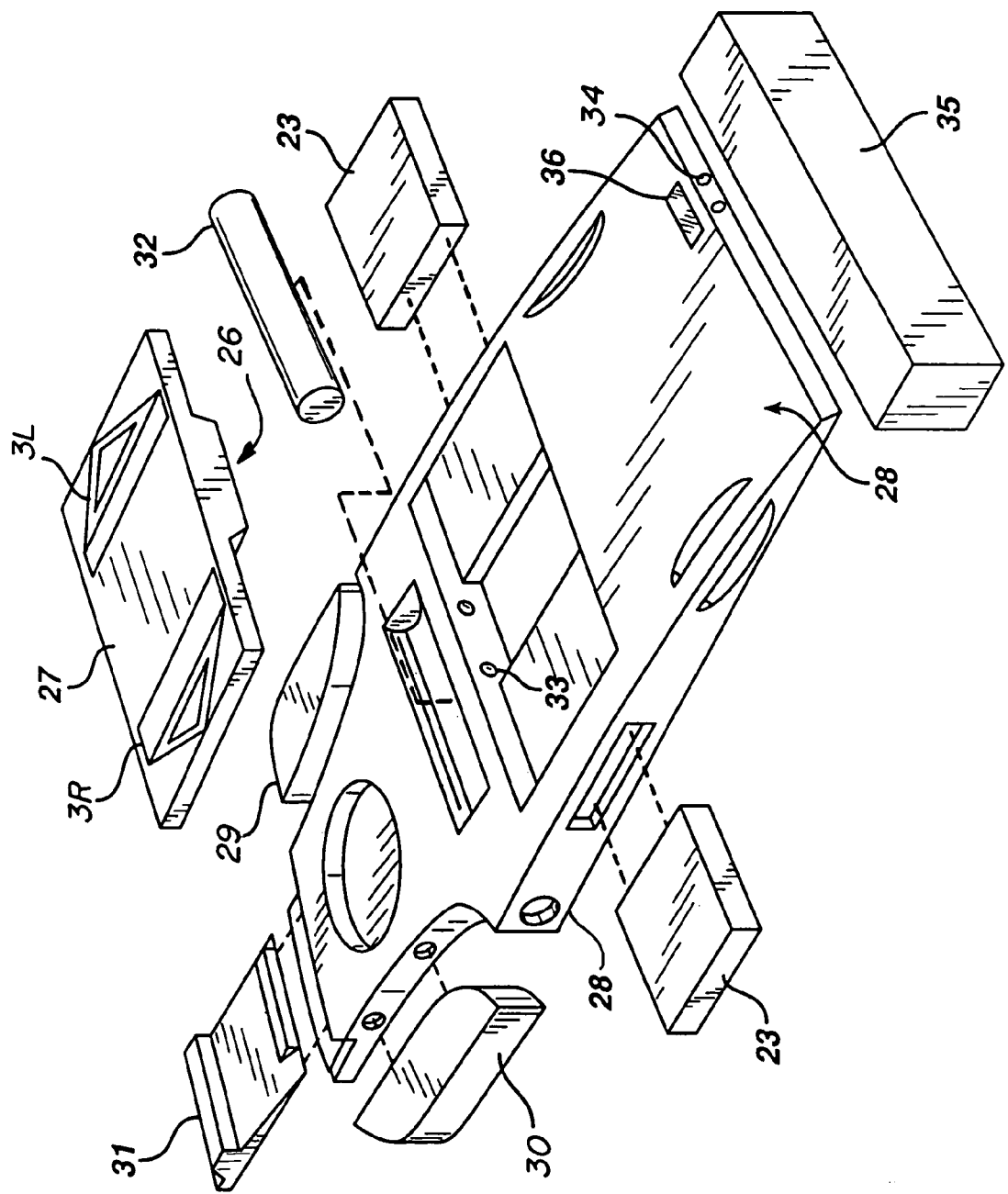
FIG. 7 shows the resuscitation device fitted with a number of additional devices for use during resuscitation.

A number of features may be combined with the basic system described above. The structure necessary for housing the operating mechanism for the belt, referred to as the support board above, can serve also as storage for additional devices used during resuscitation. FIG. 7 illustrates the resuscitation device 1 in a potential commercial embodiment. The support board is sized to reach approximately from the lower lumbar region to the shoulders of a victim. The compression module 26 is separable from the support board, and includes the compression belt and friction vest stored within the compression module. The spool assembly and motor are also stored within the compression module, although the motor may also be installed in the support board. In this figure, the compression module comprises a small support board 27 which fits into the larger system support board 28. Taking advantage of available space in the system support board, a compartment 29 for storage of airway management devices (bag masks, oxygen masks, etc.), and a compartment 30 for storage of defibrillation equipment (electrodes and paddles, etc.) are included with the support board.

A control and communication module 31 may also be incorporated into the support board. A small oxygen bottle 32 may be included, along with hoses routed to an accessible point on the board, and any connector desired for connection between the oxygen bottle and devices provided in the airway management compartment. Batteries 23 are stored within the support board (the number of the batteries chosen according the desired operating time, and the placement of the batteries dictated by available space). Batteries are operably connected to the motor in the compression module through electrical connectors 33 and appropriate wiring throughout the support board. The batteries can also be operably connected to the defibrillation module and control and communications module. Although long life batteries can be used, rechargeable batteries may be preferred. Accordingly, charging connection 34 on the support board is provided for charging the batteries or operating the device through outside power supplies.

The device is intended to be stored for long periods of time between uses, and storage holder 35 is provided for this purpose. The storage holder can include such necessities as power supply connectors, a power plug, and a charging transformer. A removal sensor 36 is included in the support board to sense when the support board is removed from the storage holder (which, as described below, can be used as a condition indicating use of the device, and therefore the need to alert emergency medical personnel). The removal sensor can comprise a simple limit switch which senses physical removal of the system, and the limit switch can be used as a power switch or awaken switch which starts initiation of the system. The removal sensor can comprise a current sensor on the charging lines which treat cessation of charging current, increase in current draw through the charging system, or motor current as an indication of use. The choice of sensor may be made with many practical considerations in mind, such as the desire to avoid treating power outages as indications of use and other such unintended initiations. The state in which the device is deemed to be "in use" can be chosen according to the practical considerations, and in most instances it is expected that mere removal of the resuscitation device from the holder will constitute a clear signal someone has determined that a victim requires its use, and that emergency medical personnel should be dispatched to the location of the device. There are some environments in which later conditions will be used to indicate that the device is "in use," such as when installed in ambulances, airplanes, hospitals or other environments where it might be advisable to remove the device from its storage holder as a precaution or preparatory measure, and delay initiation of communications until the device is deployed or installed on the victim. In such cases, the buckle latch shown in FIG. 3 can be used as the sensor that indicates that the resuscitation device is in use.

Figure 8:
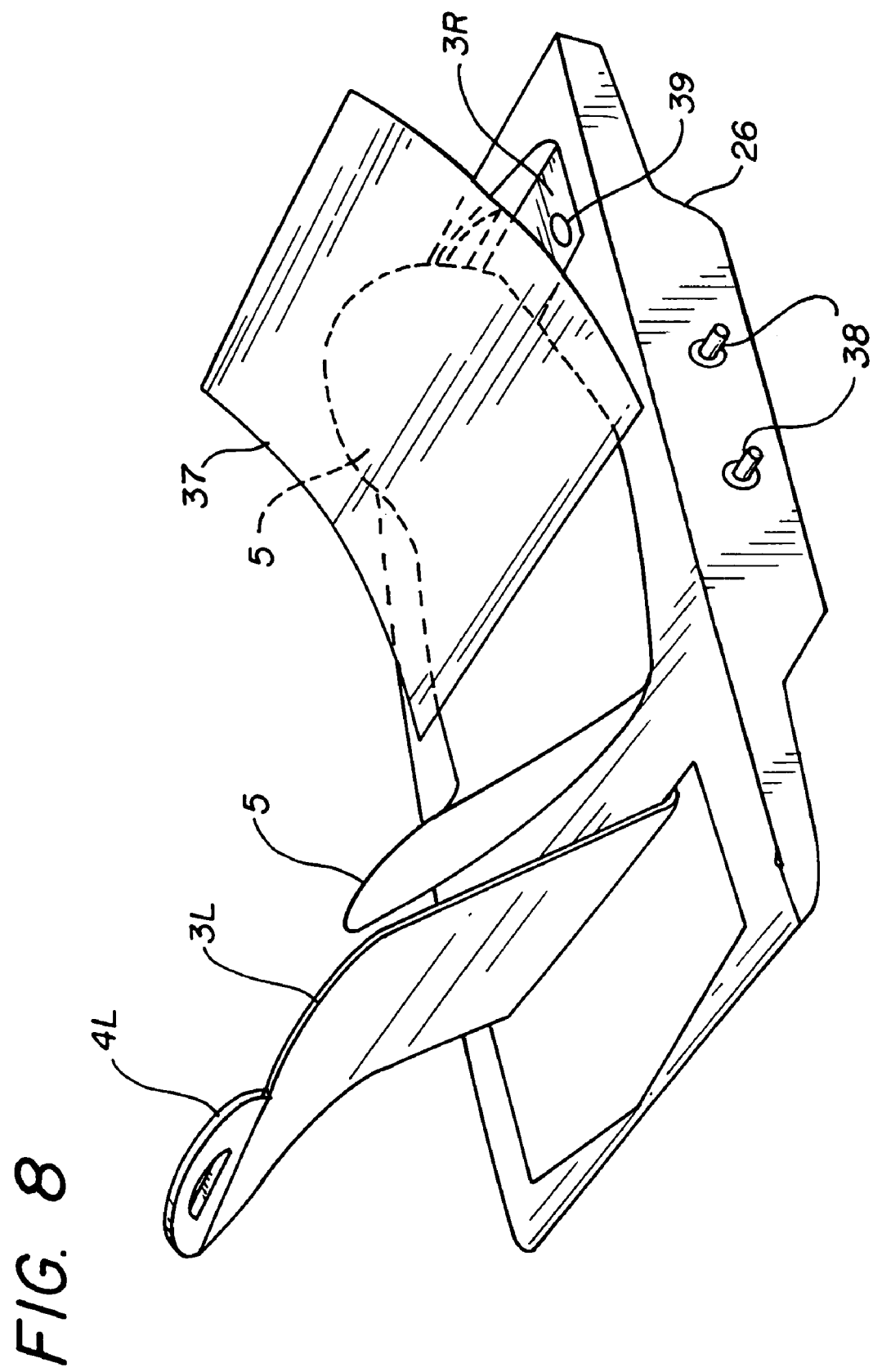
FIG. 8 shows a detail view of the CPR module of FIG. 7.

FIG. 8 shows the details of the compression module 26. When not in use, the module is covered with a tear sheet 37 which protects the compression belt from wear. The buckles 4 are readily visible under the tear sheet. The electrical connectors 38 connect the batteries in the support board with the motor inside the compression module. The inside of the compression belt 3 is fitted with penetrating electrodes 39 in the right sternum parasaggital location 40 (See FIG. 6) and left rib medial location 41 (See FIG. 6) for establishing the electrode contact needed for EKG sensing. These electrodes may be dispensed with in environments where proper placement of the defibrillation electrodes can be assumed due to a high level of training amongst likely bystanders and first responders. The friction vest 5 is secured to the compression module above the spool assembly location.

Figure 9:
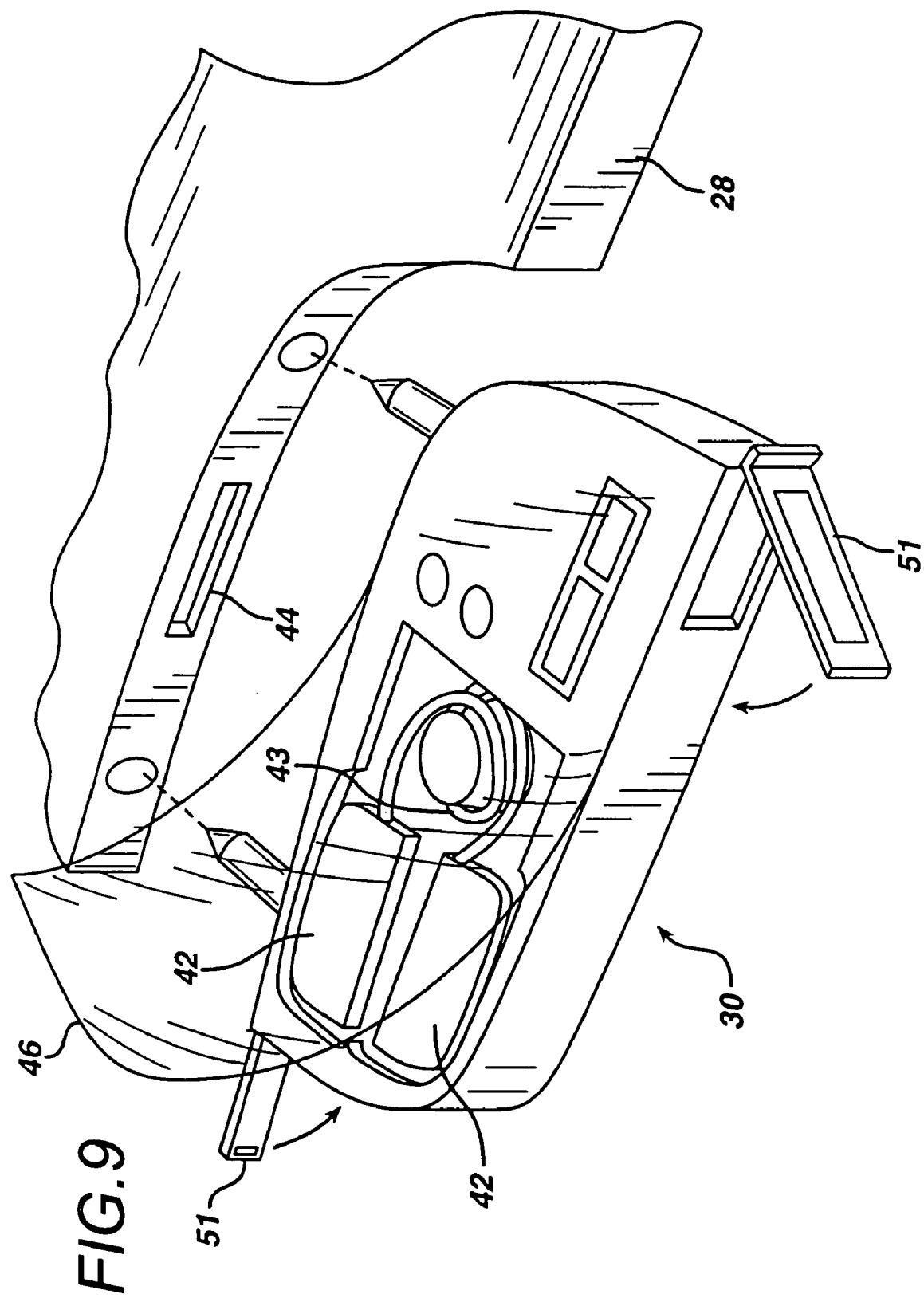
FIG. 9 shows a detail view of the defibrillation module of FIG. 7.

FIG. 9 shows a detail view of the defibrillation module 30. The defibrillation module includes a pair of defibrillation electrodes 42 connected to the batteries through the power connections 43. The defibrillation electrodes will be controlled by circuitry housed within the defibrillation module, and may be connected to the control module through the data port 44. The defibrillation module is releasably attached to the support board 28 with quick release latches 51. Tear sheet 46 protects the components of the defibrillation module during storage and provides ready access for use.

Figure 10:
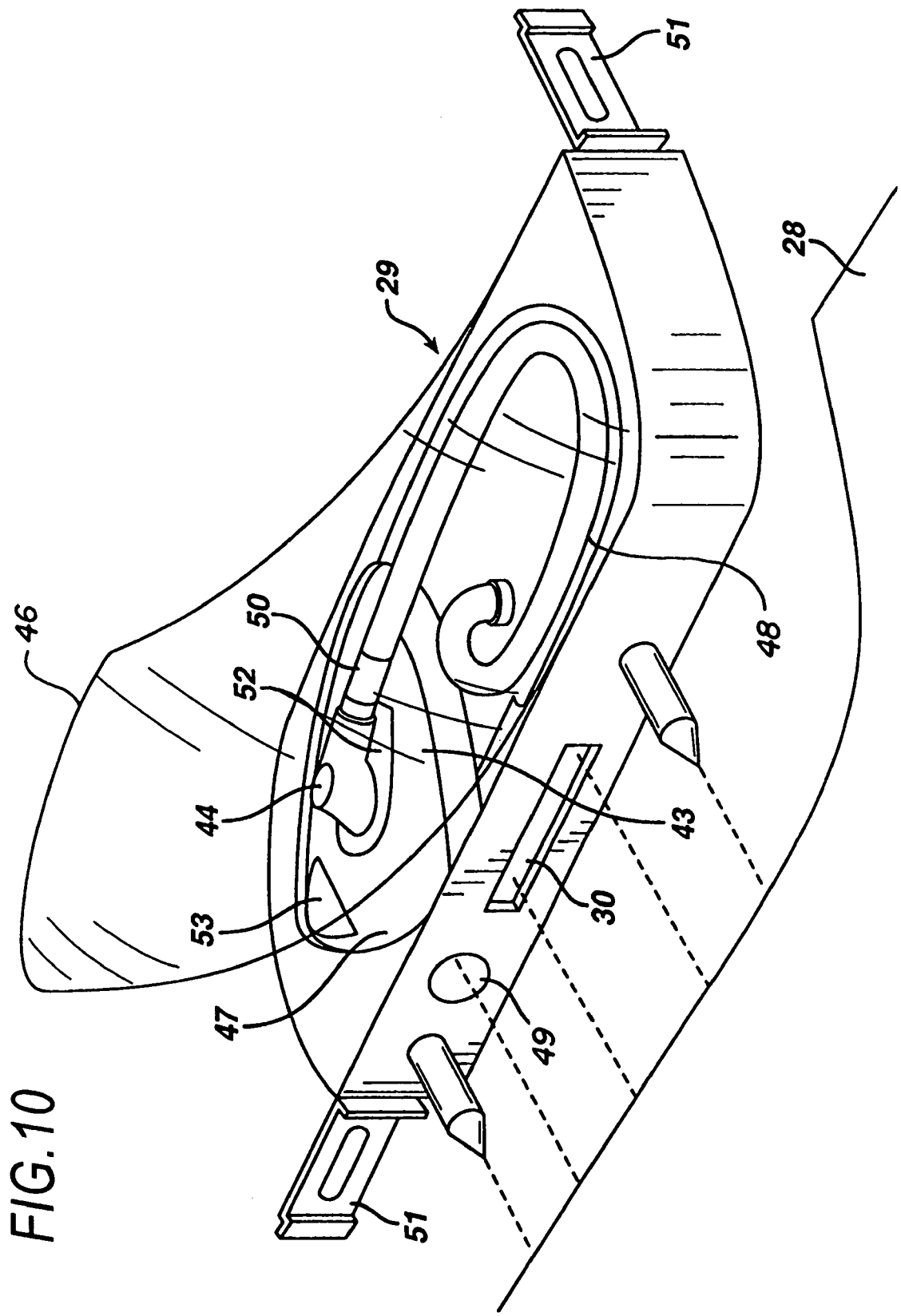
FIG. 10 shows a detail view of the airway management module of FIG. 7.

FIG. 10 shows the detail view of the airway management module 29, which includes an oxygen mask 47, a length of tubing 48 and an air fitting 49 connecting the oxygen mask to the oxygen bottle within the support board 28. The oxygen mask serves as a blood gas exchange means, supplying oxygen to the lungs for exchange with blood gas such as $CO_2$. Optional medicine injectors 50 may be operably connected to the masks or hose to provide for automatic injection of ACLS medications into the airway. The airway management module is releasably attached to the support board 28 with quick release latches 51. Tear sheet 46 protects the components of the airway management module during storage and provides ready access for use. An end-tidal $CO_2$ monitor 52 can be included in the mask to provide for biological feedback and monitoring of the success of the CPR. A skin mounted blood oxygen level monitor 53 can also be mounted on the mask for the same purpose (fingertip blood oxygen sensors may also be used, and supplied in the overall assembly to be readily available). The biological data obtained by the sensors is transmitted to the control module via appropriate wiring in the mask and support board.

Figure 11:
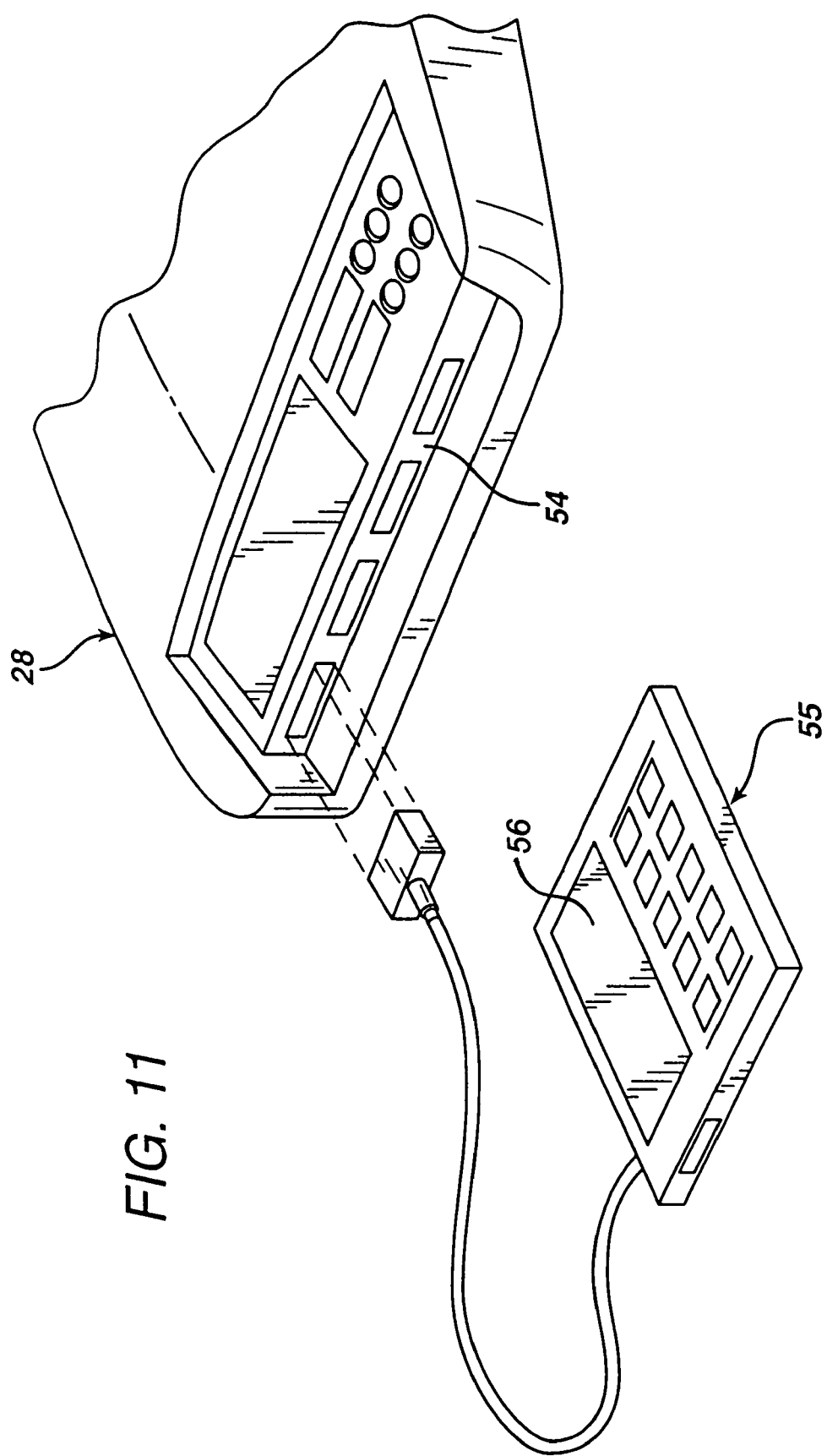
FIG. 11 shows a detail view of the control and communications module of FIG. 7.

FIG. 11 shows a detail view of the control and communications module. The control unit 54 is connected to the compression module, defibrillation module and the airway management module through appropriate wiring through the support board 28. The control unit is optionally connected to the communications unit 55. The communications unit includes means for communicating the EKG and other measured medical parameters sensed on the board to the screen 56 and via telephone to remote medical personnel. The communications unit can include a telephone handset or speaker phone. Because the device is most likely to be used at a location separate from the storage holder, the communications module preferably includes a wireless communication device, such as wireless telephone, radio telephone or cellular, and any necessary telephone base will be installed in the storage holder.

Figure 12A:
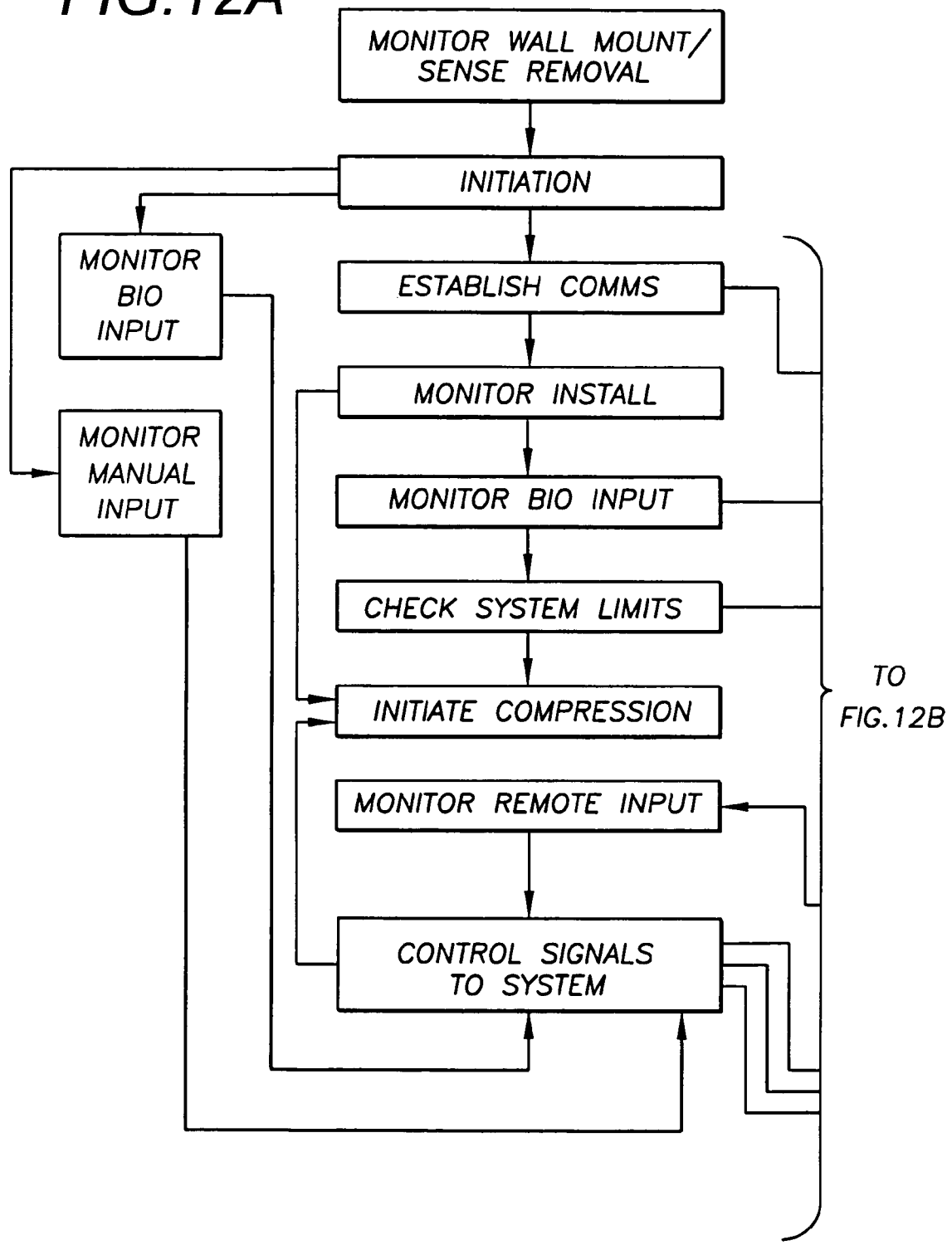
FIG. 12 shows a block diagram of the communications system.
Figure 12B:
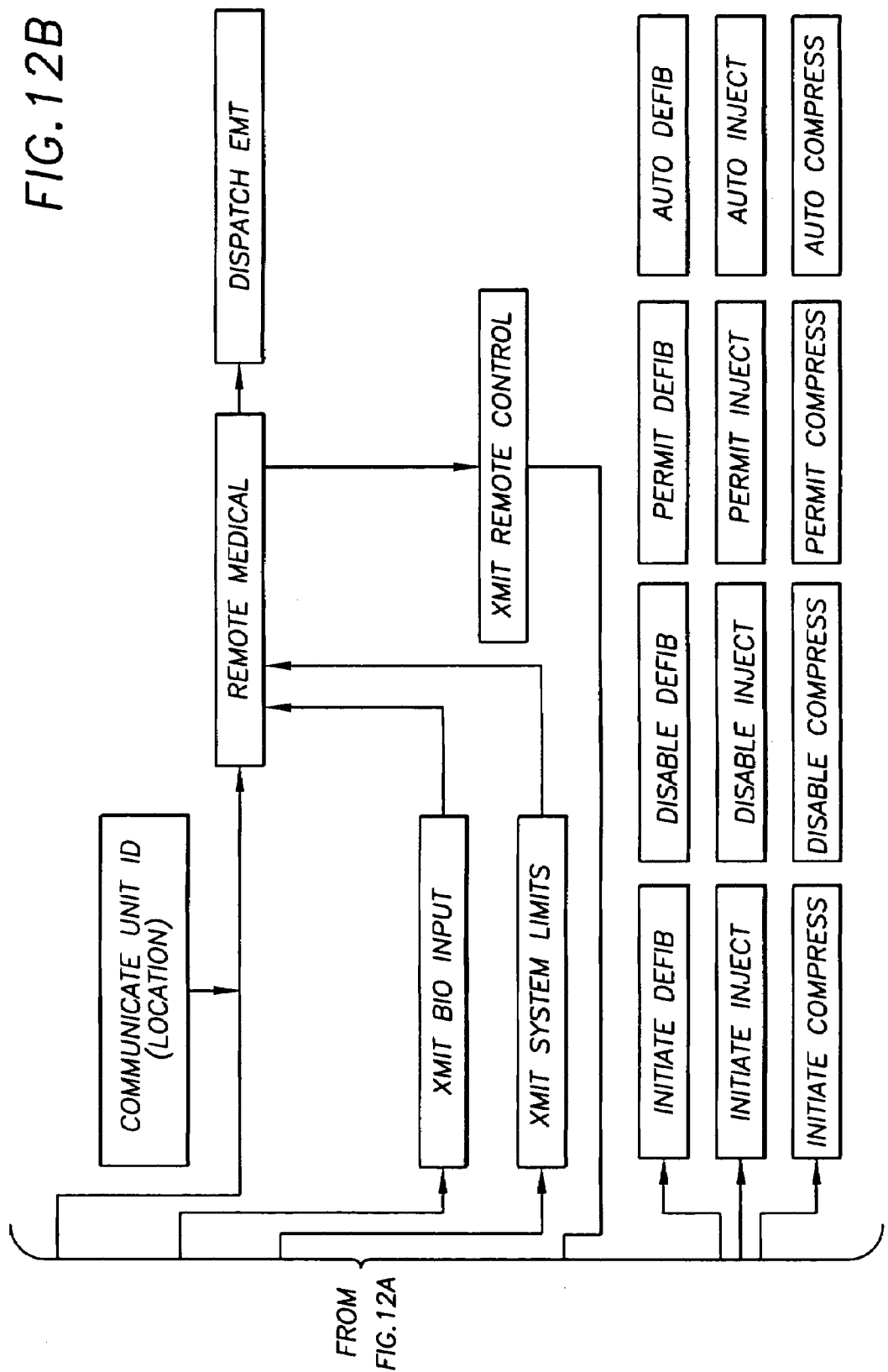

The communications unit and control unit are set up to operate in the following manner, also illustrated in the block diagram of FIG. 12. The device may remain mounted in a charging unit for months between uses, and will be removed from the charging unit for use. Upon removal of the device from its storage location, a sensor in the control unit senses the removal (through limit switches, magnetic switches, or motion sensors, current sensors in the charging system, or otherwise) and initiates the system, checking functions, energizing a display unit and accomplishing other typical warm-up functions. As a first step, the system initiates a telephone communication with a medical facility through the communications unit. The communication may use any communication medium, whether it be standard telephone lines, cellular telephone system, paging system or radio transmitter. The system may be set up to initiate communications with central medical facility, such as a local 911 emergency system, a nearby hospital or ambulance service, or a central facility staffed with medical personnel trained specifically on the remote use of the device (all generally referred to as medical personnel). Upon establishing communication, the communications unit informs medical personnel of the location or identification of the device (which may be stored in computer memory in the communications unit, or determined through GPS or other such system), and this information can be used to dispatch an emergency medical team to the location of the device. In a simple embodiment which does not require a computer to control the actions of the alert feature, the removal sensor may comprise a limit switch, while the communications module may comprise a simple telephone unit installed in the storage holder together with a tape recorded message, where the operation of the relay in response to removal of the resuscitation device includes initiation of the telephone call to 911 and playback of an alert message providing alert information such as the location of the board. The communications unit may also be provided with an alert button which may be operated by a bystander regardless of the use of the board to summon an emergency team to the location regardless of the condition of the resuscitation device.

Before the emergency medical team arrives, a bystander will place the board under the victim, buckle the compression belt around the victim, and apply the defibrillation and/or sensing electrodes (or vice versa). Alternatively, sensing electrodes can be included on the inner surface of the compression belt. The system monitors the installation of the belt through signals provided by the latching sensors in the buckle. The system monitors biological input, which can comprise monitoring of EKG signals from the EKG electrode patches of the defibrillation module, monitoring EKG signals measured by the belt mounted electrodes, monitoring signals from an end-tidal $CO_2$ monitor from the airway management module, and any other biological signal sensor incorporated into the device. The system can also monitor or respond to manually inputted instructions from the control unit, in order to provide on-site emergency medical personnel with control of the device when they arrive on scene. During operation, the system transmits all available biological information, including EKG signals, blood pressure, end-tidal $CO_2$ and any other monitored biological parameter to the remote medical facility, and it can also transmit information regarding the configuration of the device, including battery life, system operating limit settings (i.e., whether the system is set for automatic operation, permissive operation, or disabled in any function) so that medical personnel can ensure that the appropriate configuration is in effect.

Communication with the medical facility will allow emergency medical personnel to diagnose the condition of the patient and, through signals sent from the medical personnel to the communications unit, permit, initiate or prohibit certain additional therapeutic ACLS actions. For example, upon diagnosing the EKG conditions which indicate the need for defibrillation, the medical personnel can send a signal to the communications unit which acts upon the control unit to permit manual operation of the defibrillation electrodes by the bystander. The system also provides for application of a defibrillation shock via remote signal from the medical personnel. The device can incorporate an expert system such as the Automatic External Defibrillator. The medical personnel can also communicate other actions and ensure that certain acts are undertaken by the bystander through the communication system. For example, the medical personnel may communicate verbally with the bystander to ascertain the cause of the cardiac arrest, the proper placement of the oxygen mask, appropriate clearing of the airway, and other information. Where the airway management module is provided with medication such as epinephrine, lidocaine, bretylium or other drugs called for in the ACLS guidelines (or newly proposed drugs such as T3), the medical personnel can instruct bystanders to inject the appropriate medication through the airway. Where automatic injectors such as those described in Kramer, Interactive External Defibrillation and Drug Injection System, U.S. Pat. No. 5,405,362 (Apr. 11, 1995) are provided, or similar system with non-osseous injectors are provided, the medical personnel can instruct bystanders to inject appropriate medication through these injectors. Where the injectors are provided with means for automatic operation based on measured EKG signals, blood pressure and end-tidal $CO_2$, the medical personnel can send signals to the system to initiate injection by remote control of the medical personnel, permit injection by local control as determined by the expert system, permit injection by bystanders, or prohibit injection by the system or bystanders. For example, the system can be initially set up to forbid any injection. Medical personnel, having diagnosed ventricular fibrillation through the information provided by the communications unit, can send an appropriate signal to permit or initiate injection of epinephrine, and also send a signal to prohibit injection of atropine until called for under the ACLS guidelines. A newly proposed drug T3 can be administered through the airway, into the lungs, as a therapy for cardiac arrest. Controlled injection into the airway can be initiated or prohibited in the same manner. Thus, all actions in the ACLS, including compression, defibrillation, drug injection can be accomplished through the system under the guidance of medical personnel from a remote location, or they may be accomplished through expert systems installed in the control module. Each of these functions is incorporated into a system that automatically initiates communication with medical personnel and informs medical personnel of the location of the device so that emergency medical personnel may be dispatched to the location.

The repeated compression will be initiated upon buckling of the compression belt (automatically) or a switch can be provided for the bystander to initiate compression. The system will continue compression cycles, until de-activated, according the motor control block diagram of FIG. 13. Upon initiation of the system, the control unit will monitor installation of the belt via appropriate sensors in the buckles or through other sensors. When the motor control 57 receives the initiate compression signal from the control unit, the motor is started. The motor is preferably run continuously, rather than stopped and started, to avoid repeated application of startup current and thus conserve battery power. When the motor is up to speed, the clutch is engaged. As a baseline, the clutch is engaged every second for one-half second. This cyclic engagement of the clutch continues repeatedly for five cycles, as recommended by current CPR guidelines, and then is interrupted for a respiration pause, if desired. To avoid excessive drain on the batteries, the motor controller includes a torque sensor (sensing current supply to the motor, for example), and monitors the torque or load on the motor. A threshold is established above which further compression is not desired or useful, and if this occurs during the half second of clutch engagement, then the clutch is disengaged and the cycle continues. The system can monitor the effectiveness of the compression stroke by monitoring the $CO_2$ content of the victim's exhalant. Where $CO_2$ content is low, indicating inadequate circulation, the control system increases the torque limit until the $CO_2$ levels are acceptable (or until the maximum torque of the motor is achieved.) This is another example of the device's use of biological signals to control operation of the system. The cycle time and period, number of cycles between respiration pauses, and the torque limit, can be set according to current guidelines, and can also be varied by the remote medical personnel via the remote control capabilities of the control unit.

Figure 14:
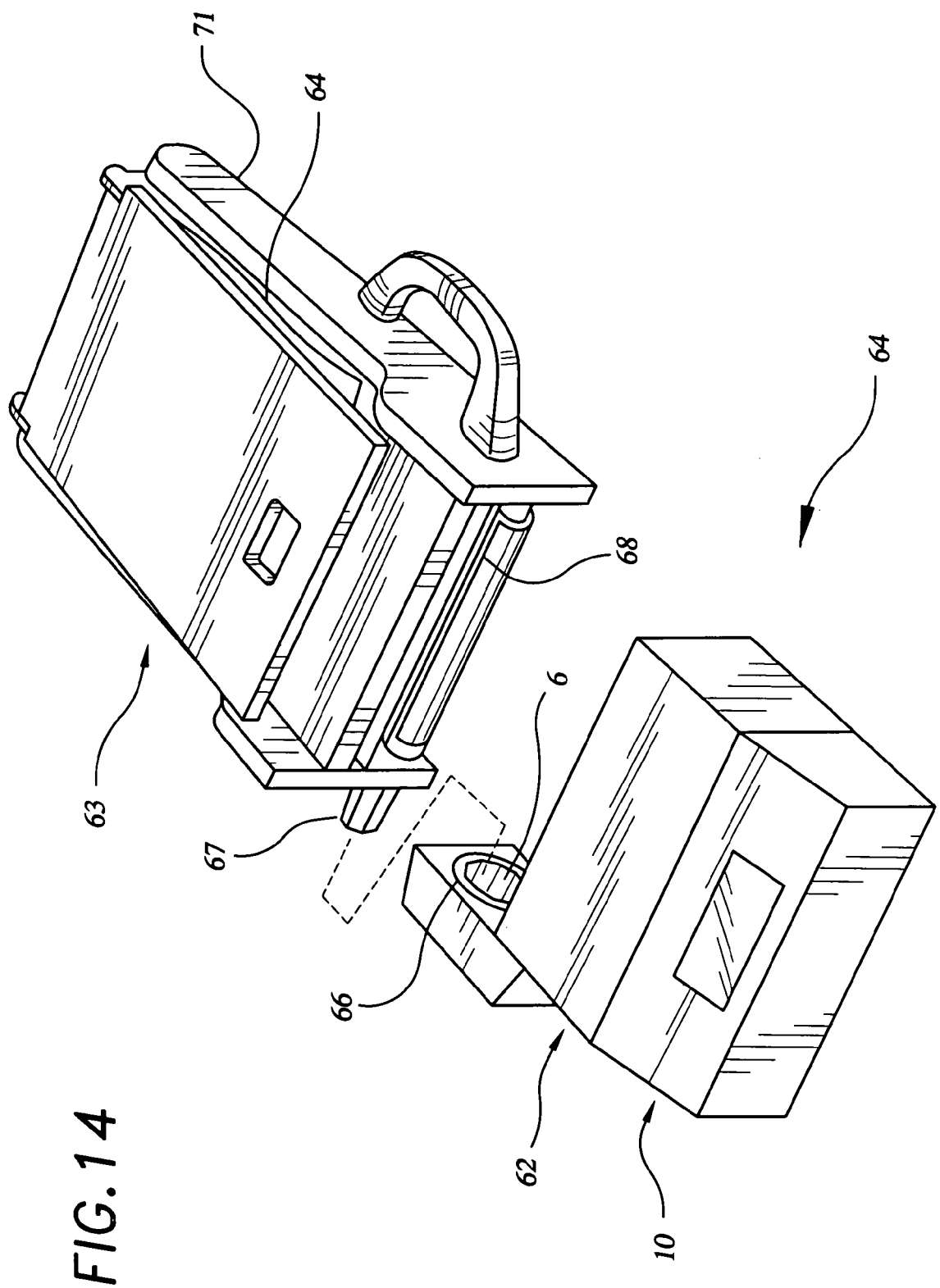
FIG. 14 is an overview of the resuscitation device.

FIG. 14 shows an overview of the resuscitation device 61. The major components are provided in modular form, and include the motor box 62, the belt cartridge 63 and the belt 64. The motor box exterior includes a sprocket 65 in a drive wheel 66 which releasable mates with the receiving rod 67 on the cartridge. The cartridge houses the belt which will wrap around the chest of the patient. The cartridge also includes the spool 68 which is turned by the receiving rod. The spool takes up the midpoint of the belt to drive the compression cycles. A computer control system 70 may be included as shown in an enclosure mounted on the motor box. By providing the system in modular form, with the motor box releasable attached to the belt cartridge, the belt cartridge may more easily be maneuvered while slipping it under the patient.

Figure 15:
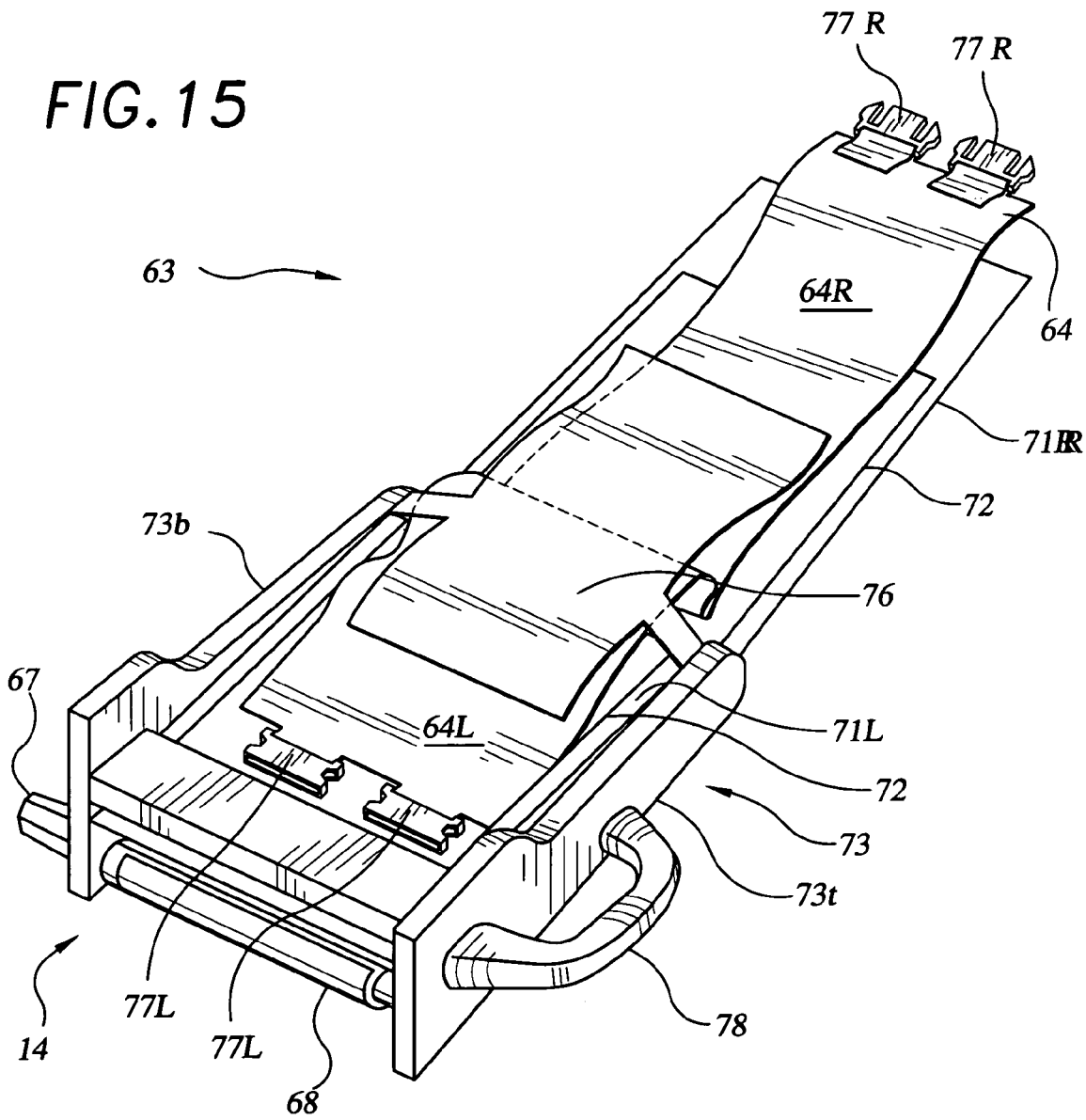
FIG. 15 illustrates the installation of the belt cartridge.

FIG. 15 shows a more detailed view of the cartridge, including the internal mechanisms of the belt cartridge 63. The outer body of the cartridge provides for protection of the belt during storage, and includes a back plate 71 with a left panel 71L and a right panel 71R (relative to the patient during use). The right plate can be folded over the left plate for storage and transport. Both panels are covered with a sheet 72 of low friction material such as PTFE (Teflon®) to reduce friction when the belt slides over the panel during operation. Under the left panel, the cartridge has a housing 73 which houses the middle portion of the belt, the spool 68 and the spindle 75 (See FIG. 16). The lateral side 74 of the cartridge (corresponding to the anatomic position when in use on a patient) houses the drive spool 68, with its drive rod 67 which engages the drive wheel 66 (See FIG. 14) of the motor box. The cartridge also houses the guide spindle 75 (visible in FIG. 16) for directing the belt toward the drive spool 68. The guide spindle is located near the center of the cartridge (corresponding to the medial line of the patient when in use), so that it is located near the spine when the device is in use. This spindle reverses the belt travel for the left side of the belt, so that when it is pulled to the left by the drive spool, the portion that wraps around the left flank of the body moves to the right. The cartridge body is also hinged near the mid-line, and in this view the cartridge is hinged near the axis of the spindle. A friction liner 76 is suspended over the belt in the area of the guide spindle, and is attached to the housing at the top and bottom panels 73t and 73b and spans the area in which the left belt portions and right belt portions diverge from the cartridge. The belt 64 is shown in the open condition. Male quick release fittings 77R on the right belt portion fit into corresponding female quick release 77L fittings on the left belt portion to releasably secure the belt around the patient's chest. The belt length on the left and right sides of the belt may be adjusted so that the buckles fall just over the center of the patient's chest during operation, or they may be adjusted for placement of the buckles elsewhere around the chest. The handle 78 is provided for convenient handling and carrying of the device.

Figure 16:
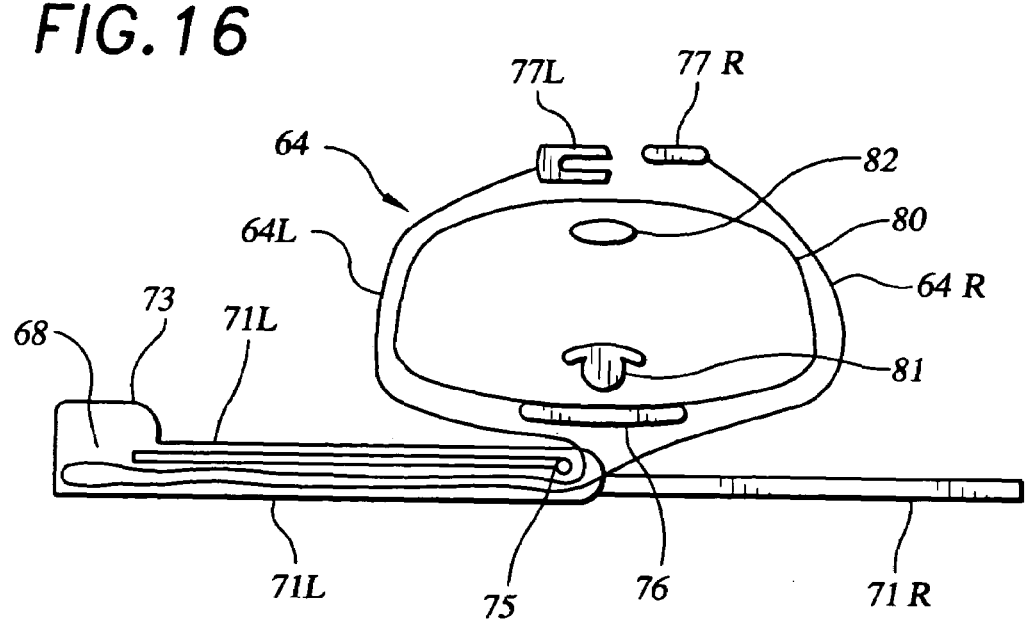
FIG. 16 illustrates the operation of the belt cartridge.

FIG. 16 shows a cross section of the belt cartridge. The housing 73 is relatively flat, (but may be wedge shaped to assist in sliding it under a patient) when viewed from the superior position. The left panel 71L sits atop the housing 73 and the right panel extends from the housing. In the unfolded position, the cartridge is flat enough to be slipped under a patient from the side. In the cross-sectional view, the guide spindle 75 can be seen, and the manner in which the belt is threaded through the slot 69 of the drive spool 68 appears more clearly. The belt 64 comprises a single long band of tough fabric threaded through the drive spool slot 69 and extending from the drive spool to the right side quick releases 77R and also from the drive spool, over and around the guide spindle, and back toward the drive spool to the left side quick releases 77L. The belt is threaded through the drive spool 68 at its mid-portion, and around the guide spindle, where the left belt portion 64L folds around the guide spindle, under the friction liner and back to the left side of the cartridge, and the right belt portion 64R passes the spindle to reach around the patient's right side. The friction belt liner 76 is suspended above the guide spindle and belt, being mounted on the housing, and fits between the patient and the compression belt. The cartridge is placed under the patient 80, so that the guide spindle is located close to the spine 81 and substantially parallel to the spine, and the quick release fittings may be fastened over the chest in the general area of the sternum 82.

Figure 17:
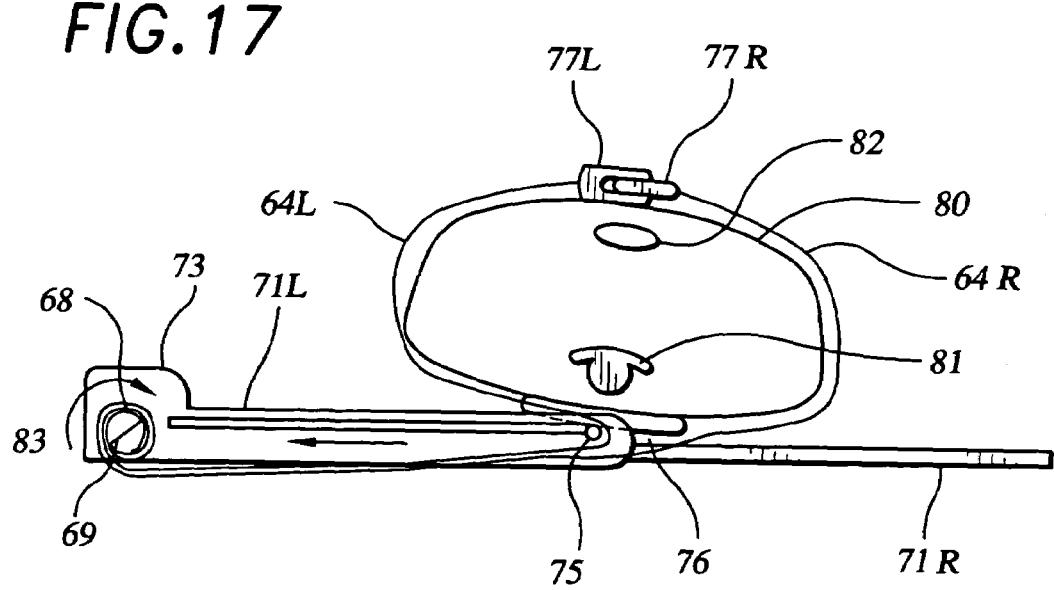
FIG. 17 illustrates the operation of the belt cartridge.

In use, the cartridge is slipped under the patient 80 and the left and right quick releases 77L and 77R are connected. As shown in FIG. 17, when the drive spool is rotated, it takes up the middle portion of the belt and tightens the belt around the chest. The compression force exerted by the belt is more than sufficient to induce or increase intrathoracic pressure necessary for CPR. When the belt is spooled around the drive spool 68, the chest of the patient is compressed significantly, as illustrated.

While it will usually be preferred to slide the cartridge under the patient, this is not necessary. The device may be fitted onto the patient with the buckles at the back or side, or with the motor to the side or above the patient, whenever space restrictions require it. As show in FIG. 18, the cartridge may be fitted onto a patient 80 with only the right belt portion 64R and right panel 71R slipped under the patient, and with the right panel and left panel partially unfolded. The placement of the hinge between the right side and left side panels permits flexibility in installation of the device.

FIGS. 19 through 22 show that the cartridge may also be fitted onto a patient 80 with both the right panel 71R and the left panel 71L slipped under the patient, but with the motor box 62 folded upward, rotated about the axis of the drive spool 68. These configurations are permitted by the modular nature of the motor box connection to the belt cartridge, and will prove useful in close spaces such as ambulances and helicopters. (Note that, although the belt may be tightened by spooling operation in either direction, tightening in the direction of arrow 83, clockwise when viewed from the top of the patient and the device, will cause reactive force which urges the motor box to rotate into the device, toward the body, rather than outwardly away from the body. Locking pins may be provided to prevent any rotational movement between the motor box and the cartridge. In the construction of the motor box as shown, the limited height of the box (the height of the box is less than the distance between the left flank of the patient and the drive spool) prevents contact with the patient in case the locking pins are not engaged for any reason. The rotation of the drive belt may be reversed to a counter clockwise direction, in which reactive force will urge the motor box to rotate outwardly. In this case, locking mechanisms such as locking pins can be used to protect operators from movement of the system.)

Figure 18:
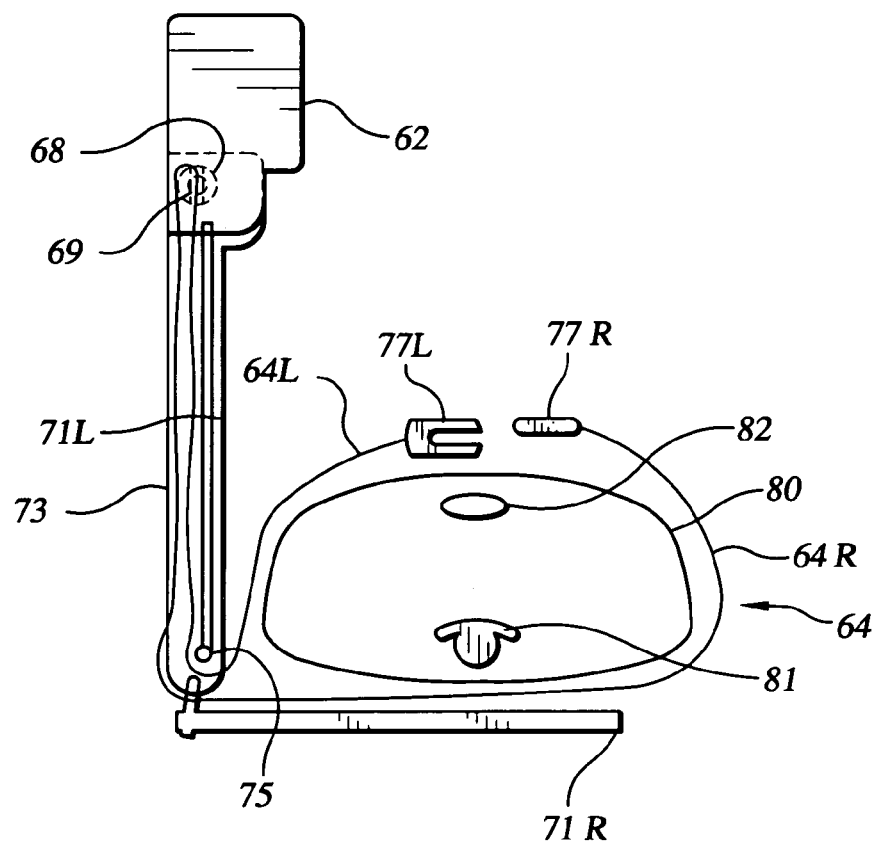
FIG. 18 illustrates an alternative configuration of the belt cartridge.
Figure 19:
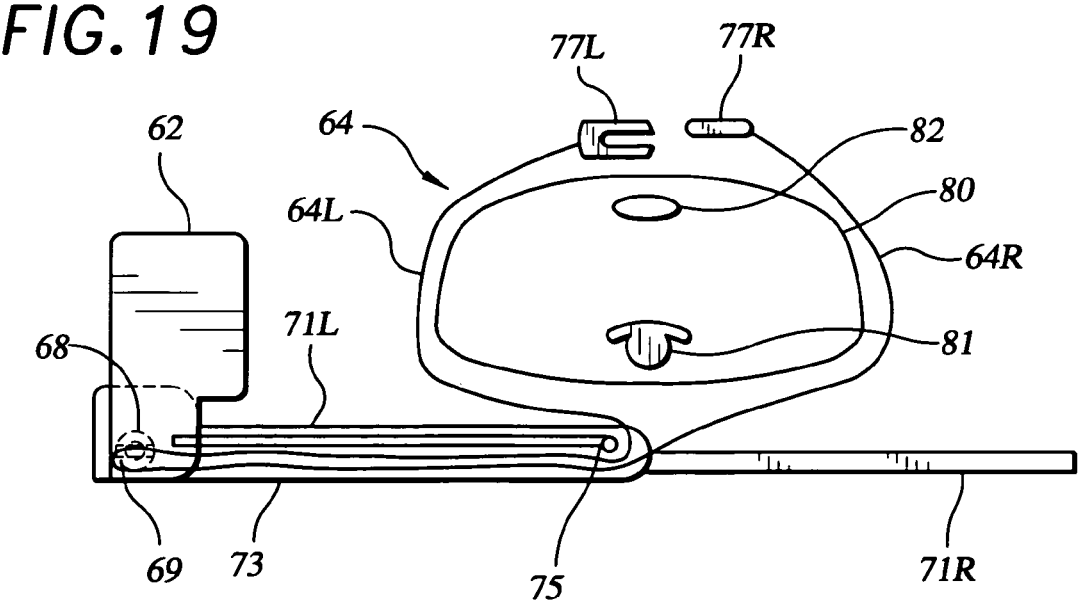
FIG. 19 illustrates an alternative configuration of the belt cartridge.

Regardless of the orientation of the panels, the reversing spindle will properly orient the travel of the belt to ensure compression. The placement of the spindle at the point where the right belt portion and the left belt portion diverge under the patient's chest, and the placement of this spindle in close proximity to the body, permits the belt to make contact with the chest at substantially all points on the circumference of the chest. The position of the spindle reverses the travel of the belt left portion 64L from a transverse right to left direction to a transverse left to right direction, while the fact that belt right portion 64R bypasses the spindle means that it always moves from right to left in relation to the patient when pulled by the drive spool. Thus the portions of the belt engaging the chest always pull from opposite lateral areas of the chest to a common point near a central point. In FIGS. 16 and 17, the opposite lateral areas correspond to the anatomic lateral area of the patient, and the central point corresponds to the spine. In FIG. 18, the lateral areas correspond to the spine and anterior left side of the torso, while the central point corresponds to the left lateral area of the chest. Additionally, the use of the single spindle at the center of the body, with the drive spool placed at the side of the body, permits simple construction and the detachable or modular embodiment of the motor assembly, and allows placement of the belt about the patient before attachment of the motor box to the entire device.

Figure 20:
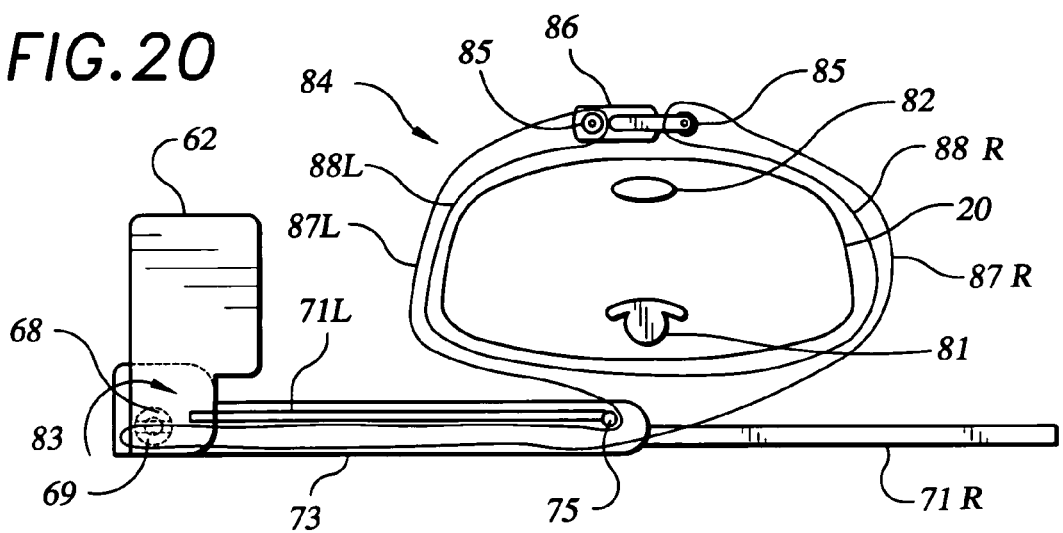
FIG. 20 illustrates an alternative configuration of the belt cartridge.

FIG. 20 illustrates an embodiment of the compression belt which reduces the take up speed for a given motor speed or gearing and allows for twice the compressive force for a given motor speed. The compression belt comprises a loop 84 of belt material. The loop is threaded through the complex path around spindles 85 in the quick release fasteners 86, around the body to the guide spindle 75, around or past the guide spindle and into the drive spool 68. The left belt portion outer layer 87L and right belt portion outer layer 87R form, together with the left belt portion inner layer 88L and right belt portion inner layer 88R form a continuous loop running inwardly from the fastener spindle, inwardly around the chest to the opposite fastener spindle, outwardly from the opposite fastener spindle, downwardly over the chest, past the guide spindle to the drive spool, through the drive spool slot and back under the guide spindle, reversing around the guide spindle and upwardly over the chest back to the fastener spindle. Thus both the inner and outer layers of this two layer belt are pulled toward the drive spool to exert compressive force on the body. This can provide for a decrease in friction as the belts will act on each other rather than directly on the patient. It will also allow for a lower torque, higher speed motor to exert the necessary force.

Figure 21:
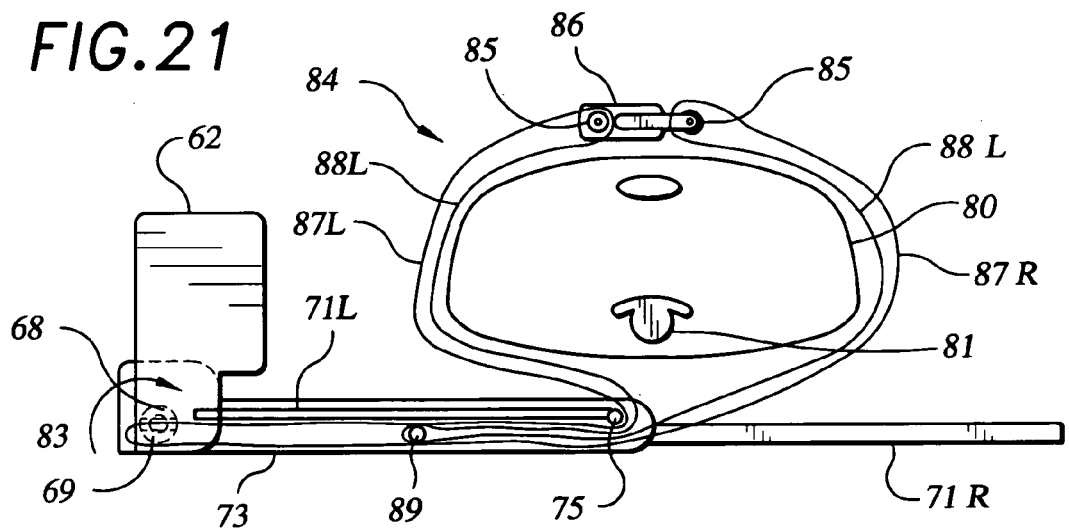
FIG. 21 illustrates an alternative configuration of the belt cartridge.

In FIG. 21, the double layer belt system is modified with structure which locks the inner belt portion in place, and prevents it from moving along the body surface. This has the advantage that the major portion of the belt in contact with the body does not slide relative to the body. To lock the belt inner layer in place relative to the loop pathway, the locking bar 89 is fixed within the housing 73 in parallel with the guide spindle 75 and the drive spool 68. The inner loop may be secured and fastened to the locking bar, or it may be slidably looped over the locking bar (and the locking bar may be rotatable, as a spindle). The left belt portion outer layer 87L and right belt portion outer layer 87R are threaded through the drive spool 68. With the locking bar installed, the rotation of the drive spool takes up the outer layer of the belt, and these outer layers are forced to slide over the left belt portion inner layer 88L and right belt portion inner layer 88R, but the inner layers do not slide relative to the surface of the patient (except, possibly, during a brief few cycles in which the belt centers itself around the patient, which will occur spontaneously due to the forces applied to the belt.

Figure 22:
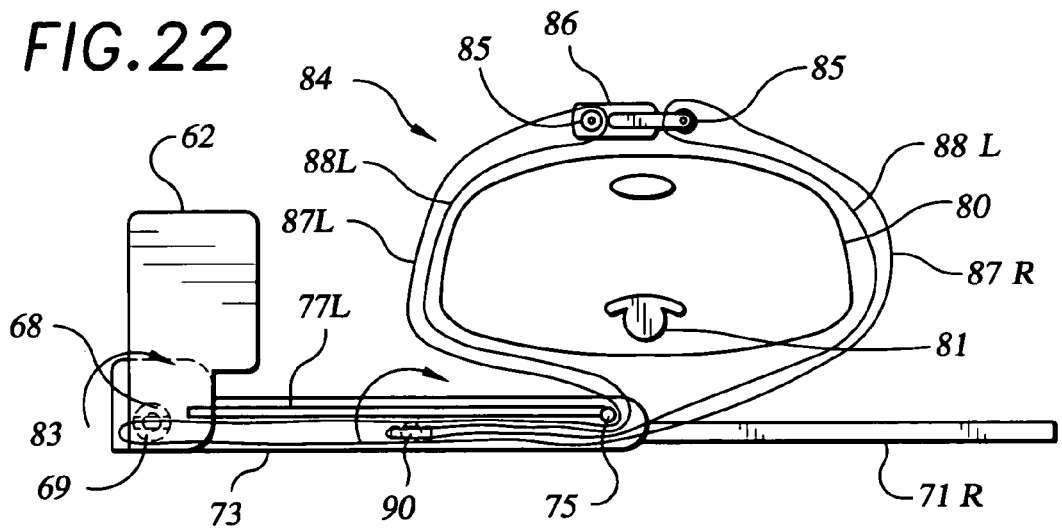
FIG. 22 illustrates an alternative configuration of the belt cartridge.

In FIG. 22, the double layer belt system is modified with structure which does not lock the inner belt portion in place or prevent it from moving along the body surface, but instead provides a second drive spool to act on the inner layer of the belt. To drive the belt inner layer relative to the loop pathway, the secondary drive spool 90 is fixed within the housing 73 in parallel with the guide spindle 75 and the drive spool 68. This secondary drive spool is driven by the motor, either through transmission geared within the housing or through a second receiving rod protruding from the housing and a secondary drive socket driven through appropriate gearing in the motor box. The inner loop may be secured and fastened to the secondary drive spool, or it may be threaded through a secondary drive spool slot. The left belt portion outer layer 87L and right belt portion outer layer 87R are threaded through the first drive spool 68. With the secondary drive spool, the rotation of the first drive spool 68 takes up the outer layer of the belt, and these outer layers are forced to slide over the left belt portion inner layer 88L and right belt portion inner layer 88R, while the secondary drive spool takes up the inner layers.

Figure 23:
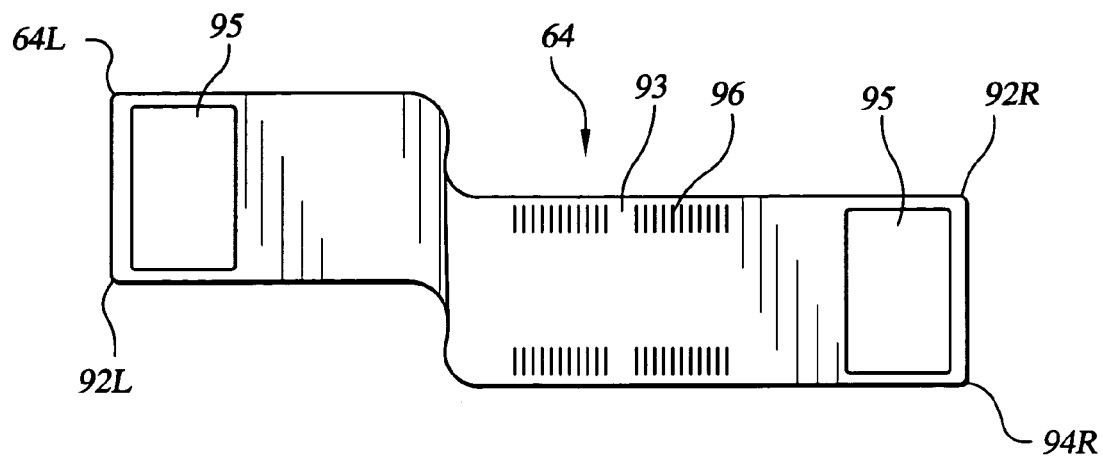
FIG. 23 illustrates an alternative embodiment of the belt.
Figure 24:
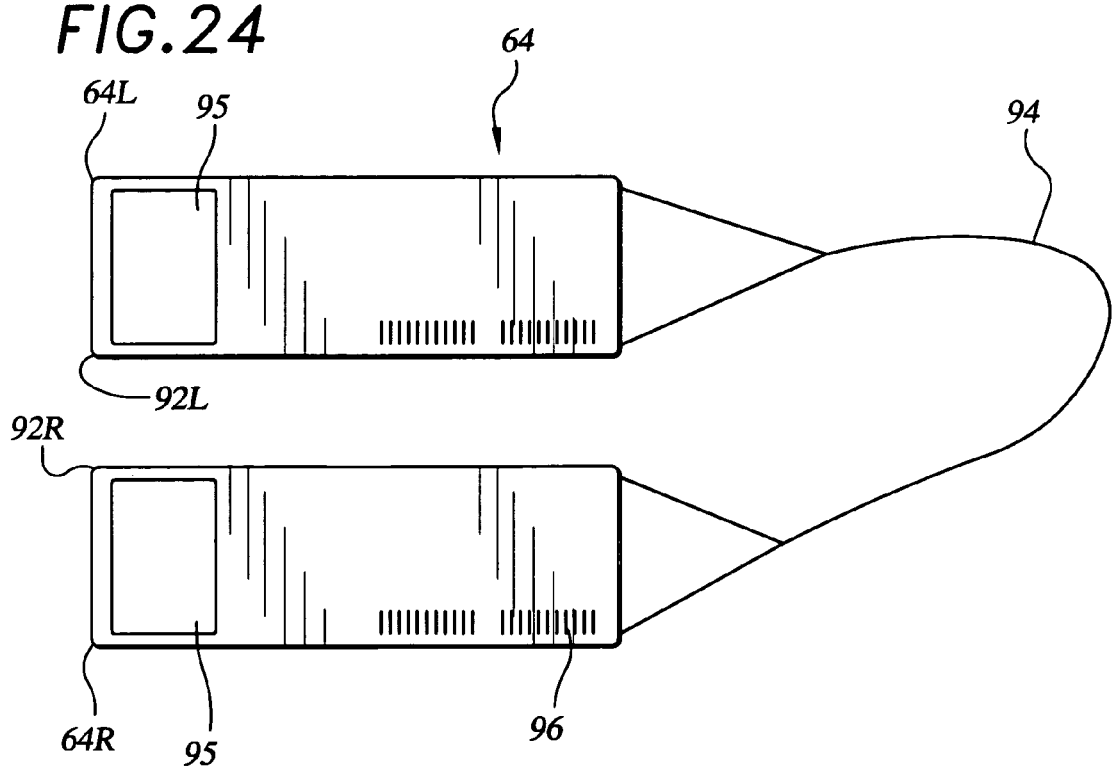
FIG. 24 illustrates an alternative embodiment of the belt.

The compression belt may be provided in several forms. It is preferably made of some tough material such as parachute cloth or Tyvek®. In the most basic form shown in FIG. 23, the belt 64 is a plain band of material with fastening ends 92L and 92R, corresponding left and right belt portions 64L and 64R, and the spool engaging center portion 93. While we have used the spool slot in combination with the belt being threaded through the spool slot as a convenient mechanism to engage the belt in the drive spool, the belt may be fixed to the drive spool in any manner. In FIG. 24, the compression belt is provided in two distinct pieces comprising left and right belt portions 64L and 64R connected with a cable 94 which is threaded through the drive spool. This construction permits a much shorter drive spool, and may eliminate friction within the housing inherent in the full width compression band of FIG. 23. The fastening ends 92L and 92R are fitted with hook and loop fastening elements 95 which may be used as an alternative to other quick release mechanisms. To provide a measurement of belt pay-out and take-up during operation, the belt or cable may be modified with the addition of a linear encoder scale, such as scale 96 on the belt near the spool engaging center portion 93. A corresponding scanner or reader may be installed on the motor box, or in the cartridge in apposition to the encoder scale.

Figure 25:
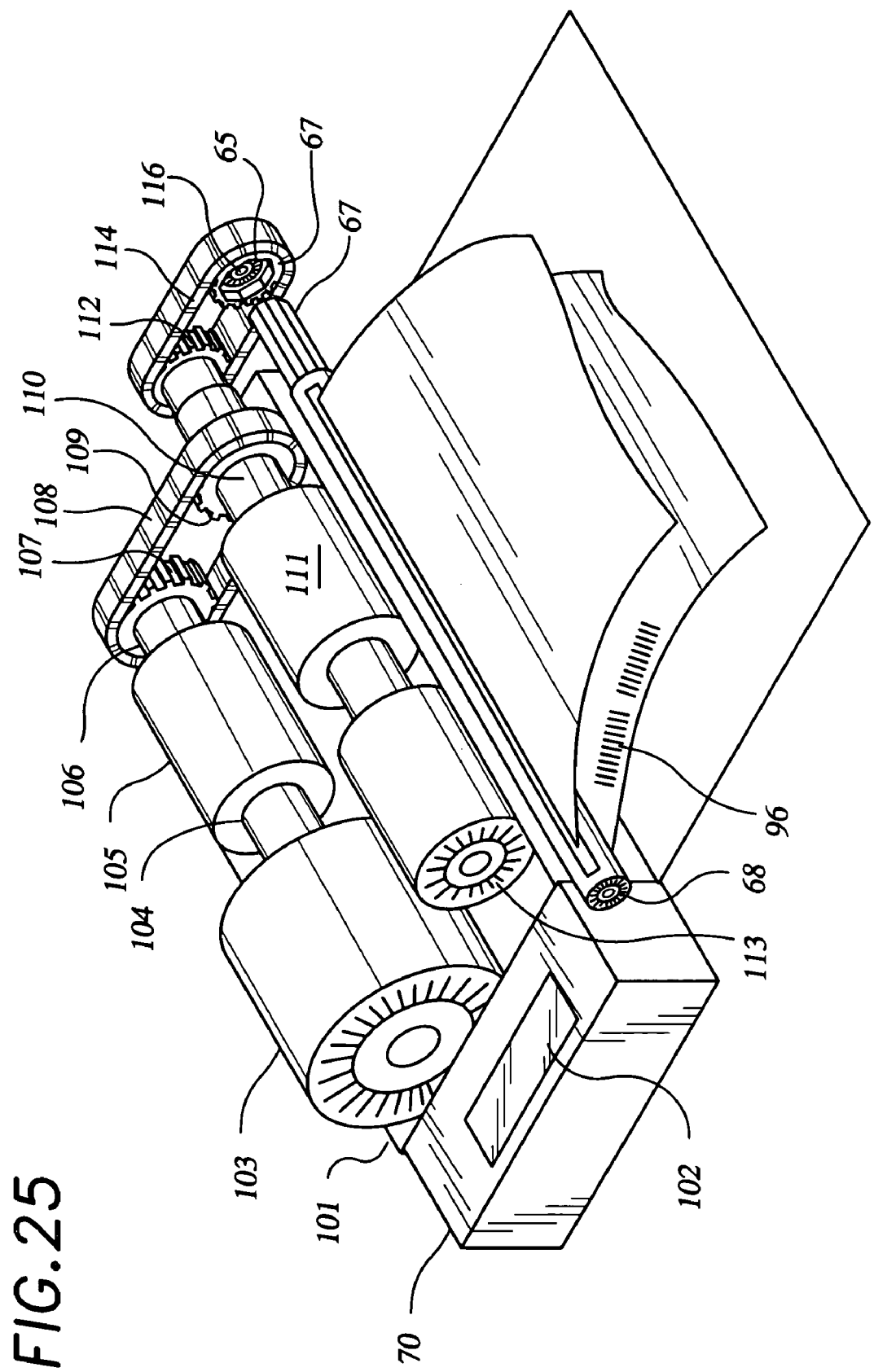
FIG. 25 illustrates the configuration of the motor and clutch within the motor box.

FIG. 25 illustrates the configuration of the motor and clutch within the motor box. The exterior of the motor box includes a housing 101, and a computer module 70 with a convenient display screen 102 for display of any parameters measured by the system. The motor 103 is a typically small battery operated motor which can exert the required belt tensioning torque. The motor shaft 104 is lined up directly to the brake 105 which includes reducing gears and a cam brake to control free spinning of the motor when the motor is not energized (or when a reverse load is applied to the gearbox output shaft). The gearbox output rotor 106 connects to a wheel 107 and chain 108 which connects to the input wheel 109, and thereby to the transmission rotor 110 of the clutch 111. The clutch 111 controls whether the input wheel 109 engages the output wheel 112, and whether rotary input to the input wheel is transmitted to the output wheel. (The secondary brake 113, which we refer to as the secondary brake, provides for control of the system in some embodiments, as explained below in reference to FIG. 32.) The output wheel 112 is connected to the drive wheel 66 via the chain 114 and drive wheel 66 and receiving rod 67 (the drive rod is on the cartridge). The drive wheel 66 has receiving socket 65 which is sized and shaped to mate and engage with the drive rod 67 (simple hexagonal or octagonal sprocket which matches the drive rod is sufficient). While we use a wrap spring brake (a MAC 45 sold by Warner Electric) for the cam brake in the system, any form of brake may be employed. The wrap spring brake has the advantage of allowing free rotation of the shaft when de-energized, and holds only when energized. The wrap spring brake may be operated independent of the motor. While we use chains to transmit power through the system, belts, gears or other mechanisms may be employed.

FIG. 26 illustrates the configuration of the motor and clutch within the motor box. The exterior of the motor box includes a housing 101 which holds the motor 103, which is a typical small battery operated motor which can exert the required belt tensioning torque. The motor shaft 104 is lined up directly to the brake 105 which includes reducing gears and a cam. The gearbox output rotor 106 connects the brake to the output wheel 107 and chain 108 which in turn connects directly to the drive wheel 66 and receiving rod 67. The drive spool 68 is contained within the housing 101. At the end of the drive spool opposite the drive wheel, the brake 115 is directly connected to the drive spool. The belt 64 is threaded through the drive spool slot 69. To protect the belt from rubbing on the motor box, the shield 117 with the long aperture 118 is fastened to the housing so that the aperture lies over the drive spool, allowing the belt to pass through the aperture into the drive spool slot, and return out of the housing. Under the housing, slidably disposed within a channel in the bottom of the housing, a push plate 130 is positioned so that it can slide back and forth relative to the housing. The belt right portion 64R is fitted with a pocket 131 which catches or mates with the right tip 132 of the push plate. The right tip of the push plate is sized and dimensioned to fit within the pocket. By means of this mating mechanism, the belt can be slipped onto the push plate, and with the handle 133 on the left end of the push plate, the push plate together with the right belt portion can be pushed under a patient. The belt includes the encoder scale 96, which can be read with an encoder scanner mounted on or within the housing. In use, the belt right portion is slipped under the patient by fastening it to the push plate and sliding the push plate under the patient. The motor box can then be positioned as desired around the patient (the belt will slip through the drive spool slot to allow adjustment). The belt right portion can then be connected to the belt left portion so that the fastened belt surrounds the patient's chest. In both FIGS. 25 and 26, the motor is mounted in side-by-side relationship with the clutch and with the drive spool. With the side-by-side arrangement of the motor and the spool, the motor may be located to the side of the patient, and need not be placed under the patient, or in interfering position with the shoulders or hips. This also allows a more compact storage arrangement of the device, vis-à-vis an in-line connection between the motor and the spool. A battery is placed within the box or attached to the box as space allows.

During operation, the action of the drive spool and belt draw the device toward the chest, until the shield is in contact with the chest (with the moving belt interposed between the shield and the chest). The shield also serves to protect the patient from any rough movement of the motor box, and help keep a minimum distance between the rotating drive spool and the patient's skin, to avoid pinching the patient or the patient's clothing in the belt as the two sides of the belt are drawn into the housing. As illustrated in FIG. 27, the shield 117 may also include two lengthwise apertures 134 separated by a short distance. With this embodiment of the shield, one side of the belt passes through one aperture and into the drive spool slot, and the other side of the belt exits from the drive spool slot outwardly through the other aperture in the shield. The shield, as shown, has an arcuate transverse cross section (relative to the body on which it is installed). This arcuate shape permits the motor box to lay on the floor during use while a sufficient width of shield extends between the box and the belt. The shield can be made of plastic, polyethylene, PTFE, or other tough material which allows the belt to slide easily. The motor box, may, however, be placed anywhere around the chest of the patient.

A computer module which acts as the system controller is placed within the box, or attached to the box, and is operably connected to the motor, the cam brake, clutch, encoder and other operating parts, as well as biological and physical parameter sensors included in the overall system (blood pressure, blood oxygen, end tidal $CO_2$, body weight, chest circumference, etc. are parameters that can be measured by the system and incorporated into the control system for adjusting compression rates and torque thresholds, or belt pay-out and slack limits). The computer module can also be programmed to handle various ancillary tasks such as display and remote communications, sensor monitoring and feedback monitoring, as illustrated in our prior application Ser. No. 08/922,723.

The computer is programmed (with software or firmware or otherwise) and operated to repeatedly turn the motor and release the clutch to roll the compression belt onto the drive spool (thereby compressing the chest of the patient) and release the drive spool to allow the belt to unroll (thereby allowing the belt and the chest of the patient to expand), and hold the drive spool in a locked or braked condition during periods of each cycle. The computer is programmed to monitor input from various sensors, such as the torque sensor or belt encoders, and adjust operation of the system in response to these sensed parameters by, for example, halting a compression stroke or slipping the clutch (or brake) in response to torque limit or belt travel limits. As indicated below, the operation of the motor box components may be coordinated to provide for a squeeze and hold compression method which prolongs periods of high intrathoracic pressure. The system may be operated in a squeeze and quick release method for more rapid compression cycles and better waveform and flow characteristics in certain situations. The operation of the motor box components may be coordinated to provide for a limited relaxation and compression, to avoid wasting time and battery power to move the belt past compression threshold limits or slack limits. The computer is preferably programmed to monitor two or more sensed parameters to determine an upper threshold for belt compression. By monitoring motor torque as measured by a torque sensor and paid out belt length as determined by a belt encoder, the system can limit the belt take-up with redundant limiting parameters. The redundancy provided by applying two limiting parameters to the system avoids over-compression in the case that a single compression parameter exceed the safe threshold while the system fails to sense and response the threshold by stopping belt take-up.

An angular optical encoder (also referred to as a rotary encoder) may be placed on any rotating part of the system to provide feedback to a motor controller relating to the condition of the compression belt. (The encoder system may be an optical scale coupled to an optical scanner, a magnetic or inductive scale coupled to a magnetic or inductive encoder, a rotating potentiometer, or any one of the several encoder systems available.) The encoder 116, for example, is mounted on the secondary brake 113 (in FIG. 25), and provides an indication of the motor shaft motion to a system controller. An encoder may also be placed on the drive socket 65 or drive wheel 66, the motor 103 and/or motor shaft 104. The system includes a torque sensor (sensing current supply to the motor, for example, or directly sensing torque exerted on the drive spool), and monitors the torque or load on the motor, thereby providing an indication of the force applied to the body. For either or both parameters, a threshold is established, above which further compression is not desired or useful, and if this occurs during the compression of the chest, then the clutch is disengaged. The belt encoder is used by the control system to track the take-up of the belt, and to limit the length of belt which is spooled upon the drive belt.

As illustrated in these embodiments, the drive spool has a small diameter such that several rotations of the drive spool are possible (and generally necessary) to effect resuscitative compression. The drive spool diameter is preferably in the range of 0.5 to 2.5 cm. Thus, rotation of a 2.5 cm diameter spool through 1.5 revolution will be required to effect a nominal change in belt length of 12 cm, and rotation of a 0.5 cm diameter spool through eight revolutions will be required to effect a nominal change in belt length of 12 cm. The multiple rotations of the spool help limit motor overrun after detection of a system feedback or physiologic feedback parameter and subsequent system response in stopping the motor, engaging the brake, disengaging the clutch, etc. so that a small motor overrun will result in a smaller belt overrun. The optimal size of the shaft, and all the shafts in the system, will vary with the choice of other components, and the angular encoders used in the system may be calibrated according to the particular geometry effective at the shaft to which they are attached.

In order to control the amount of thoracic compression (change in circumference) for the cardiac compression device using the encoder, the control system must establish a baseline or zero point for belt take-up. When the belt is tight to the point where any slack has been taken up, the motor will require more current to continue to turn under the load of compressing the chest. This, the expected rapid increase in motor current draw (motor threshold current draw), is measured through a torque sensor (an Amp meter, a voltage divider circuit or the like). This spike in current or voltage is taken as the signal that the belt has been drawn tightly upon the patient and the paid out belt length is an appropriate starting point. The encoder measurement at this point is zeroed within the system (that is, taken as the starting point for belt take-up). The encoder then provides information used by the system to determine the change in length of the belt from this pre-tightened or "pre-tensioned" position. The ability to monitor and control the change in length allows the controller to control the amount of pressure exerted on the patient and the change in volume of the patient by limiting the length of belt take-up during a compression cycle. To aid in the identification of the pre-tensioned belt position, the voltage applied to the motor may be limited during the pre-tensioning, thereby slowing the motor, increasing the torque of the motor, and leading to the higher, more easily recognized current spike or current increase upon meeting the resistance of the body. As alternatives to analyzing motor current or torque applied at some point in the system to determine the pre-tensioned position, the rate of belt take up can be monitored through the position encoders illustrated in the several embodiments, either reading the length of deployed or spooled belt from the belt encoder or reading the position of one of the rotating components (which will be related to belt length by a simple multiple). During slack take up, the rate of belt length change ($\Delta l/\Delta t$) may be monitored and analyzed for abrupt changes or a decrease below a certain rate, which will vary with the particular drive train used.

The expected length of belt take-up for optimum compression is 1 to 6 inches. However, six inches of travel on a thin individual may create an excessive change in thoracic circumference and present the risk of injury from the device. In order to overcome this problem, the system determines the necessary change in belt length required by measuring or using the amount of belt travel required to become taut. Knowing the initial length of the belt and subtracting off the amount required to become taut will provide a measure of the patient's size (chest circumference). The system then relies on predetermined limits or thresholds to the allowable change in circumference for each patient on which it is installed, which can be used to limit the change in volume and pressure applied to the patient. The threshold may change with the initial circumference of the patient so that a smaller patient will receive less of a change in circumference as compared to a larger patient (or vice versa, should experience prove that optimal compression extent of compression is inversely related to chest size). The encoder provides constant feedback as to the state of travel and thus the circumference of the patient at any given time. When the belt take-up reaches the threshold (change in volume), the system controller ends the compression stroke and continues into the next period of hold or release as required by the compression/decompression regimen programmed into the controller. The encoder also enables the system to limit the release of the belt so that it does not fully release. This release point can be determined by the zero point established on the pre-tightening first take-up, or by taking a percentage of the initial circumference or a sliding scale triggered by the initial circumference of the patient.

The belt could also be buckled so that it remains tight against the patient. Requiring the operator to tighten the belt provides for a method to determine the initial circumference of the patient. Again encoders can determine the amount of belt travel and thus can be used to monitor and limit the amount of change in the circumference of the patient given the initial circumference.

Several compression and release patterns may be employed to boost the effectiveness of the CPR compression. Typical CPR compression is accomplished at 60 to 80 cycles per minute, with the cycles constituting mere compression followed by complete release of compressive force. This is the case for manual CPR as well as for known mechanical and pneumatic chest compression devices. With our new system, compression cycles in the range of 20 to 70 cpm have been effective, and the system may be operated as high as 120 cpm or more, This type of compression cycle can be accomplished with the motor box with motor and clutch operation as indicated in FIG. 28. When the system is operating in accordance with the timing table of FIG. 28, the motor is always on, and the clutch cycles between engagement (on) and release (off). After several compressions at time periods T1, T3, T5 and T7, the system pauses for several time periods to allow a brief period (several seconds) to provide a respiration pause, during which operators may provide ventilation or artificial respiration to the patient, or otherwise cause oxygenated air to flow into the patient's lungs. (The brakes illustrated in FIG. 25, are not used in this embodiment, though they may be installed.) The length of the clutch engagement period is controlled in the range of 0 to 2000 msec, and the time between periods of clutch engagement is controlled in the range of 0 to 2000 msec (which, of course, is dictated by medical considerations and may change as more is learned about the optimal rate of compression).

The timing chart of FIG. 28a illustrates the intrathoracic pressure changes caused by the compression belt when operated according to the timing diagram of FIG. 28. The chest compression is indicated by the status line 119. The motor is always on, as indicated by motor status line 120. The clutch is engaged or "on" according to the square wave clutch status line 121 in the lower portion of the diagram. Each time the clutch engages, the belt is tightened around the patient's chest, resulting in a high pressure spike in belt tension and intrathoracic pressure as indicated by the compression status line 119. Pulses p1, p2, p3, p4 and p5 are all similar in amplitude and duration, with the exception of pulse p3. Pulse p3 is limited in duration in this example to show how the torque limit feedback operates to prevent excessive belt compression. (Torque limit may be replaced by belt travel or other parameter as the limiting parameter.) As an example of system response to sensing the torque limit, Pulse p3 is shown rapidly reaching the torque limit set on the motor. When the torque limit is reached, the clutch disengages to prevent injury to the patient and excessive drain on the battery (excessive compression is unlikely to lead to additional blood flow, but will certainly drain the batteries quickly). Note that after clutch disengagement under pulse p3, belt tension and intra-thoracic pressure drop quickly, and the intra-thoracic pressure is increased for only a small portion of cycle. After clutch disengagement based on an over-torque condition, the system returns to the pattern of repeated compressions. Pulse p4 occurs at the next scheduled compression period T7, after which the respiration pause period spanning T8, T9, and T10 is created by maintaining the clutch in the disengaged condition. After the respiration pause, pulse p5 represents the start of the next set of compressions. The system repeatedly performs sets of compressions followed by respiration pauses until interrupted by the operator.

Figures 29, 29A:
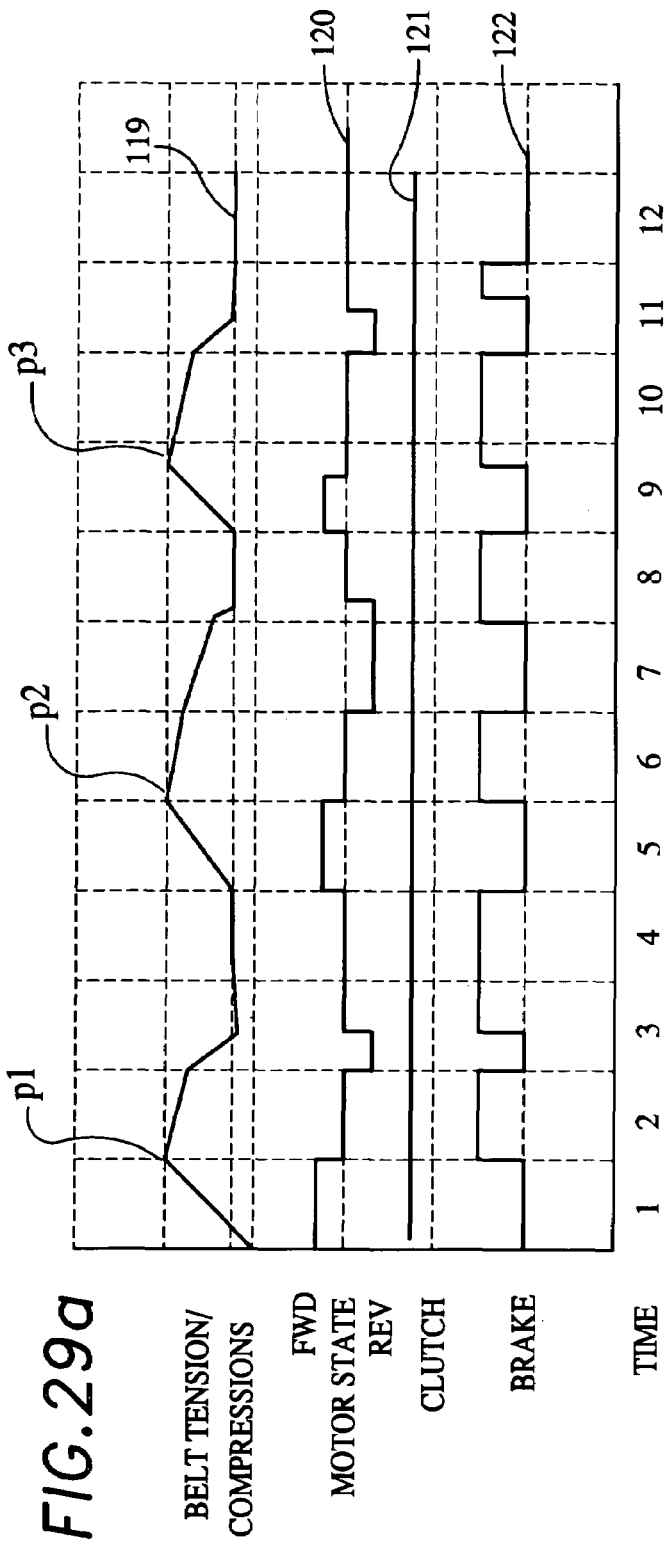
FIG. 29 is a table of the motor and clutch timing in a basic embodiment.
FIG. 29a is a diagram of the pressure changes developed by the system operated according to the timing diagram of FIG. 29.

FIG. 29 illustrates the timing of the motor, clutch and cam brake in a system that allows the belt compression to be reversed by reversing the motor. It also provides for compression hold periods to enhance the hemodynamic effect of the compression periods, and relaxation holds to limit the belt pay-out in the relaxation period to the point where the belt is still taut on the chest and not excessively loose. As the diagram indicates, the motor operates first in the forward direction to tighten the compression belt, then it is turned off for a brief period, then operates in the reverse direction and turns off, and continues to operate through cycles of forward, off, reverse, off, and so on. In parallel with these cycles of the motor state, the cam brake is operating to lock the motor shaft in place, thereby locking the drive spool in place and preventing movement of the compression belt. Brake status line 122 indicates the status of the brake 105. Thus, when the motor tightens the compression belt up to the threshold or time limit, the motor turns off and the cam brake engages to prevent the compression belt from loosening. This effectively prevents relaxation of the patient's chest, maintaining a higher intrathoracic pressure during hold periods T2, T6 and T10. Before the next compression cycle begins, the motor is reversed and the cam brake is disengaged, allowing the system to drive the belt to a looser length and allowing the patient's chest to relax. Upon relaxation to the lower threshold corresponding to the pre-tightened belt length, the cam brake is energized to stop the spool and hold the belt at the pretightened length. The clutch is engaged at all times (the clutch may be omitted altogether if no other compression regimen is desired in the system). (This embodiment may incorporate two motors operating in different directions, connecting to the spool through clutches.)

FIG. 29a illustrates the intrathoracic pressure changes caused by the compression belt when operated according to the timing diagram of FIG. 29. The clutch, if any, is always on as indicated by clutch status line 121. The cam brake is engaged or "on" according to the brake status line 122, which includes the square wave in the lower portion of the diagram. The motor is on, off, or reversed according to motor state line 120. Each time the motor is turned on in the forward direction, the belt is tightened around the patient's chest, resulting in a high pressure spike in belt tension and intrathoracic pressure as shown in the pressure plot line 119. Each time the high threshold limit is sensed by the system, the motor is de-energized, and the cam brake engages to prevent further belt movement. This results in a high maintained pressure or "hold pressure" during the hold periods indicated on the diagram (time period T2, for example). At the end of the hold period, the motor is reversed to drive the belt to a relaxed position, then de-energized. When the motor is turned off after a period of reverse operation, the cam brake engages to prevent excess slacking of the compression belt, which would waste time and battery power. The cam brake disengages when the cycle is reinitiated and the motor is energized to start another compression. Pulses p1, p2, are similar in amplitude and duration. Pulse p3 is limited in duration in this example to show how the torque limit feedback operates to prevent excessive belt compression. Pulse p3 rapidly reaches the torque limit set on the motor (or the take-up limit set on the belt), and the motor stops and the cam brake engages to prevent injury to the patient and excessive drain on the battery. Note that after motor stop and cam brake engagement under pulse p3, belt tension and intra-thoracic pressure are maintained for the same period as all other pulses, and the intra-thoracic pressure is decreased only slightly, if at all, during the high pressure hold period. After pulse, p3, a respiration pause may be initiated in which the belt tension is permitted to go completely slack.

Figures 30, 30A:
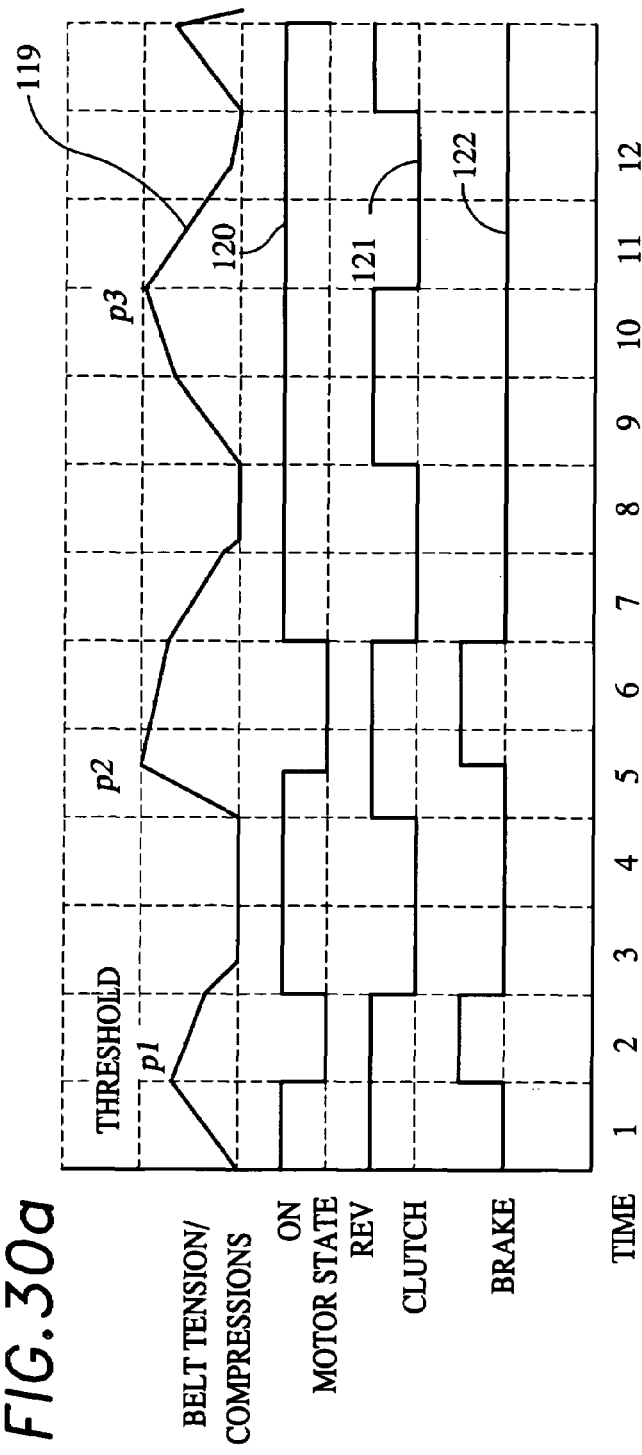
FIG. 30 is a table of the motor and clutch timing for squeeze and hold operation of the compression belt.
FIG. 30a is a diagram of the pressure changes developed by the system operated according to the timing diagram of FIG. 30.

FIG. 30 illustrates the timing of the motor, clutch and cam brake in a system that allows the belt compression to completely relax during each cycle. As the table indicates, the motor operates only in the forward direction to tighten the compression belt, then is turned off for a brief period, and continues to operate through on and off cycles. In the first time period T1, the motor is on and the clutch is engaged, tightening the compression belt about the patient. In the next time period T2, the motor is turned off and the cam brake is energized (with the clutch still engaged) to lock the compression belt in the tightened position. In the next time period T3, the clutch is disengaged to allow the belt to relax and expand with the natural relaxation of the patient's chest. In the next period T4, the motor is energized to come up to speed, while the clutch is disengaged and the cam brake is off. The motor comes up to speed with no effect on the compression belt in this time period. In the next time period, the cycle repeats itself. Thus, when the motor tightens the compression belt up to the threshold or time limit, the motor turns off and the cam brake engages to prevent the compression belt from loosening. This effectively prevents relaxation of the patient's chest, maintaining a higher intrathoracic pressure. Before the next compression cycle begins, the clutch is disengaged, allowing the chest to relax and allowing the motor to come up to speed before coming under load. This provides much more rapid belt compression, leading to a sharper increase in intrathoracic pressure.

FIG. 30a illustrates the intrathoracic pressure changes caused by the compression belt when operated according to the timing table of FIG. 30. The clutch is turned on only after the motor has come up to speed, according to the clutch status line 121 and motor status line 120, which shows that the motor is energized for two time periods before clutch engagement. The cam brake is engaged or "on" according to the brake status line 122 in the lower portion of the diagram. Each time the clutch is engaged, the belt is tightened around the patient's chest, resulting in a sharply increasing high pressure spike in belt tension and intrathoracic pressure as shown in the pressure plot line 119. Each time the motor is de-energized, the cam brake engages and clutch remains engaged to prevent further belt movement, and the clutch prevents relaxation. This results in a high maintained pressure or "hold pressure" during the hold periods indicated on the diagram. At the end of the hold period, the clutch is de-energized to allow the belt to expand to the relaxed position. At the end of the cycle, the cam brake is disengaged (with the clutch disengaged) to allow the motor to come up to speed before initiation of the next compression cycle. The next cycle is initiated when the clutch is engaged. This action produces the sharper pressure increase at the beginning of each cycle, as indicated by the steep curve at the start of each of the pressure Pulses p1, p2, and p3. Again, these pressure pulses are all similar in amplitude and duration, with the exception of pulse p2. Pulse p2 is limited in duration in this example to show how the torque limit feedback operates to prevent excessive belt compression. Pulse p2 rapidly reaches the torque limit set on the motor, and the motor stops and the cam brake engages to prevent injury to the patient and excessive drain on the battery. Note that after motor stop and cam brake engagement under pulse p2, belt tension and intra-thoracic pressure are maintained for the same period as all other pulses, and the intrathoracic pressure is decreased only slightly during the hold period. The operation of the system according to FIG. 30a is controlled to limit belt pressure to a threshold measured by high motor torque (or, correspondingly, belt strain or belt length).

Figures 31, 31A:
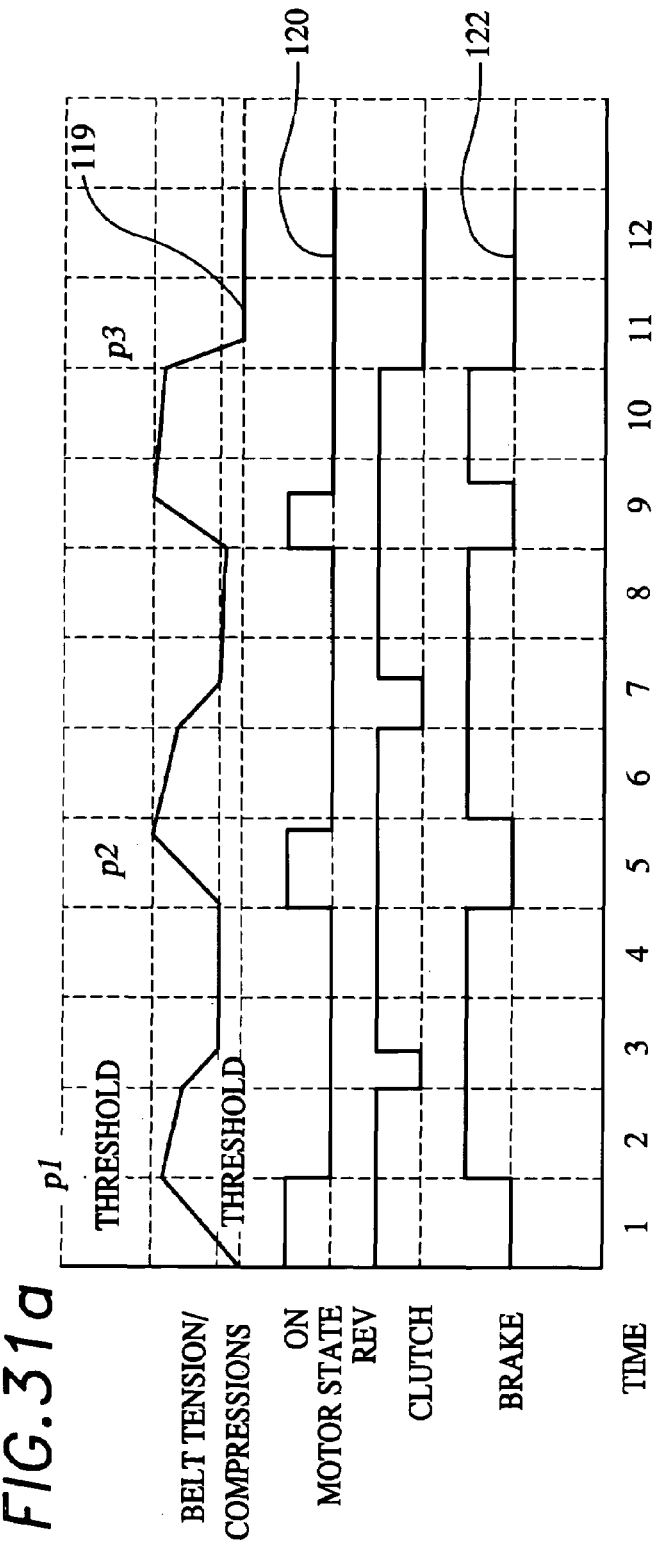
FIG. 31 is a table of the motor and clutch timing for squeeze and hold operation of the compression belt.
FIG. 31a is a diagram of the pressure changes developed by the system operated according to the timing diagram of FIG. 31.

FIG. 31 illustrates the timing of the motor, clutch and cam brake in a system that does not allow the belt compression to completely relax during each cycle. Instead, the system limits belt relaxation to a low threshold of motor torque, belt strain, or belt length. As the table indicates, the motor operates only in the forward direction to tighten the compression belt, then is turned off for a brief period, and continues to operate through on and off cycles. In the first time period T1, the motor is on and the clutch is engaged, tightening the compression belt about the patient. In the next time period T2, the motor is turned off and the cam brake is energized (with the clutch still engaged) to lock the compression belt in the tightened position. In the next time period T3, the clutch is disengaged to allow the belt to relax and expand with the natural relaxation of the patient's chest. The drive spool will rotate to pay out the length of belt necessary to accommodate relaxation of the patient's chest. In the next period T4, while the motor is still off, the clutch is engaged (with the cam brake still on) to prevent the belt from becoming completely slack. To start the next cycle at T5, the motor starts and the cam brake is turned off and another compression cycle begins.

FIG. 31a illustrates the intrathoracic pressure and belt strain that corresponds to the operation of the system according to FIG. 31. Motor status line 120 and the brake status line 122 indicate that when the motor tightens the compression belt up to the high torque threshold or time limit, the motor turns off and the cam brake engages to prevent the compression belt from loosening. Thus the high pressure attained during uptake of the belt is maintained during the hold period starting at T2. When the belt is loosened at T3 by release of the clutch (which uncouples the cam brake), the intrathoracic pressure drops as indicated by the pressure line 119. At T4, after the compression belt has loosened to some degree, but not become totally slack, the clutch engages (and re-couples the cam brake) to hold the belt at some minimum level of belt pressure. This effectively prevents total relaxation of the patient's chest, maintaining a slightly elevated intrathoracic pressure even between compression cycles. A period of low level compression is created within the cycle. Note that after several cycles (four or five cycles) a respiration pause is incorporated into the compression pattern, during which the clutch is off, the cam brake is off to allow for complete relaxation of the belt and the patient's chest. (The system may be operated with the low threshold in effect, and no upper threshold in effect, creating a single low threshold system.) The motor may be energized between compression period, as shown in time periods T11 and T12, to bring it up to speed before the start of the next compression cycle.

Figures 32, 32A:
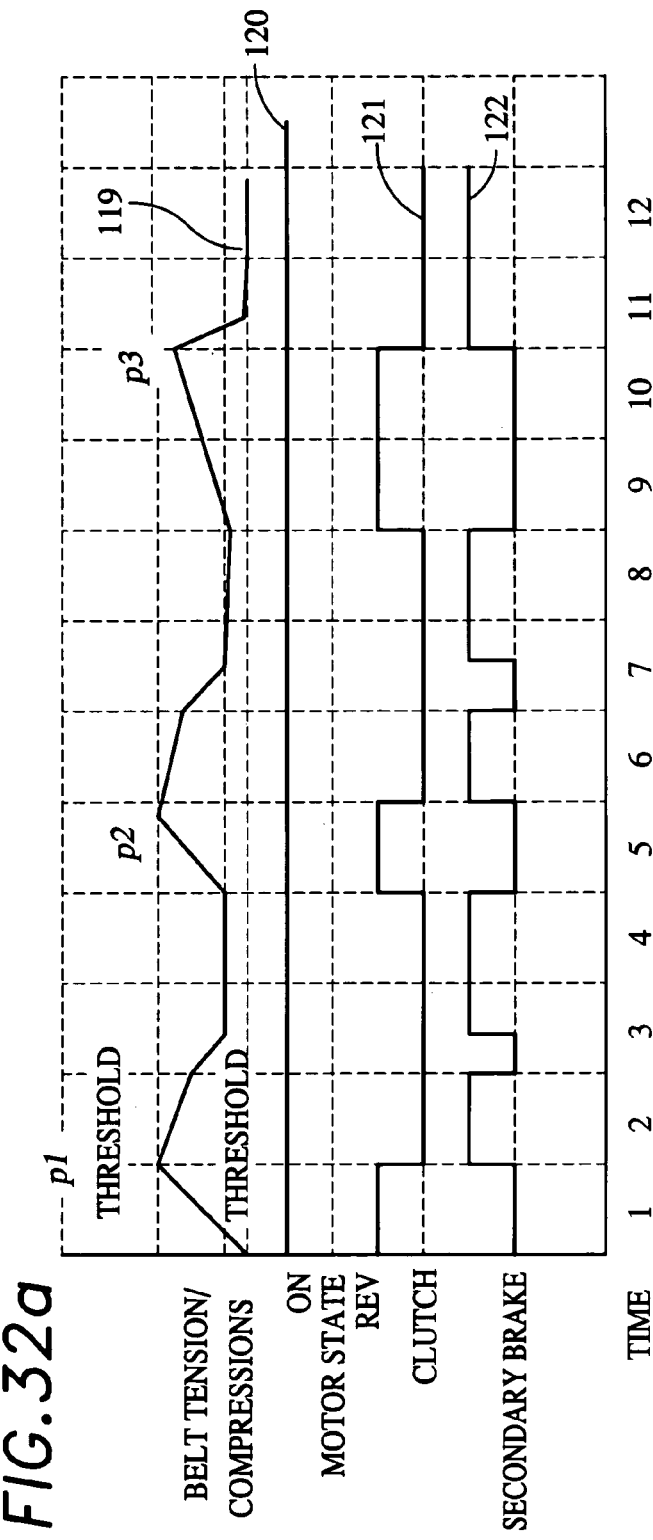
FIG. 32 is a table of the motor and clutch timing for squeeze and hold operation of the compression belt.
FIG. 32a is a diagram of the pressure changes developed by the system operated according to the timing diagram of FIG. 32

FIG. 32 shows a timing table for use in combination with a system that uses the motor, clutch, and secondary brake 113 or a brake on drive wheel or the drive spool itself. The brake 105 is not used in this embodiment of the system (though it may be installed in the motor box). As the motor status line 120 indicates, the motor operates only in the forward direction to tighten the compression belt, and is always on. In the first time period T1, the motor is on and the clutch is engaged, tightening the compression belt about the patient. In the next time period T2, the motor is on but the clutch is disengaged and the brake is energized to lock the compression belt in the tightened position. In the next time period T3, the clutch is disengaged and the brake is off to allow the belt to relax and expand with the natural relaxation of the patient's chest. The drive spool will rotate to pay out the length of belt necessary to accommodate relaxation of the patient's chest. In the next period T4, while the motor is still on, the clutch is disengaged, but energizing the secondary brake is effective to lock the belt prevent the belt from becoming completely slack (in contrast to the systems described above, the operation of the secondary brake is effective when the clutch is disengaged because the secondary brake is downstream of the clutch). To start the next cycle at T5, the motor starts and the secondary brake is turned off, the clutch is engaged and another compression cycle begins. During pulse p3, the clutch is engaged for time periods T11 and T12 while the torque threshold limit is not achieved by the system. This provides an overshoot compression period, which can be interposed amongst the torque limited compression periods.

FIG. 32a illustrates the intrathoracic pressure and belt strain that correspond to the operation of the system according to FIG. 32. Motor status line 120 and the brake status line 122 indicate that when the motor tightens the compression belt up to the high torque threshold or time limit, the secondary brake engages (according to secondary brake status line 122) and the clutch disengages to prevent the compression belt from loosening. Thus the high pressure attained during uptake of the belt is maintained during the hold period starting at T2. When the belt is loosened at T3 by release of the secondary brake, the intrathoracic pressure drops as indicated by the pressure line. At T4, after the compression belt has loosened to some degree, but not become totally slack, the secondary brake engages to hold the belt at some minimum level of belt pressure. This effectively prevents total relaxation of the patient's chest, maintaining a slightly elevated intrathoracic pressure even between compression cycles. A period of low level compression is created within the cycle. At P3, the upper threshold is not achieved but the maximum time allowed for compression is reached, so and the clutch is engaged for two time periods T9 and T10 until the system releases the clutch based on the time limit. At T9 and T10, the secondary brake, though enabled, is not turned on.

Figures 33, 33A:
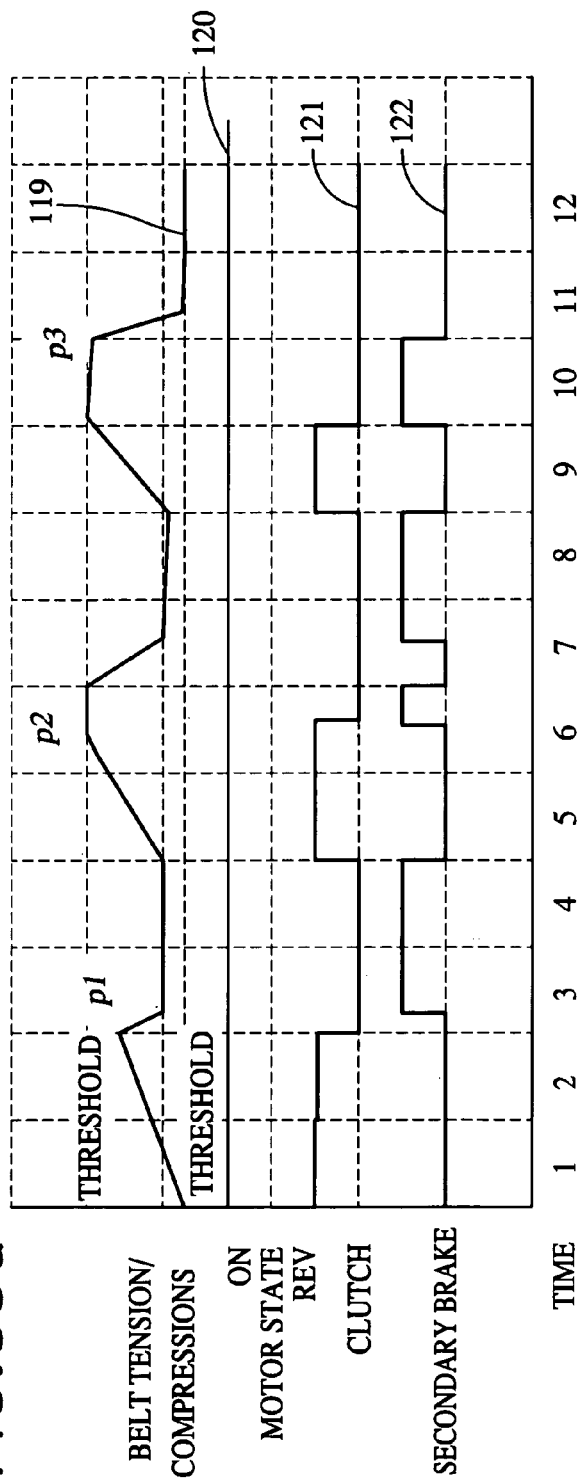
FIG. 33 is a table of the motor and clutch timing for squeeze and hold operation of the compression belt.
FIG. 33a is a diagram of the pressure changes developed by the system operated according to the timing diagram of FIG. 33.

FIG. 33 shows a timing table for use in combination with a system that uses the motor, clutch, and secondary brake 113 or a brake on drive wheel or the drive spool itself. The brake 105 is not used in this embodiment of the system (though it may be installed in the motor box). As the motor status line 120 indicates, the motor operates only in the forward direction to tighten the compression belt, and is always on. In the time periods T1 and T2, the motor is on and the clutch is engaged, tightening the compression belt about the patient. In contrast to the timing chart of FIG. 32, the brake is not energized to hold the belt during the compression periods (T1 and T2) unless the upper threshold is achieved by the system. In the next time period T3, the clutch is disengaged and the brake is off to allow the belt to relax and expand with the natural relaxation of the patient's chest. The drive spool will rotate to pay out the length of belt necessary to accommodate relaxation of the patient's chest. During T3, the belt pays out to the zero point, so the system energizes the secondary brake. During T4, the motor remains on, the clutch is disengaged, and the secondary brake is effective to lock the belt to prevent the belt from becoming completely slack (in contrast to the systems using the cam brake, the operation of the secondary brake is effective when the clutch is disengaged because the secondary brake is downstream of the clutch). To start the next cycle at T5, the motor continues and the secondary brake is turned off, the clutch is engaged and another compression cycle begins. The system achieves the high threshold during time period T6, at peak p2, and causes the clutch to release and the secondary brake to engage, thereby holding the belt tight in the high compression state for the remainder of the compression period (T5 and T6). At the end of the compression period, the brake is momentarily disengaged to allow the belt to expand to the low threshold or zero point, and the brake is engaged again to hold the belt at the low threshold point. Pulse p3 is created with another compression period in which brake is released and the clutch is engaged in T9 and T10, until the threshold is reached, whereupon the clutch disengages and the brake engages to finish the compression period with the belt held in the high compression state. In time periods T11 and T12, the clutch is disengaged and the brake is released to allow the chest to relax completely. This provides for a respiration pause in which the patient may be ventilated.

FIG. 33a illustrates the intrathoracic pressure and belt strain that corresponds to the operation of the system according to FIG. 33. In time periods T1 and T2, the motor status line 120 and the secondary brake status line 122 indicate that the motor tightens the compression belt up to the end of the compression period (the system will not initiate a hold below the upper threshold). When the belt is loosened at T3 by release of the secondary brake, the intrathoracic pressure drops as indicated by the pressure line. At T3, after the compression belt has loosened to some degree, but not become totally slack, the secondary brake engages to hold the belt at some minimum level of belt pressure. This effectively prevents total relaxation of the patient's chest, maintaining a slightly elevated intrathoracic pressure even between compression cycles. A period of low level compression is created within the cycle. Motor status line 120 and the brake status line 122 indicate that when the motor tightens the compression belt up to the high torque threshold or time limit, the secondary brake engages and the clutch disengages to prevent the compression belt from loosening. Thus the high pressure attained during uptake of the belt is maintained during the hold period starting at T6. When the belt is loosened at T7 by release of the secondary brake, the intrathoracic pressure drops as indicated by the pressure line. At T7, after the compression belt has loosened to some degree, but not become totally slack, the secondary brake engages to hold the belt at the lower threshold. At p3, the upper threshold is again achieved, so and the clutch is disengaged and the brake is engaged at time T10 to initiate the high compression hold.

Figures 34, 34A:
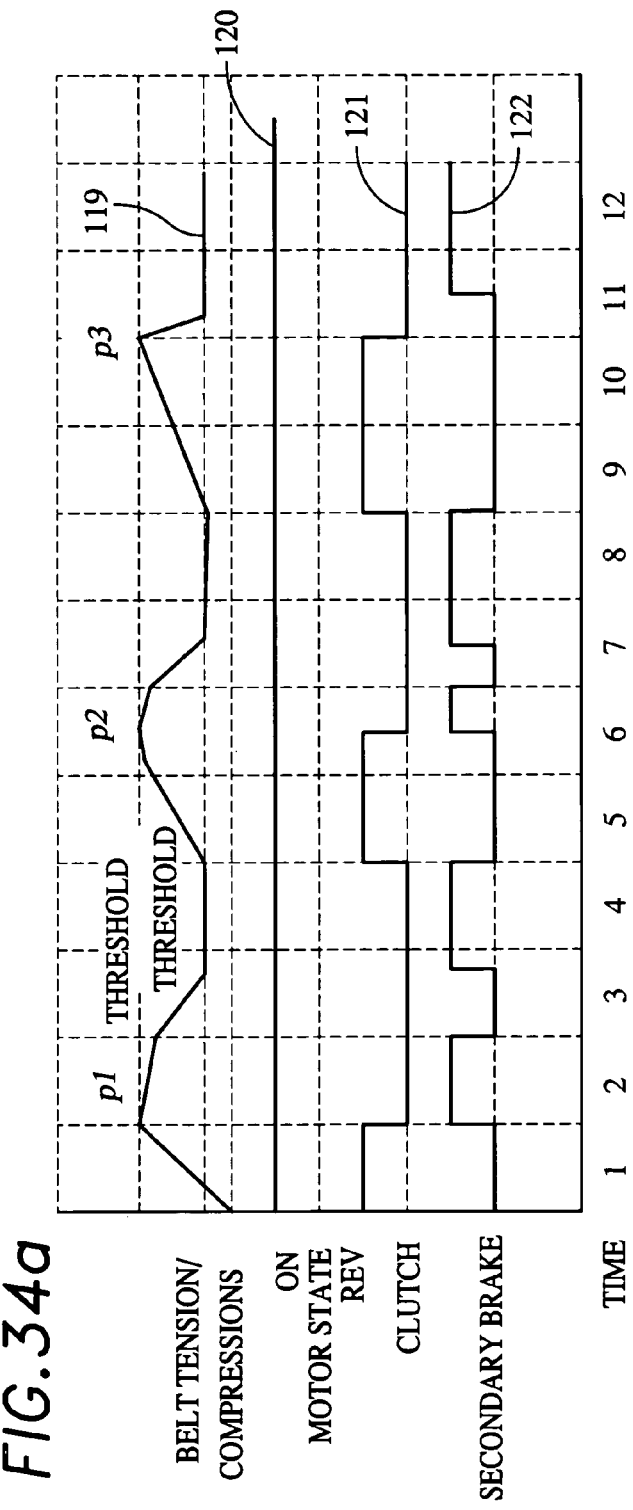
FIG. 34 is a table of the motor and clutch timing for squeeze and hold operation of the compression belt.
FIG. 34a is a diagram of the pressure changes developed by the system operated according to the timing diagram of FIG. 34.

FIG. 34 shows a timing table for use in combination with a system that uses the motor, clutch, and secondary brake 113 or a brake on drive wheel or the drive spool itself. The brake 105 is not used in this embodiment of the system (though it may be installed in the motor box). As the motor status line 120 indicates, the motor operates only in the forward direction to tighten the compression belt, and is always on. In the first time period T1, the motor is on and the clutch is engaged, tightening the compression belt about the patient. In the next time period T2, the motor is on, the clutch is disengaged in response to the sensed threshold, and the brake 113 is enabled and energized to lock the compression belt in the tightened position only if the upper threshold is sensed during the compression period. In the next time period T3, the clutch is disengaged and the brake is off to allow the belt to relax and expand with the natural relaxation of the patient's chest. The drive spool will rotate to pay out the length of belt necessary to accommodate relaxation of the patient's chest. In the next period T4, while the motor is still on, the clutch is disengaged, but energizing the secondary brake is effective to lock the belt preventing the belt from becoming completely slack (in contrast to the systems described above, the operation of the secondary brake is effective when the clutch is disengaged because the secondary brake is downstream of the clutch). To start the next cycle at T5, the motor continues running and the secondary brake is turned off, the clutch is engaged and another compression cycle begins. During pulse p3, the clutch is on in time period T9. The clutch remains engaged and the brake is enabled but not energized in time period T10. The clutch and brake are controlled in response to the threshold, meaning that the system controller is waiting until the high threshold is sensed before switching the system to the hold configuration in which the clutch is released and the brake is energized. In this example, the high threshold is not achieved during compression periods T9 and T10, so the system does not initiate a hold.

FIG. 34*a* illustrates the intrathoracic pressure and belt strain that correspond to the operation of the system according to FIG. 34. Motor status line 120 and the secondary brake status line 122 indicate that when the motor tightens the compression belt up to the high torque threshold or time limit, the clutch disengages and the secondary brake engages to prevent the compression belt from loosening. Thus the high pressure attained during uptake of the belt is maintained during the hold period starting at T2. The period of compression comprises a period of active compressing of the chest followed by a period of static compression. When the belt is loosened at T3 by release of the secondary brake, the intrathoracic pressure drops as indicated by the pressure line 119. At T4, after the compression belt has loosened to some degree, but not become totally slack, the secondary brake engages to hold the belt at some minimum level of belt pressure. This effectively prevents total relaxation of the patient's chest maintaining a slightly elevated intrathoracic pressure between compression cycles. A period of low level compression is created within the cycle. Note that in cycles where the upper threshold is not achieved, the compression period does not include a static compression (hold) period, and the clutch is engaged for two time periods T9 and T10, and the system eventually ends the active compression based on the time limit set by the system.

Figures 35, 35A:
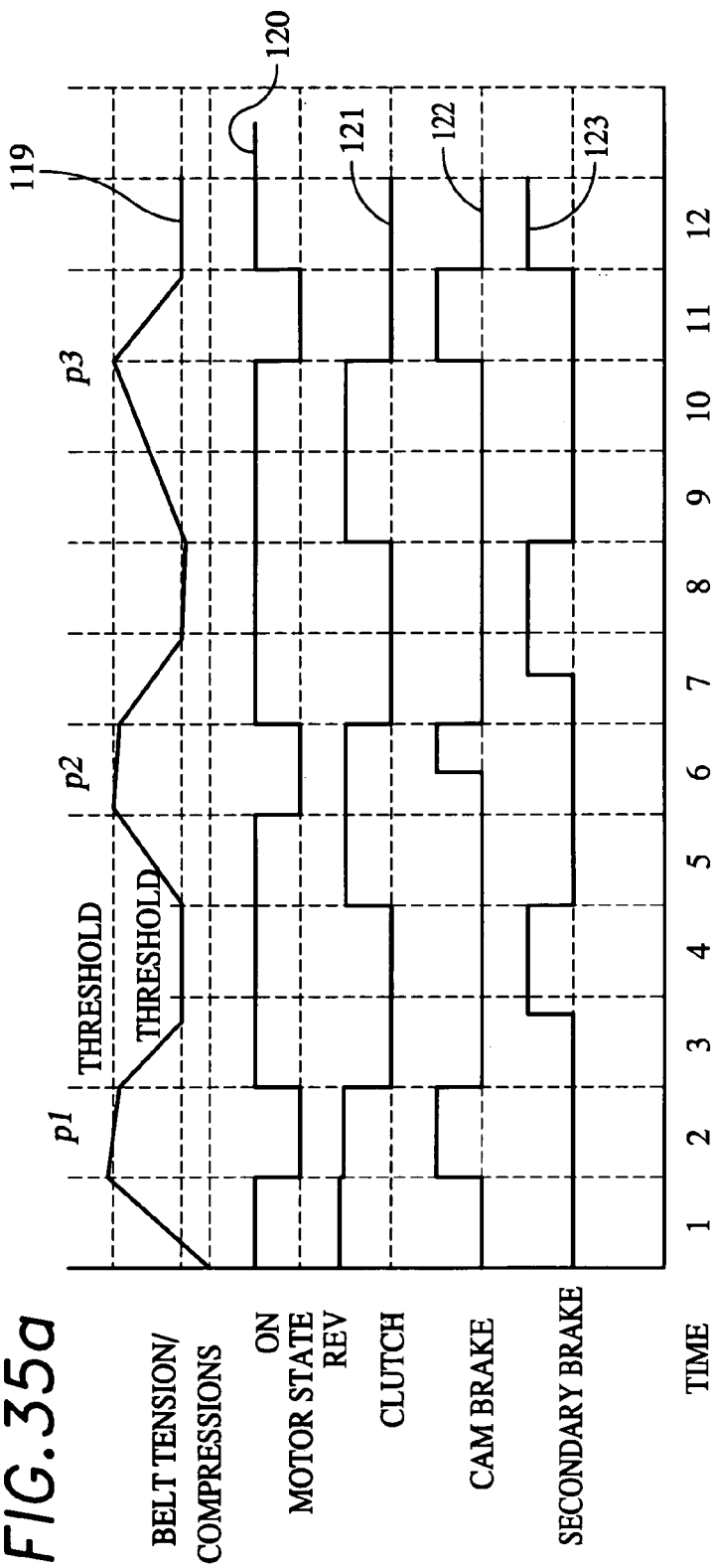
FIG. 35 is a table of the motor and clutch timing for squeeze and hold operation of the compression belt.
FIG. 35a is a diagram of the pressure changes developed by the system operated according to the timing diagram of FIG. 35.

FIG. 35 shows a timing table for use in combination with a system that uses the motor, clutch, the cam brake 105 and a secondary brake 113 (or a brake on drive wheel or the spindle itself). Both brakes are used in this embodiment of the system. As the table indicates, the motor operates only in the forward direction to tighten the compression belt. In the first time period T1, the motor is on and the clutch is engaged, tightening the compression belt about the patient. In the next time period T2, the upper threshold is achieved and the motor is turned off in response to the sensed threshold, the clutch is still engaged, and the cam brake is enabled and energized to lock the compression belt in the tightened position (these events happen only if the upper threshold is sensed during the compression period). In the next time period T3, with the clutch disengaged and the brakes off, the belt relaxes and expands with the natural relaxation of the patient's chest. The drive spool will rotate to pay out the length of belt necessary to accommodate relaxation of the patient's chest. In the next period T4 (while the motor is still on), the clutch remains disengaged, but energizing the secondary brake is effective to lock the belt to prevent the belt from becoming completely slack. To start the next cycle at T5, the secondary brake is turned off, the clutch is engaged and another compression cycle begins (the motor has been energized earlier, in time period T3 or T4, to bring it up to speed). During pulse p3, the clutch is on in time period T9. The clutch remains engaged and the cam brake is enabled but not energized in time period T10. The clutch and cam brake are controlled in response to the threshold, meaning that the system controller is waiting until the high threshold is sensed before switching the system to the hold configuration in which the clutch is released and the cam brake is energized. In this example, the high threshold is not achieved during the compression periods T9 and T10, so the system does not initiate a hold. The cam brake serves to hold the belt in the upper threshold length, and the secondary brake serves to hold the belt in the lower threshold length.

FIG. 35*a* illustrates the intrathoracic pressure and belt strain that corresponds to the operation of the system according to FIG. 35. Motor status line 120 and the cam brake status line 122 indicate that when the motor tightens the compression belt up to the high torque threshold or time limit, the motor turns off and the cam brake engages to prevent the compression belt from loosening (the clutch remains engaged). Thus the high pressure attained during uptake of the belt is maintained during the hold period starting at T2. Thus the period of compression comprises a period of active compressing of the chest followed by a period of static compression. When the belt is loosened at T3 by release of the clutch, the intrathoracic pressure drops as indicated by the pressure line 119. At T4, after the compression belt has loosened to some degree, but not become totally slack, the secondary brake engages to hold the belt at some minimum level of belt pressure, as indicated by the secondary brake status line 123. This effectively prevents total relaxation of the patient's chest, maintaining a slightly elevated intrathoracic pressure even between compression cycles. A period of low level compression is created within the cycle. Note that in cycles where the upper threshold is not achieved, the compression period does not include a static compression (hold) period, and the clutch is engaged for two time periods T9 and T10, and the system eventually ends the active compression based on the time limit set by the system.

The previous figures have illustrated control systems in a time dominant system, even where thresholds are used to limit the active compression stroke. We expect the time dominant system will be preferred to ensure a consistent number of compression periods per minute, as is currently preferred in the ACLS. Time dominance also eliminates the chance of a runaway system, where the might be awaiting indication that a torque or encoder threshold has been met, yet for some reason the system does not approach the threshold. However, it may be advantageous in some systems, perhaps with patients closely attended by medical personnel, to allow the thresholds to dominate partially or completely. An example of partial threshold dominance is indicated in the table of FIG. 36. The compression period is not timed, and ends only when the upper threshold is sensed at point A. The system operates the clutch and brake to allow relaxation to the lower threshold at point B, and then initiates the low threshold hold period. At a set time after the peak compression, a new compression stroke is initiated at point C, and maintained until the peak compression is reached at point D. The actual time spent in the active compression varies depending on how long it takes the system to achieve the threshold. Thus cycle time (a complete period of active compression, release and low threshold hold, until the start of the next compression) varies with each cycle depending on how long it takes the system to achieve the threshold, and the low threshold relaxation period floats accordingly. To avoid extended periods in which the system stalls while awaiting an upper threshold that is never achieved, an outer time limit is imposed on each compression period, as illustrated at point G, where the compression is ended before reaching the maximum allowed compression. In essence, the system clock is reset each time the upper threshold is achieved. The preset time limits 135 for low compression hold periods are shifted leftward on the diagram of FIG. 36a, to floating time limits 136. This approach can be combined with each of the previous control regimens by resetting the timing whenever those systems reach the upper threshold.

The arrangement of the motor, cam brake and clutch may be applied to other systems for belt driven chest compressions. For example, Lach, Resuscitation Method And Apparatus, U.S. Pat. No. 4,770,164 (Sep. 13, 1988) proposes a hand-cranked belt that fits over the chest and two chocks under the patient's chest. The chocks hold the chest in place while the belt is cranked tight. Torque and belt tightness are limited by a mechanical stop which interferes with the rotation of the large drive roller. The mechanical stop merely limits the tightening roll of the spool, and cannot interfere with the unwinding of the spool. A motor is proposed for attachment to the drive rod, and the mate between the motor shaft and the drive roller is a manually operated mechanical interlock referred to as a clutch. This "clutch" is a primitive clutch that must be set by hand before use and cannot be operated during compression cycles. It cannot release the drive roller during a cycle, and it cannot be engaged while the motor is running, or while the device is in operation. Thus application of the brake and clutch arrangements described above to a device such as Lach will be necessary to allow that system to be automated, and to accomplish the squeeze and hold compression pattern.

Lach, Chest Compression Apparatus for Cardiac Arrest, PCT App. PCT/US96/18882 (Jun. 26. 1997) also proposes a compression belt operated by a scissor-like lever system, and proposes driving that system with a motor which reciprocatingly drives the scissor mechanism back and forth to tighten and loosen the belt. Specifically, Lach teaches that failure of full release is detrimental and suggests that one cycle of compression would not start until full release has occurred. This system can also be improved by the application of the clutch and brake systems described above. It appears that these and other belt tensioning means can be improved upon by the brake and clutch system. Lach discloses a number of reciprocating actuators for driving the belt, and requires application of force to these actuators. For example, the scissor mechanism is operated by applying downward force on the handles of the scissor mechanism, and this downward force is converted into belt tightening force by the actuator. By motorizing this operation, the advantages of our clutch and brake system can be obtained with each of the force converters disclosed in Lach. The socketed connection between the motor and drive spool can be replaced with a flexible drive shaft connected to any force converter disclosed in Lach.

Figure 37:
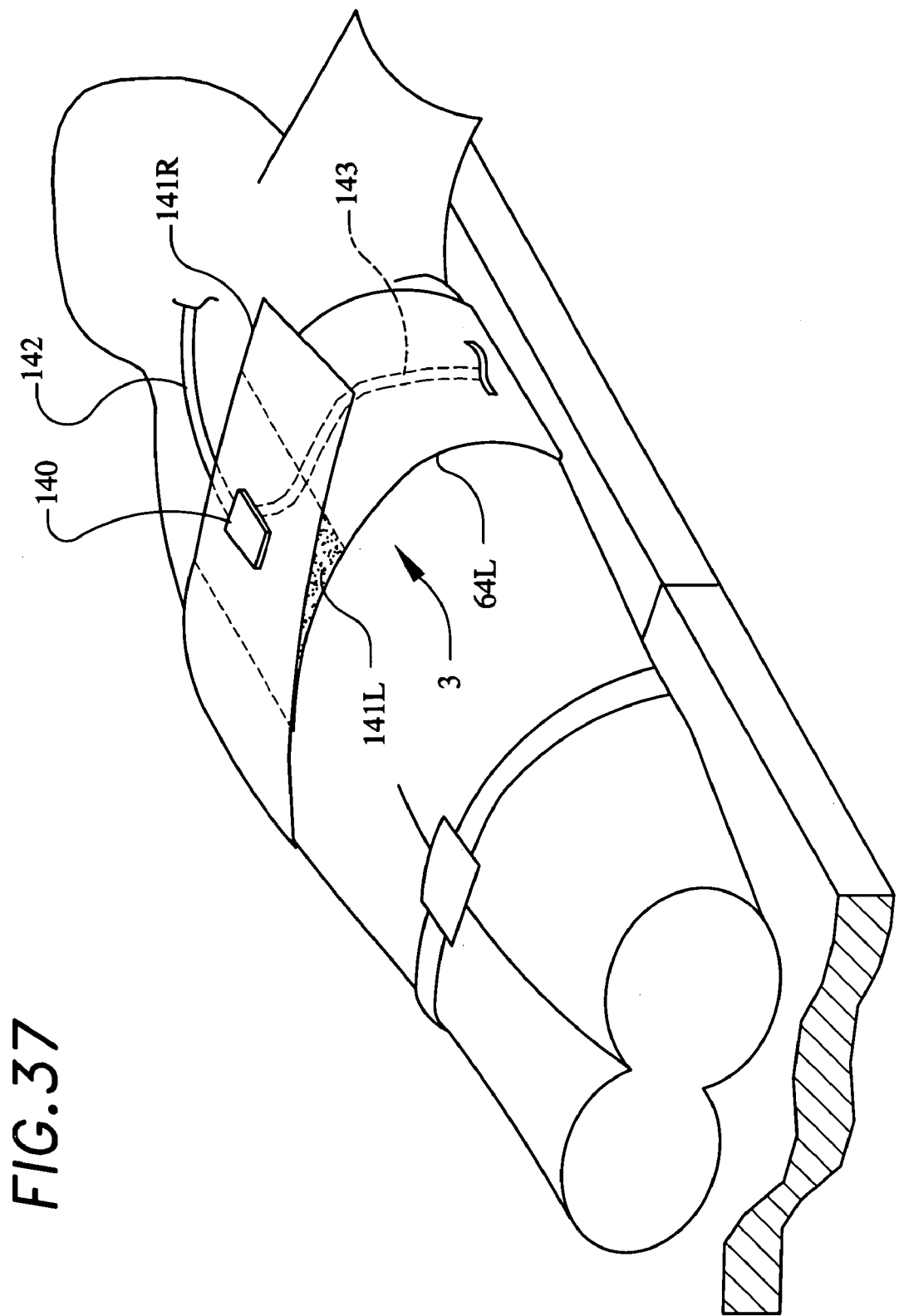
FIG. 37 illustrates an embodiment of the chest compression device with a sternal bladder.

FIG. 37 illustrates an embodiment of the chest compression device with a sternal bladder. The compression belt 3 incorporates an air bladder 140 which, in use, is located on the inner side of the compression vest over the sternum of the patient, and may be of various sizes with a volume of just a few cubic centimeters of air to several hundred cubic centimeters of air, up to about one liter. The compression belt in this case is secured to the body with two overlapping areas 141R and 141L of hook and loop fastener (Velcro®) or other fastener, with the air bladder preferably located over the sternum of the patient. During compression, the bladder itself is also compressed by the belt, and this compression causes an increase in the pressure in the air bladder. A pressure sensor operably connected through a sensing line 142 to the air bladder 140 senses the pressure in the air bladder and transmits a corresponding signal to the controller. Since a sensing line is used, the pressure transducer may be located off the belt and may be placed inside the control box, and the sensing line must then reach from the bladder (under the belt) to the control box. (The pressure sensor may instead be located within the bladder itself, requiring an electrical power and signal transmission cable 143 extending from the bladder to the control box.) The pressure bladder is preferably located on the length of belt on the same side of the patient as the control system (in this case, the left side belt segment 64L) so that the sensing line or electrical cable does not interfere with placement of the belt on the patient. The pressure bladder may be located anywhere on the belt, such as below the patient's spine, but as described below placement over the sternum helps control the compressed shape of the thorax. (Several bladders may be distributed around the thorax to indicate local pressure around the circumference of the thorax. For example, bladders may be located on the lateral surface of the chest, between the chest and the compression belt, in parasaggital locations on the front of the chest, between the chest and the compression belt, and in parasaggital locations between the back and the compression belt (or backboard). With several bladders placed around the chest and connected to pressure transducers, the force profile on an test subject or actual patient may be recorded and compared to blood flow, so that the effect of varying the force profile can be determined.)

The controller may incorporate the pressure signal into its control algorithm by limiting the take-up of the belt so as not to exceed 200–300 mmHg in the air bladder (since the pressure in the air bladder should correspond directly to the pressure exerted on the patients chest) (240 mmHg is currently preferred). The pressure signal may also be used to ensure that pressure in the air bladder, and correspondingly pressure exerted on the patient, reaches a minimum effective pressure of about 240 mmHG in each compression. The air bladder is filled with a volume of air prior to use, and need not be further inflated during storage or use unless it is prone to leakage. The pressure signal may also be used as an indication that the belt has been pre-tensioned, and all slack had been taken up, whereupon the controller can record an encoder reading which is used as the starting point for determining the amount of belt movement that has occurred during a given compression. Currently, pressure of 10 to 50 mmHg in the bladder is used as the pre-tensioned point. While air is our preferred fluid, the bladder may filled with any fluid, gel or other medium capable of transmitting pressure to a pressure sensor, and will operate to provide a pressure sensing volume and/or a shape control volume. When filled with air, the bladder will be slightly compressible and have a variable volume, and when filled with fluid such as water, the bladder will be incompressible and have an essentially fixed volume. Alternate means for sensing pressure or force applied to the body may be used, including pressure transducers, force transducers and force sensing resistors mounted on the belt between the belt and the patient.

FIG. 38 illustrates an embodiment of the chest compression belt with single layer pull straps connecting the belt to the drive spool. The belt is comprised as in previous embodiments with left and right belt portions 64L and 64R and the fastening ends 92L and 92R which are fitted with hook and loop fastening elements 95. The belt left and right belt portions 64L and 64R in this embodiment are joined to two pull straps 144, and may be joined directly to the two pull straps or joined indirectly by intermediate segments of straps 145 and 146. The spool end 147 of the pull straps connects to the drive spool. Each pull strap operates equally on each of the left and right belt segments, eliminating the torque effect of spooling the belt over itself as described in reference to FIGS. 16 through 22.

FIG. 40 illustrates another embodiment of the chest compression belt with single layer pull straps connecting the belt to the drive spool. In this embodiment, the left and right belt portions 64L and 64R of the belt are fixed together at the lower ends corresponding to the spine of the patient, and secured to the straps 144. The lower ends (the ends that join with the pull straps) 148 of each belt portion may be fixed together with stitching, adhesives or other methods. The upper ends 149 (the ends that mate over the sternum) of the belts portions are provided with hook and loop fastener pads.

Figure 41:
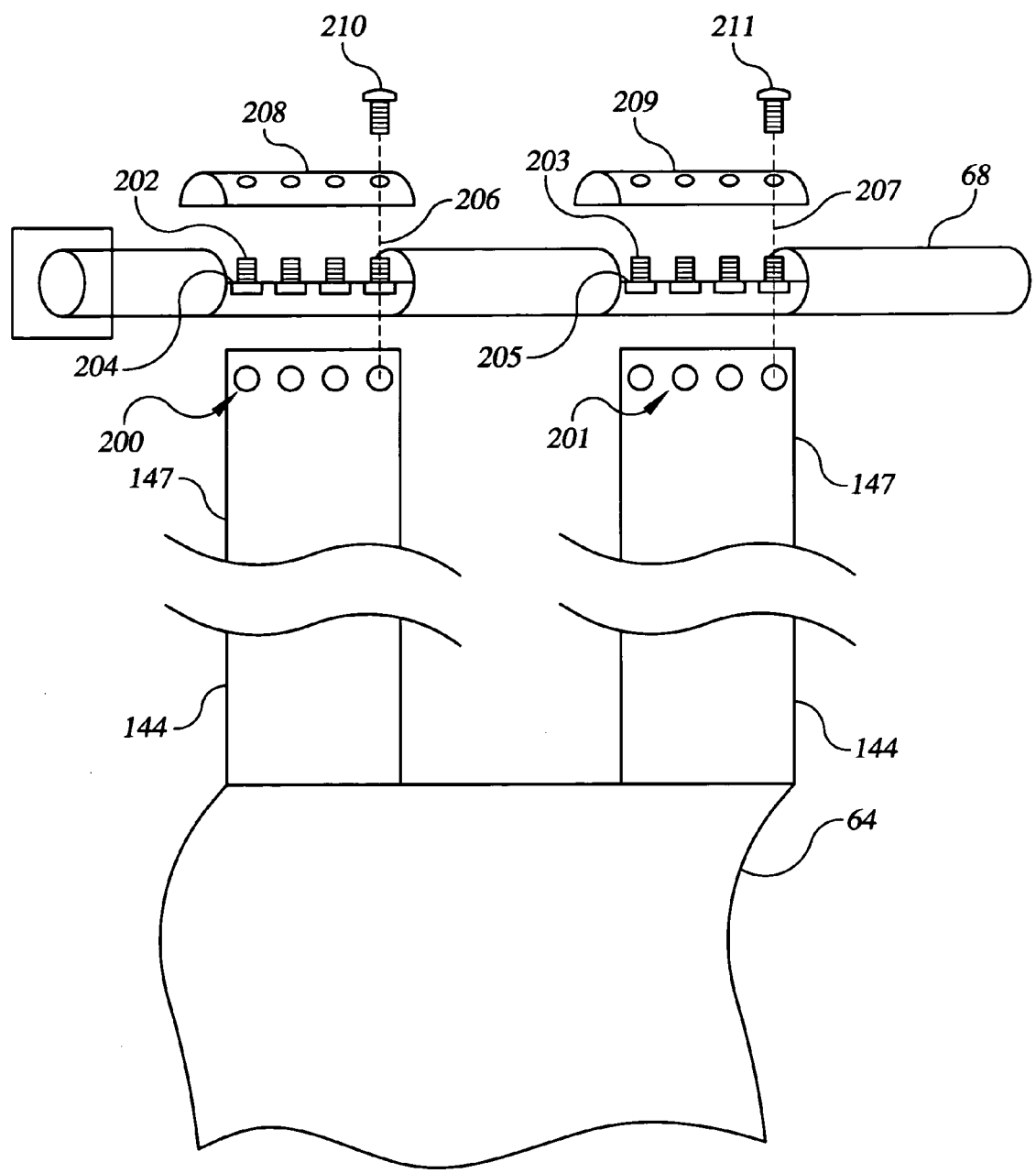
FIG. 41 illustrates a mechanism for connecting the chest compression belt to the drive spool.

The spool end of the pull straps may be attached to the drive spool as illustrated in FIG. 41. The pull straps 144 are secured to the spinal area of the belt by stitching, adhesives, or other method. The spool ends 147 of each pull strap are provided with a set of several grommets or eyelets 200 and 201 for attachment to the matching sets of pins 202 and 203 countersunk in the drive spool 68. As illustrated, the pins are set in the floor of strap receiving recesses 204 and 205. At least one of the pins in each set is an internally or externally threaded pin (206 and 207) capable of receiving a threaded bolt or screw over it. The recess caps 208 and 209 are placed over the strap ends after they are engaged with the posts to secure them in place. The caps may be screwed onto the drive spool and over the strap ends with a screw or internally threaded screws 210 and 211 screwed onto the threaded pins. With this arrangement, installation and replacement of belts is facilitated, and drive spool manufacture is simplified.

The pull straps may be replaced with a single broad segment of the belt which is joined together such that there can be no differential in the spooling of the left and right belt sections upon rotation of the spool. This is illustrated in FIG. 39, where belt 64 is a plain band of material with fastening ends 92L and 92R, corresponding left and right belt portions 64L and 64R, a spool engaging center portion 93. In this embodiment, the left belt and right belt portions of the belt in the spool engaging center portion are stitched together to prevent sliding of one side over the other in the spooling length of the belt, thus preventing uneven take-up of the belt resulting from the different circumferential travel of one side over the other side while spooling on the spool. Thus, FIG. 39 illustrates an embodiment of the chest compression belt with non-torquing spooling segment connecting the belt to the drive spool.

Figure 42:
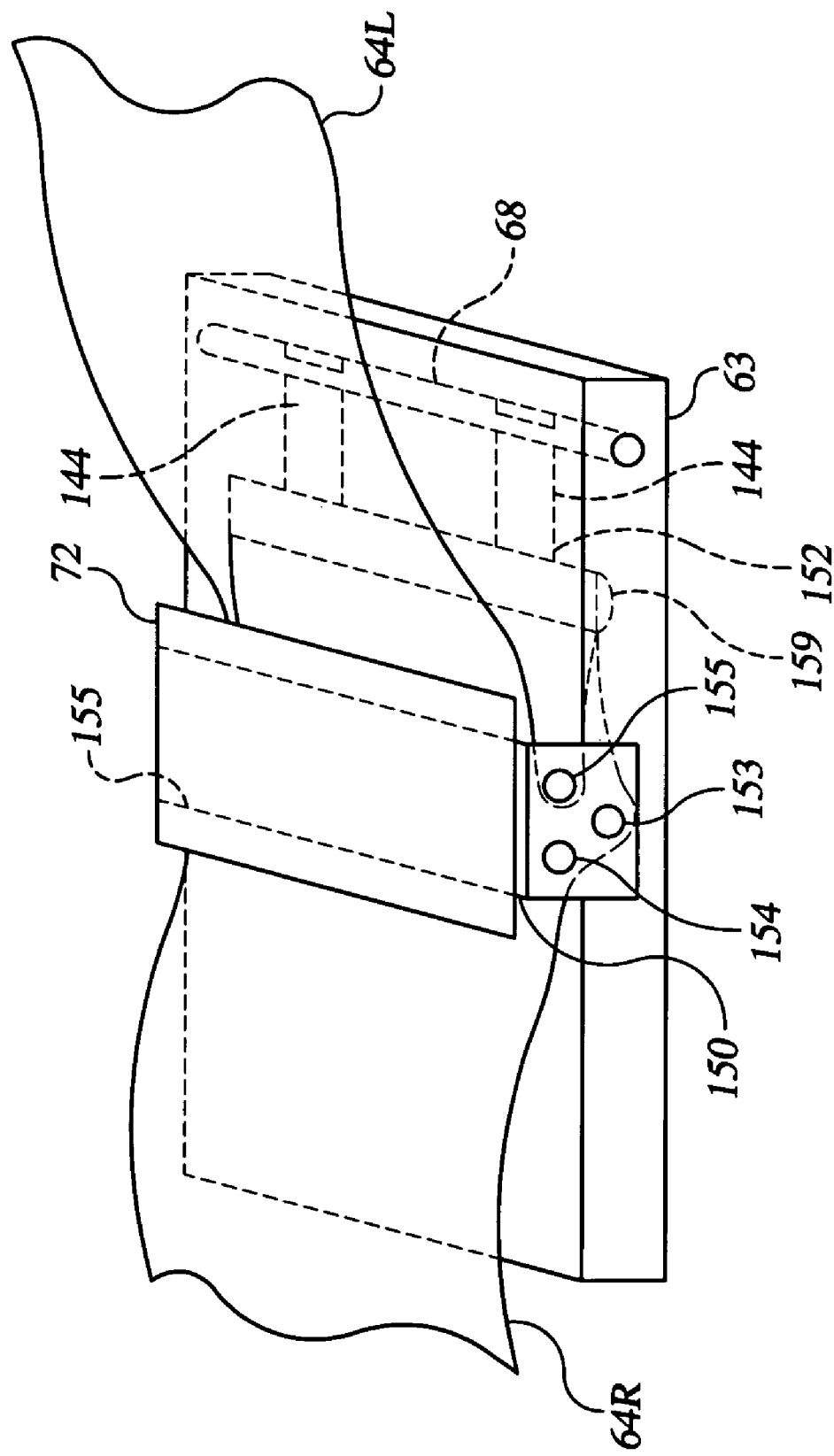
FIG. 42 illustrates an embodiment of the chest compression device with a spinal support plate.

FIG. 42 illustrates an embodiment of the chest compression device with a spinal support plate 150. The compression belt left section 64L and right sections 64R are joined in a seam 151 to pull straps 144 as shown in FIG. 38, and the pull straps are fixed to the drive spool 68 within the cartridge 63. The compression belt right section 64R extends from the pull strap medial end 152 (that is, the end near the medial area of the body, when applied to a patient), under the medially located lower spindle 153 and the slightly lateral upper right spindle 154, under the spinal support platform 150 and further outward to extend under the right flank of the patient when in use. The compression belt left section 64L extends from the pull strap medial end 152 (that is, the end near the medial area of the body, when applied to a patient), reversing direction around the slightly lateral upper left spindle 155, under the spinal support platform 150 and further outward to extend under the left flank of the patient when in use. The spinal support platform 150 extends inferiorly and superiorly (upward and downward) over the cartridge, and serves to support the patient over the cartridge and away from the underlying area in which the belt runs into the cartridge, thus eliminating a large portion of the frictional load which the belt would otherwise have to overcome during operation. The PTFE sheet 72 may be provided on the upper surface of the spinal support platform to reduce friction and rubbing due to chest compression.

Figure 43:
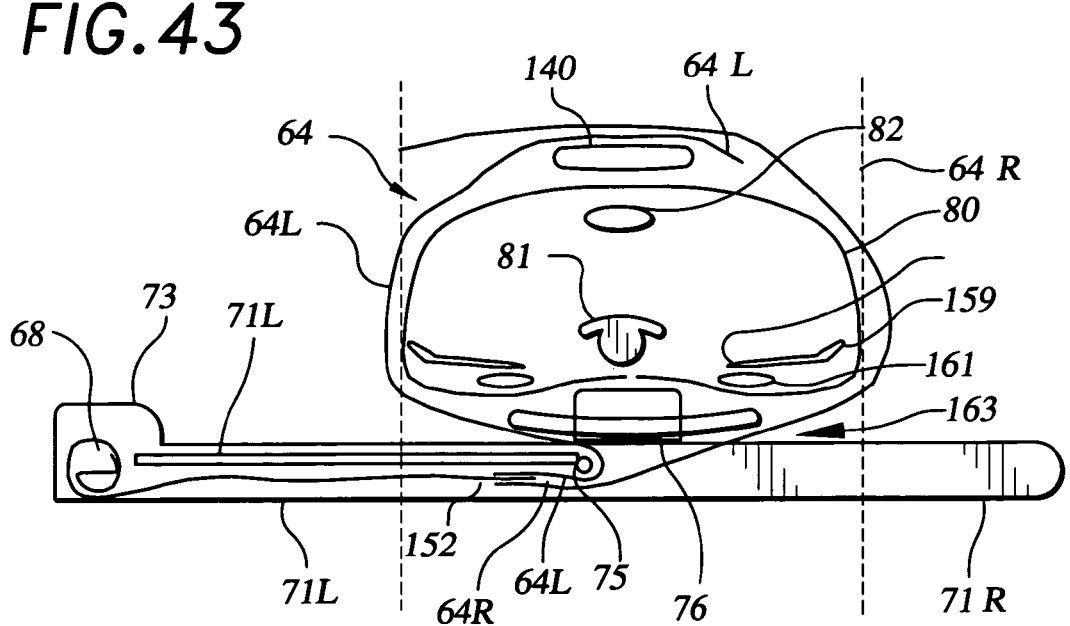
FIG. 43 is a cross section of the chest compression device with a sternal bladder.
Figure 44:
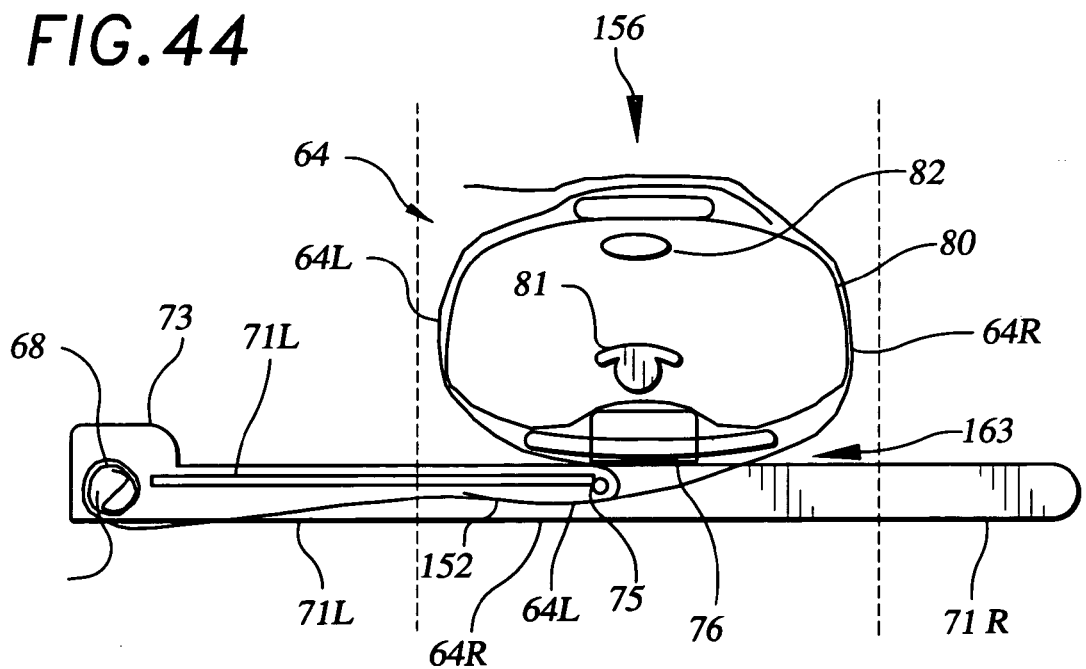
FIG. 44 is a cross section of the chest compression device with a sternal bladder, shown during compression.

FIGS. 43 and 44 illustrate the operation of the compression device when fitted with the features described in FIGS. 37 through 39. As shown in FIG. 43, the compression belt 64 is wrapped around the patient's thorax 80. The bladder 140 is placed between the patient and the left belt portion 64L over the patient's sternum 82 because the motor box and control box are located on the left side of the patient. In this cross section of the device, the connection of the belt to the pull straps is illustrated, with the pull straps 144 connected at their medial end 152 to the left and right belt portions, and connected at their spool end 147 to the drive spool 68 (it can appreciated in this view that the compression belt may be made of a single length of belt, with the pull straps being secured at its midsection, or may be made of two separate lengths of belt secured at their respective medial ends to the pull straps). The connection of the pull straps to the drive spool, rather than direct connection of the belt midsection to the drive spool, results in a uniform pull length (as illustrated in FIG. 44) on each side of the belt, which eliminates the torque on the body resulting from the extra pull length created when spooling two layers of strap or belt over one another, as described in reference to FIGS. 16 and 17. As with previous embodiments, the drive spool rotates through several revolutions, taking up several layers of pull straps, to accomplish the belt tightening in each compression cycle.

Figure 45:
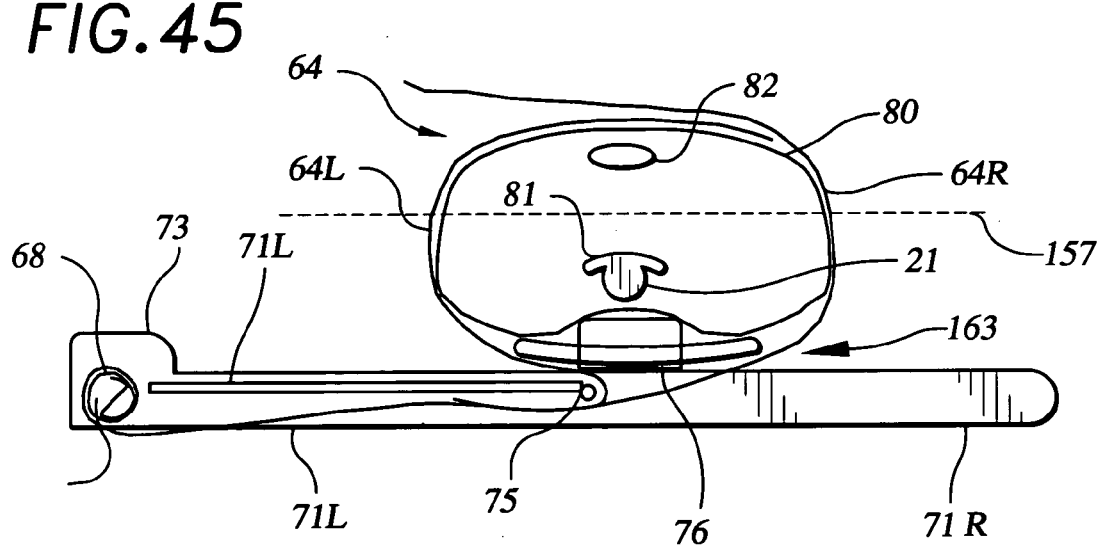
FIG. 45 is a cross section of the chest compression device without a sternal bladder, shown during compression, illustrating a rounding effect that may occur in some patients.

Also shown in FIGS. 43 and 44 is the effect of the fixed bladder on the shape of the thorax after compression. During compression of the patient with the bladder installed between the patient and the belt, the thorax is maintained in a somewhat oval cross section, and is preferentially compressed in the front to back direction (arrow 156). We also refer to this form of compression as anterior-posterior compression or sternal compression, in contrast to the circumferential compression described earlier. The shape of the compressed torso is urged toward a flat ovoid shape, and away from the rounder, more circular shape of the torso which results without the bladder as shown in FIG. 45 (some patients, for unknown reasons, tend to compress more readily from the sides, resulting in the rounder shape in the cross section of the torso). Using the bladder avoids the tendency in some patients to compress into a rounder cross section compressed excessively in the lateral dimension direction (line 157), thus potentially lifting the sternum upwardly. Thus, the physical presence of the bladder, whether or not used for feedback control, is advantageous in the operation of the device. The rounded shape compressions, while useful, are believed to have lower efficiency in terms of the correlation between compression of the chest and compression of the heart and thoracic aorta.

The operation of the spinal support platform 150 can also be seen in FIGS. 43 and 44. The platform extends laterally across the spinal depression 158 which runs up and down the back. The width of the spinal support platform is chosen so that, in most patients, it extends laterally to the shoulder blades (scapula) 159 or medial border of the scapula 160 of the patient, or to the protrusion of the trapezius muscle 161 on either side of the spinal depression of the back (area 158). The platform thus spans the spinal depression, and extends bi-laterally across the spinal depression to the protrusions of the trapezius muscle or the medial border of the shoulder blade. The belt sections 64R and 64L pass under the platform through a vertical gap 163 between the platform and the cartridge or backplate, thereby avoiding running directly between the patient's body and the cartridge for a small lateral width extending slightly beyond the width of the platform.

Figure 46:
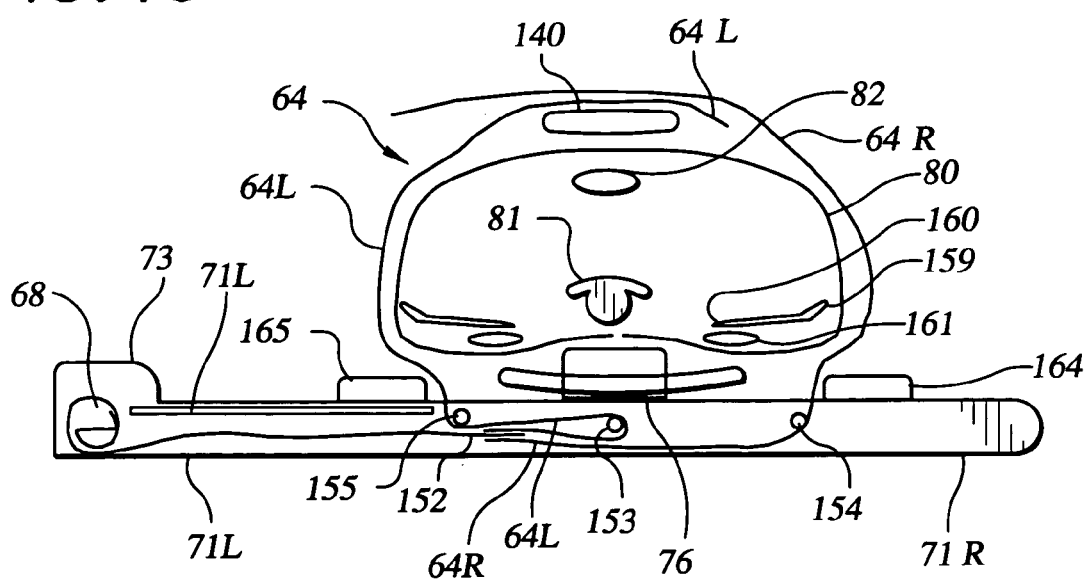
FIG. 46 is a cross section of the chest compression device with the guide spindles laterally spaced from each other to alter the force profile of the compression belt.

FIG. 46 is modification of the device shown in FIG. 42. In this cross section of the chest compression device, the guide spindles 153 (center spindle), 154 (right spindle) and 155 (left spindle) are laterally spaced from each other to alter the force profile of the compression belt. The left and right guide spindles are located farther toward the sides of the patient in this device than they are in FIG. 42, where they are essentially located under the spine. Here, the guide spindles are located several inches laterally of the spine, and lie under the scapula or trapezius region of the patient. This location alters the force profile of the belt, creating a generally anterior to posterior force on the thorax, rather than a circumferentially uniform force profile. The exact location of the guide spindles may be adjusted either further laterally, or medially (back toward the center position immediately under the spine, as in FIG. 42) to increase or decrease the balance between anterior to posterior force and circumferential force applied to the typical patient. The addition of lateral support plates 164 and 165 on the right and left sides of the body provide support for the patient, and also form, with the spinal support plate 150, the gaps through which the belt passes to extend from the cartridge to the patient.

In the embodiment of FIG. 46, sternal displacement is closely related to the spool rotations. Using a spool having a 0.5 inch diameter, and using a light Tyvek® fabric or similar material, with a material thickness of about 0.020 inches, sternal displacement is can be theoretically calculated by the formula:

$$APdisplacement = (0.0314(rev.)^2 + 1.5394(rev.)) - (0.0314(take\text{-}up\ rev.)^2 + 1.5394(take\text{-}up\ rev.))$$

Alternatively, observation of sternal displacement versus spool rotations leads empirically to the formula:

$$APdisplacement(empirical) = (0.0739(rev.)^2 + 1.4389(rev.)) - (0.0739(take\text{-}up\ rev.)^2 + 1.4389(take\text{-}up\ rev.)).$$

In these equations, (rev.) is the total number of revolutions of the spool, as measured by an encoder in the system capable of measuring spool rotations, either directly or indirectly; (take-up rev.) is the number of revolutions required to take up any slack in the belt, according to the methods described above. Either of these equations may be used by the controller of the system to calculate the amount of displacement, either as a back-up to other feed back control methods or as a primary method. In both equations, the controller software keeps track of the take-up revolutions, and the otherwise expected sternal displacement from these revolutions is subtracted from the displacement calculated from the total number of revolutions to provided the actual sternal displacement from a given number of rotations after take-up of slack. The displacement information can be used by the system to inform the system as to the patient's initial height, which can then be correlated to a desired sternal displacement (big people need more compression). Currently, sternal compression of 1 to 2 inches or twenty percent of sternal height is desired. Either of these sternal displacement goals may be met by calculating the sternal displacement as indicated above. Additionally, from the initial take-up, an approximation may be made as to the size of the patient, and this information may be used to determined the desired sternal displacement, and/or adjust other thresholds of the system if desired. For example, knowing the initial length of the entire belt, and subtracting the length spooled during take-up, the length of belt deployed about the patient can be calculated.

Figure 47:
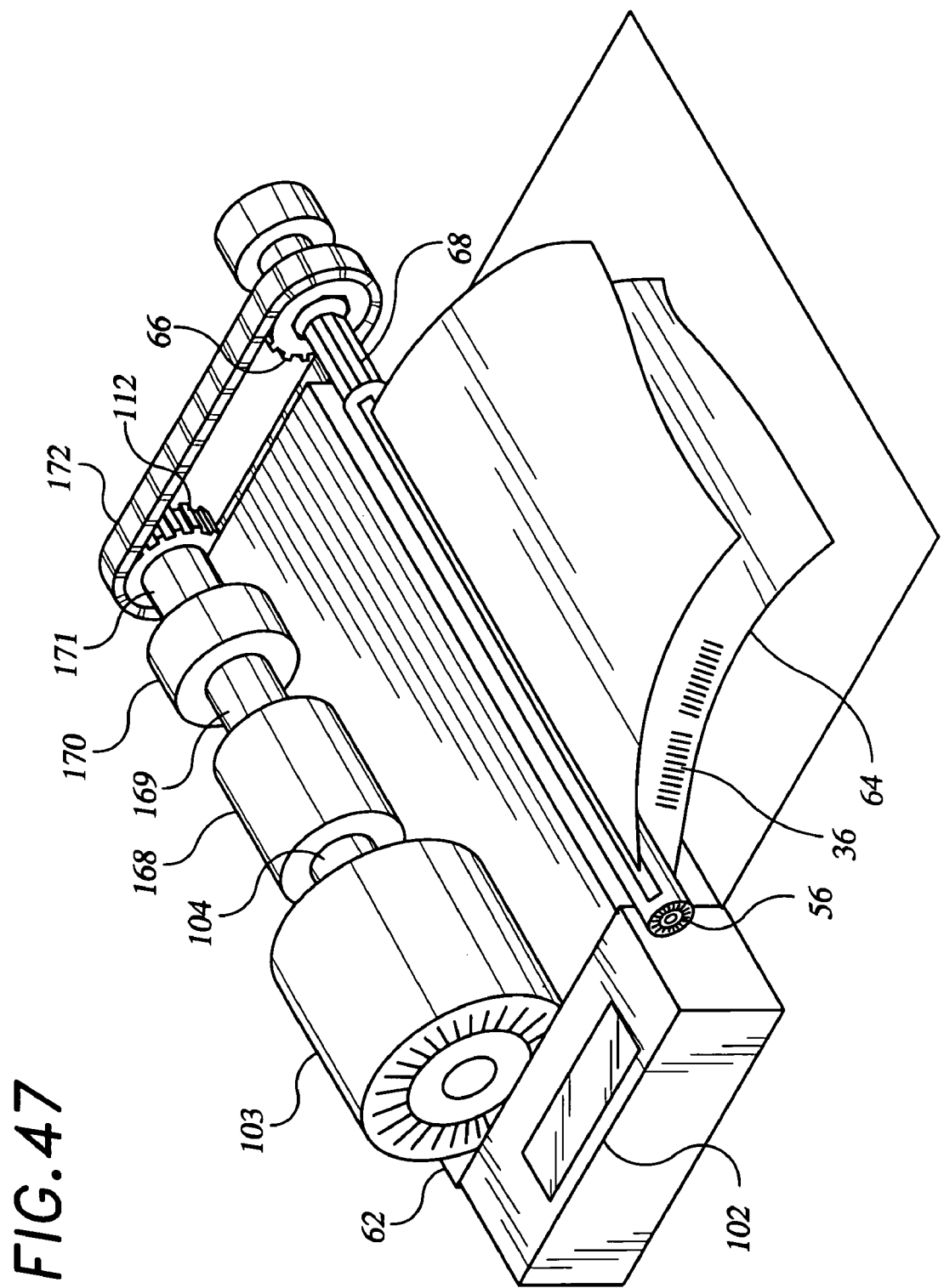
FIG. 47 is a view of the motor box with a no-back reversing drive mechanism.

FIG. 47 shows embodiments of the motor box 62 and the coupling between the motor 103 and the drive spool 68. The drive spool and motor are again aligned in a folded, anti-parallel relationship, so that the motor lies laterally outside the drive spool relative to the patient when in use. The motor output shaft 104 drives reduction gears 168, and the reduction gear output shaft 169 drives a non-reversing coupling 170, and the output shaft 171 of the non-reversing coupling drives the sprocketed output wheel 112. The sprocketed output wheel 112 in turn drives the chain 172 and the sprocketed drive wheel 66 and the drive spool. A non-reversing coupling 170 is interposed in the drive train, for example at the output of the reduction gear (as shown) or at the output of the drive spool sprocket. The non-reversing coupling may be driven in either clockwise or counterclockwise direction when the input shaft is turned by the drive train inputs upstream from the coupling, so that rotation of the input shaft 169 is possible, and results in rotation of the output shaft 171. However, rotation of the output shaft, driven from the downstream side of the drive train (as might occur during chest expansion) is prohibited by internal mechanisms of the coupling, and thus does not reverse power the input shaft.

Several different types of such non-reversing couplings may be used, and are referred to as bi-directional no-back couplings or bi-directional reverse locking couplings. For example, the bi-directional no-back couplings available from Warner Electric incorporates wrap-down springs and interfering tangs. The coupling can be turned only when torque is applied to the input shaft, which may be driven in either direction, but when there is no torque on the input, the output shaft is effectively locked and cannot be rotated in either direction. Any torque applied to the output shaft is transmitted to the clutch body, and will not be transmitted to the input shaft. The bi-directional no-back couplings available from Formsprag Engineering incorporate sprags within the clutch body which interfere with reversing rotation of the output shaft.

Figure 48:
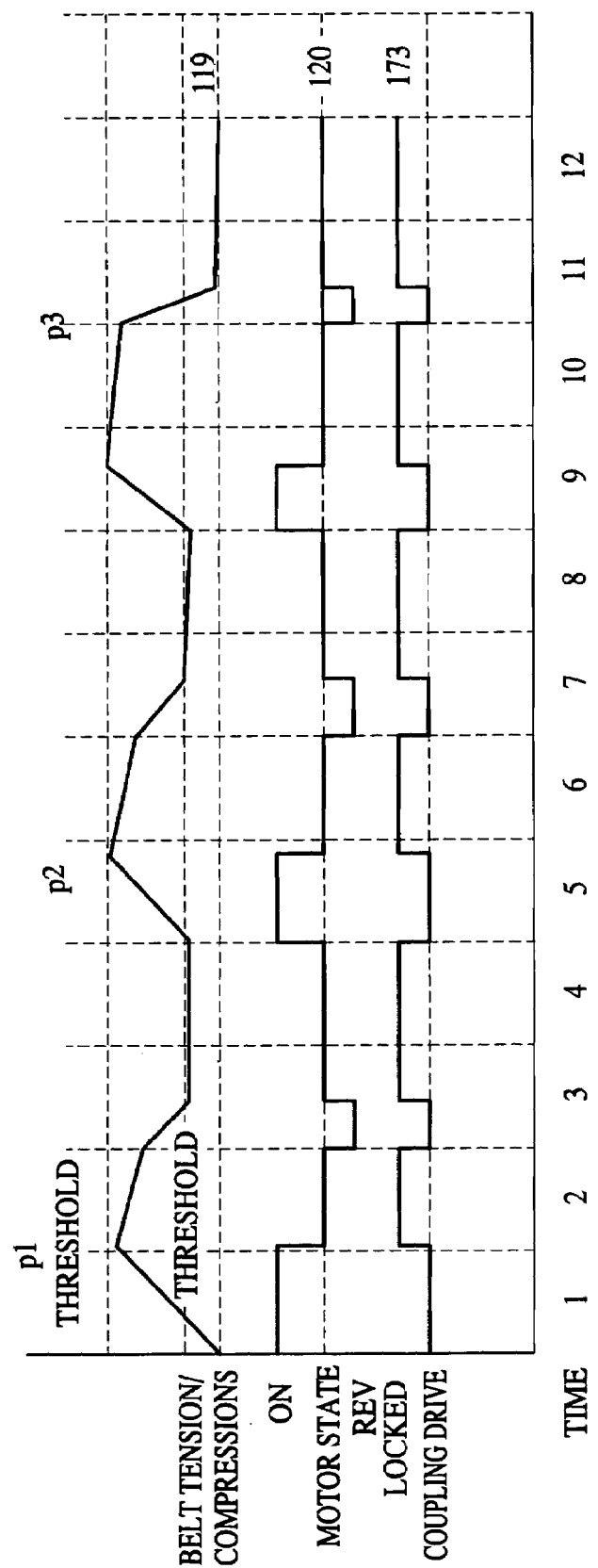
FIG. 48 is a table of the motor box with a no-back reversing drive mechanism.

The bi-directional no-back coupling installed in the drive train may be used instead of the clutches and brakes described in relation to FIG. 25. In operation, the braking and clutching action is replaced by the reverse locking function of the coupling. As shown in FIG. 48, the timing of the system operation is greatly simplified. During each compression stroke, the motor is operated in the tightening direction until the desired feedback limit is reached. The motor is then stopped. The upper level hold is achieved automatically by the reverse locking behavior of the coupling. At the end of the hold period, the motor is operated in reverse, in the loosening direction, whereupon the coupling automatically unlocks and permits loosening rotation. If a lower threshold hold period is desired, the motor is stopped, whereupon continued loosening rotation of the drive spool is prohibited by the reverse-locking behavior of the coupling. The motor may be stopped in the loosening direction in response to feedback based on belt length (from the belt encoders), the pressure in the air bladder, torque on the motor, or other feedback indicating that the low threshold belt position has been reached. Ventilation pauses in which the belt is completely loosened may be interposed between sets of compressions by driving the motor in the loosening direction well past the low threshold. The final position of the belt in the ventilation pause may be determined by from the encoders, from the pressure in the bladder, or other feedback.

FIG. 48 illustrates the intrathoracic pressure and belt strain that corresponds to the operation of the system which uses a non-reversing coupling. Motor status line 120 and the non-reversing coupling line 173 indicate that when the motor is operating to tighten the compression belt up to the high torque threshold or time limit, the non-reversing coupling is driven by the motor. When the motor turns off, the non-reversing coupling locks to prevent the compression belt from loosening. The coupling locks to prevent reversing without any input from the controller. Thus the high pressure attained during uptake of the belt is maintained during the hold period starting at T2. When the belt is loosened at T3 by operating the motor in reverse or loosening direction, with inherent release of the internal locking mechanisms of the non-reversing coupling, and the intrathoracic pressure drops as indicated by the compression status line 119. At T4, after the compression belt has loosened to some degree, but not become totally slack, the motor is stopped, and the non-reversing coupling locks (again without any input or control signal from the controller) to hold the belt at some minimum level of belt pressure. This effectively prevents total relaxation of the patient's chest, maintaining a slightly elevated intra thoracic pressure even between compression cycles. A period of low level compression is created within the cycle. Note that after several cycles (four or five cycles) a respiration pause is incorporated into the compression pattern, for which the motor is driven in reverse to loosen the belt for complete relaxation of the belt and the patient's chest. As with previously described embodiments of the motor box and controller, the system may be operated with the low threshold in effect, and no upper threshold in effect, or with an upper threshold in effect with no lower threshold in effect. It will be noted in the description that reverse operation of the motor refers to operation of the motor in the loosening operation, as compared to forward operation which refers to operation of the motor in the tightening direction. In contrast, when speaking of the non-reversing coupling, reversing refers to reverse-powering the coupling by turning the output shaft to cause rotation of the input shaft. Thus, although the non-reversing coupling will not allow reverse powering, it can rotate in the forward and reverse, clockwise or counterclockwise, and loosening or tightening directions, as those terms are used in reference to the motor.

Thus far, we have described the use of pressure feedback control, belt length or volume feedback control, and motor torque control. It appears from our experience that pressure and thoracic volume are related in such a manner that compression cycles may be controlled with feedback regarding the relationship between the measured volume and the sensed pressure. Thus, the control of the motor, clutch, brake and other components of the drive train may be controlled as a function of the relationship between the force applied to the body and change in the length of the belt. The pressure applied to the thorax is measured, as indicated above, by measuring the pressure in the air bladder illustrated in FIG. 37, or with pressure transducers, force transducers or other means for sensing force applied to the body Torque sensors operably connected to the belt through by connection at any point in the drive train or by sensing motor current, may also be used to sense the force applied to the body The length is measured by scanning the belt encoder or scanning rotary encoders in the drive train, as described above (any other mechanism for measuring belt length may be used). The volume is computed using belt length as a proxy for circumference of the chest, and assuming a circular cross section of the chest. The change in volume is computed based on an 20 cm wide belt and assuming a chest with a circular cross section, and the volume encompassed by the belt is equal to the belt length times the belt width, so that the change in volume is computed as $\Delta v = \Delta$ (cross section)$\times$ 20 cm. The change in belt length is measures through an encoder placed in one of several places in the system as described above.

Figure 49:
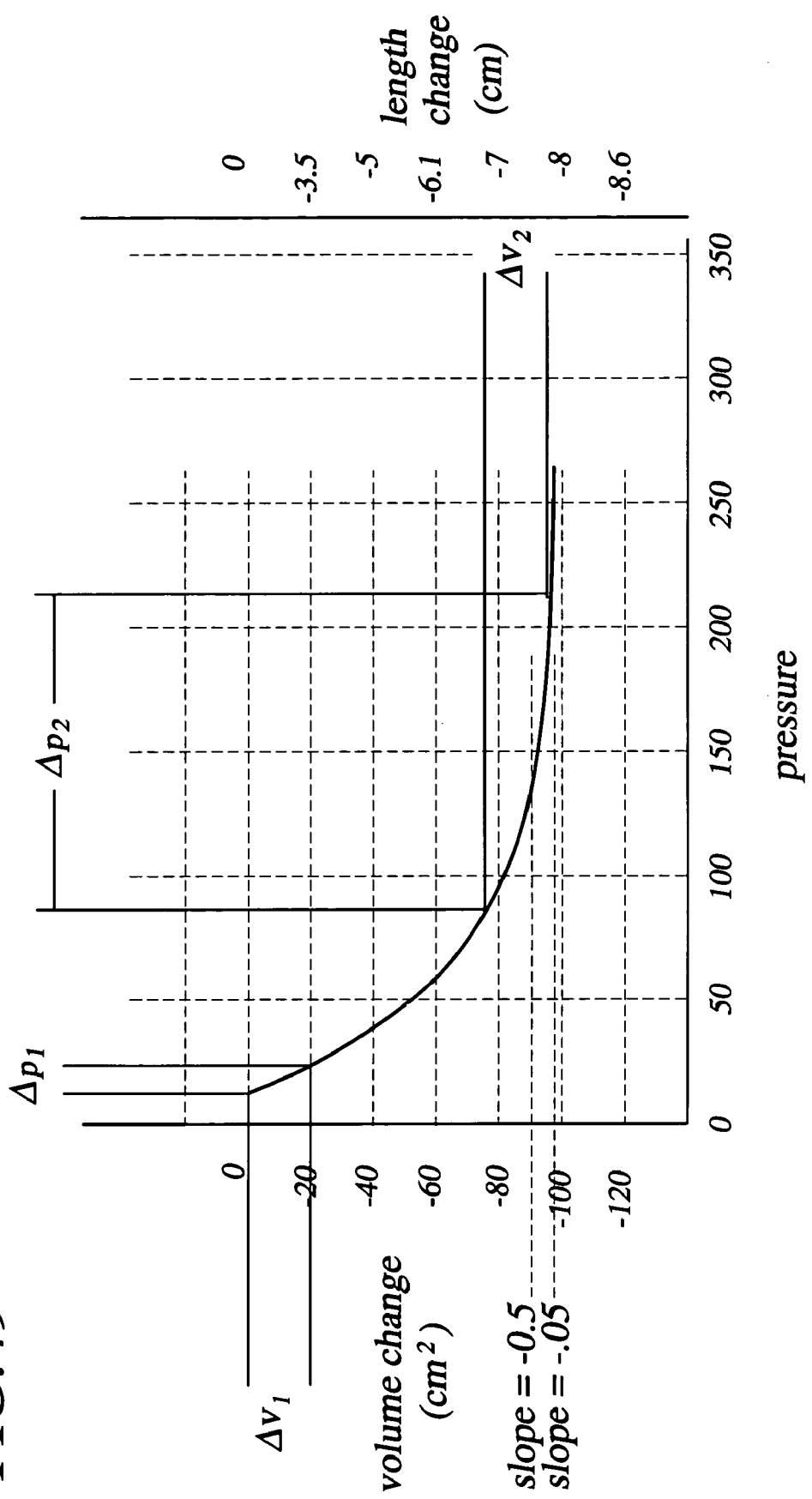
FIG. 49 illustrates the relationship between the change in thoracic volume versus the change in thoracic pressure.

FIG. 49 illustrates the relationship between the change in thoracic volume compression (or change in belt length) versus the thoracic pressure. As illustrated in the graph, an initial large negative change in volume $\Delta v_1$ (large increments of compression) causes a small change in thoracic pressure $\Delta p_1$, while the same volume change $\Delta v_2$ near the end of the compression results in a large increase in pressure $\Delta p_2$. Conversely, large changes in pressure are required to produce small changes in volume at the end of the compression. This is an asymptotic curve with a slope approaching zero. When little or no volume change results from an incremental change in pressure, further efforts by the system to compress the chest are wasteful of battery power, and can be avoided. Thus, the control system is programmed to monitor inputs corresponding to thoracic volume (deployed belt length or other proxy) and thoracic pressure (bladder pressure or other proxy), and limit motor operation by ending a compression when the ratio of volume change versus pressure change (the slope of the curve in FIG. 49) falls below a preset value. Currently, the preset value is experimentally determined to be in the range of 0.05 to 0.5 cm²/mmhg. Correspondingly, if belt length is used as the basis for calculation, the control system is programmed to monitor inputs corresponding to deployed belt length and thoracic pressure (bladder pressure or other proxy), and limit motor operation by ending a compression when the ratio of belt length change versus pressure change (the slope of the curve in FIG. 49 falls below a preset value.

Figure 50:
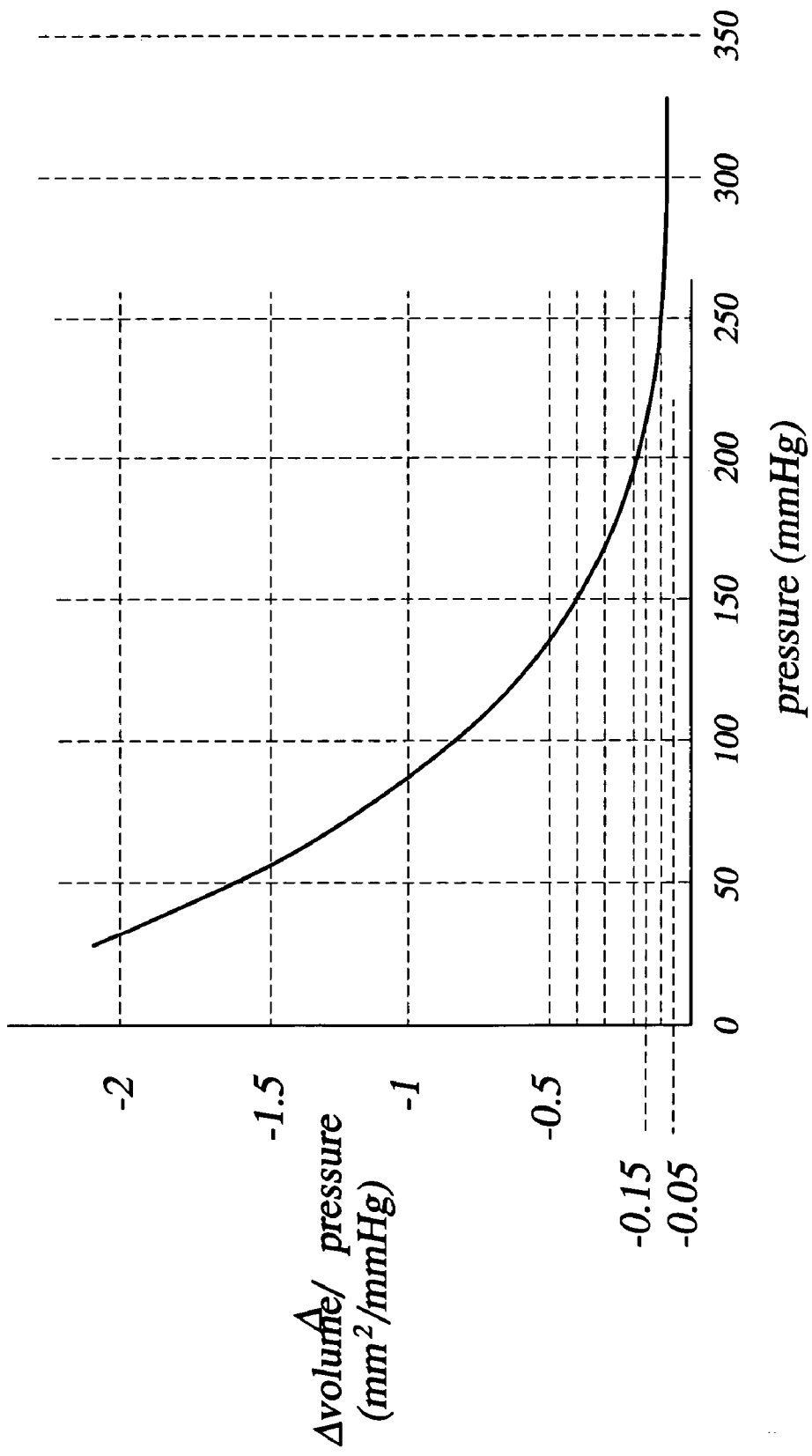
FIG. 50 illustrates the relationship between the slope of the curve in FIG. 49 and the actual pressure in the bladder.

FIG. 50 illustrates the relationship between the slope of the curve in FIG. 49 and the actual pressure in the bladder. The slope of the curve in FIG. 49 is charted as a function of the actual pressure in bladder. As indicated by the graph, the slope of the curve $\Delta p/\Delta v$ approaches zero when pressure approaches 300 mmHg in the bladder. This is the value expected for humans; in animal studies the slope approaches zero at about 300 mmHg. The controller for the system can operate to limit motor operation by ending a compression when the value or slope of this curve approaches a preset value (close to zero). Currently, the preset value is experimentally determined to be in the range of 0.05 to 0.15 mm²/mmHg². This value will be reached at different pressures for each patient, and at different pressures during the course of treatment of a single patient. It often is reached when pressure is well below 300 mmHg in the air bladder. In regards to both the slope of the curve v(p) of FIG. 49 (that is, the change in volume as a function of the change in pressure) and the slope or value of the curve $\Delta v/\Delta p(p)$ in FIG. 50 (that is, the ratio of an incremental change in volume to the incremental change in pressure in the bladder as a function of pressure in the bladder; the incremental change may also be referred to as the derivative of the functions of volume and pressure versus time), the optimum value for all patients falls within a narrow range as compared to the actual pressure required for adequate compression.

Operation of the system in response to the dual parameters of pressure and volume, and factoring in the rate of change of these parameters provides an unforeseen advantage to the operation of the system. The optimum change in volume, considered alone, or the optimum change in pressure, considered alone, may vary within a substantial range from patient to patient. This requires that volume and pressure changes must be excessive for some patients to ensure that they are sufficient for all patients (even considering the great advantage of using torque feedback and torque limits, which optimizes the amount of force applied while minimizing the draw on the battery). However, it appears from empirical studies that $\Delta v/\Delta \Delta p(p)$ curve varies only slightly from patient to patient. This allows control of the system within narrow ranges of $\Delta v/\Delta p$, and minimizes the waste of battery power required when the system is operated in response to less uniform parameters. Thus, operation in response to reaching the threshold illustrated in FIG. 49 is desirable since it applies to all patients with little variation.

Operation in response to reaching the threshold illustrated in FIG. 50 is desirable for the same reason, and also eliminates reliance on the actual values of the parameters. In this manner the controller is programmed to operate the motor to tighten the belt about the chest of the patient until the signal corresponding to pressure in the bladder indicates that optimal resuscitative compression of the patient's chest has been achieved. The optimal resuscitative compression in this case is expressed as the degree of compression that achieves a first ratio of change in volume over change in pressure in the range of −0.05 to −0.5, or achieves a second ratio of this first ratio over the actual pressure in the bladder in the range of −0.05 to −0.15. While this method has been discussed in terms of volume of the chest, the volume is approximated as a product of the belt length, and belt length may by used instead of chest volume in the computations. It should be noted that the actual length of the belt at any point need not be known, as the computations described above consider the change in belt length.

Figure 51:
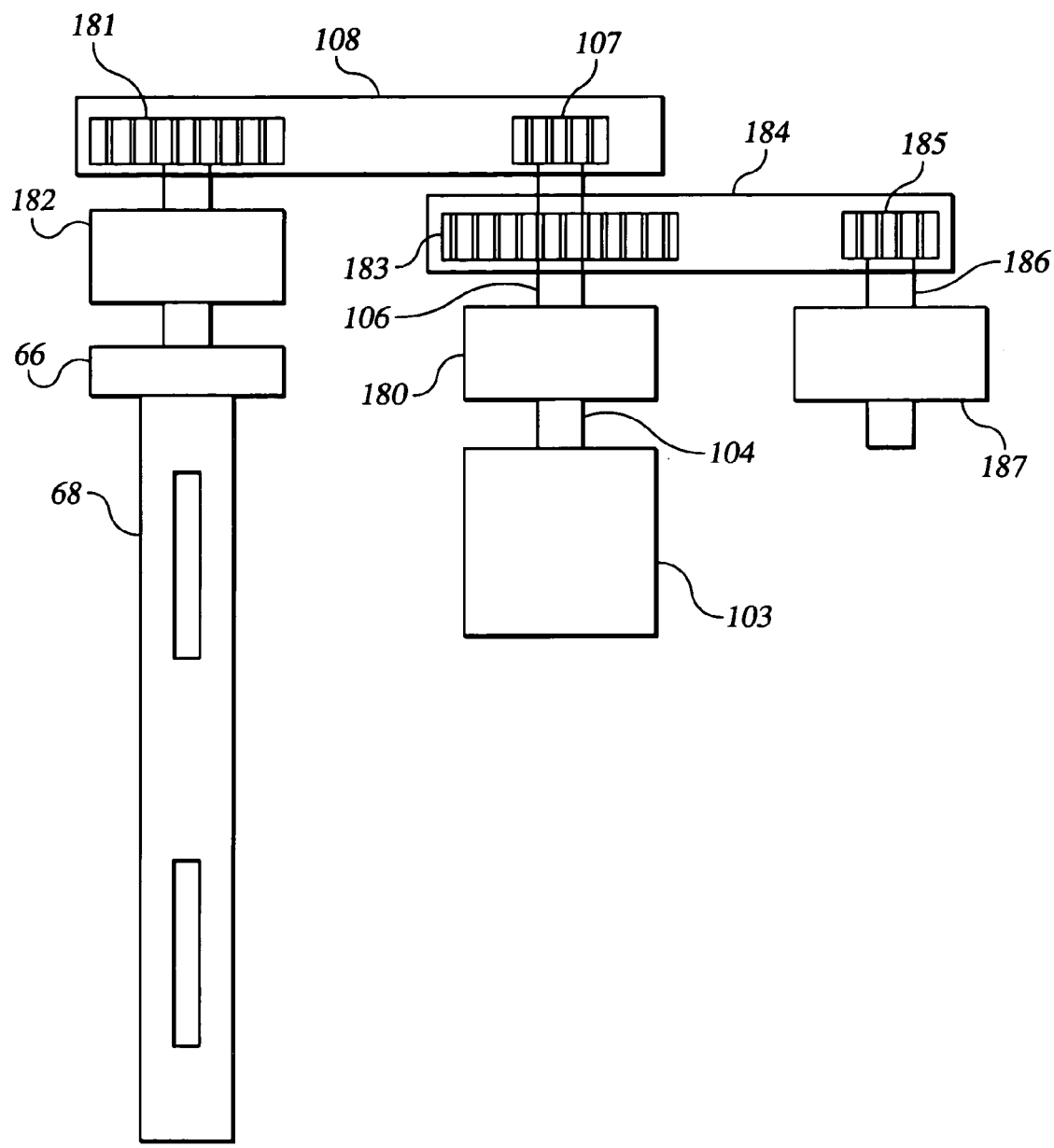
FIGS. 51 and 52 illustrate additional embodiments of the motor and drive train used to drive the drive spool.
Figure 52:
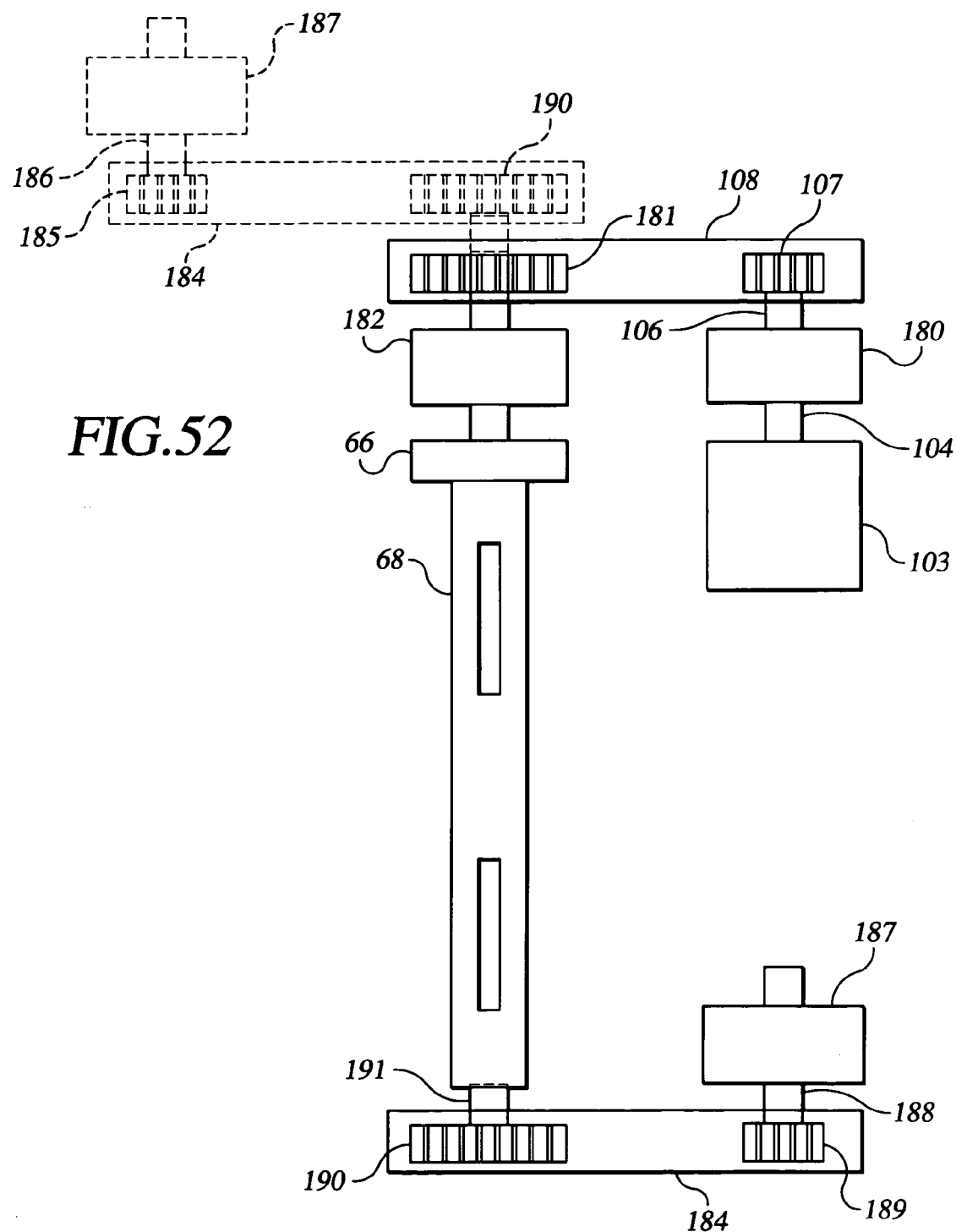

FIGS. 51 and 52 illustrate additional embodiments of the motor and drive train used to drive the drive spool. In these embodiments, a clutch need not be used, and the brake is located off-line relative to the drive train, and is connected to the drive train through a take-off. The motor 103 drives the motor shaft 104, gearbox output rotor 106 and sprocketed output wheel 107 through the gearbox 180. The output wheel 107 drives chain 108 which in turn rotates the drive sprocket wheel 181 and spool drive wheel 66. The drive spool 68 is operably connected to the drive wheel with the receiving rod which fits into a socket in the drive wheel. Interposed between the drive sprocket and the drive wheel is a torque sensor 182 which senses actual torque on the drive spool and transmits a corresponding signal to the controller. Interposed between the gearbox and the output wheel 107 is an additional sprocket wheel 183, which is connected via brake chain 184 to brake sprocket wheel 185 mounted on brake shaft 186 to the brake 187. The brake is an electromechanical brake operable by the controller. The various sprocket wheels are chosen in sizes to effect desired gear reduction and gearing changes. The motor used in our preferred embodiment rotates at about 15,000 rpm. The gearbox reduces the rotation to about 2,100 rpm (a 7:1 reduction), and the sprockets 107 and 181 are sized to effect a 2:1 reduction, so that the spool rotates at about 1,000 rpm. The braking sprockets 183 and 185 sized to effect a 1:2 reduction, so that the brake shaft 186 rotates at about 4,200 rpm. In other embodiments, the motor rotates at about 10,000 rpm; the gearbox reduces the rotation to about 1,000 rpm (a 10:1 reduction), and the sprockets 107 and 181 are sized to effect a 3:1 reduction, so that the spool rotates at about 333 rpm; the braking sprockets 18i and 185 sized to effect a 1:3 reduction, so that the brake shaft 186 rotates at about 3,000 rpm.

FIG. 52 shows another arrangement for installation of an off-line brake. As in FIG. 51, the motor 103 drives the motor shaft 104, gearbox output rotor 106, and sprocketed output wheel 107 through the gearbox 180. The output wheel 107 drives chain 108 which in turn rotates the drive sprocket 181 and spool drive wheel 66. The drive spool 68 is operably connected to the drive wheel. In this embodiment, the brake 187 is connected to the drive spool 68 via spool mounted brake shaft 186 and brake sprocket 185 mounted on this brake shaft. The brake chain 184 and brake sprocket 190 connects the brake to the drive spool. As indicated in phantom, the brake can be connected to the drive spool at either end of the drive spool, with the brake connected to brake shaft 186, extending from the drive sprocket 181 and brake sprocket 189. This enables connection of both the drive and the brake on the motor box side of the drive spool, retaining the potential for a modular system in which the drive spool (and the remainder of the compression belt cartridge) can easily be removed from the drive wheel and remainder of the motor box. The brake is connected through a take-off on the drive spool in FIG. 52, whereas it is connected to the drive train through a take-off on the gearbox output shaft in FIG. 51. By connecting the brake to a take-off, rather than in line as illustrated in FIG. 25, for example, the gearing of the brake may be adjusted, thereby reducing the torque requirements on the brake, and allowing use of a smaller and lighter brake, and allowing much faster braking than an in-line brake. Also, any after braking motion is reduced in effect at the spool by the various gearing changes, thus serving to limit belt overrun after the system operates the brake.

Belt overrun, which we use to refer to the condition in which the belt continues to tighten after the controller has operated to end a compression, wastes battery power and exerts more force on the patient than is desired. Also, slight delays or lag in the apparent bladder pressure (force applied to the body) causes overshoot in the system operation, so that even if system response were instantaneous, pressure in excess of the predetermined thresholds might be applied during routine operation. To limit these problems, the control system may be programmed to test the device and calibrate the system setpoints with the desired thresholds. This is illustrated in FIG. 53, which illustrates the actual and setpoint pressures for a series of compressions performed by the system for calibration purposes.

Figure 53:
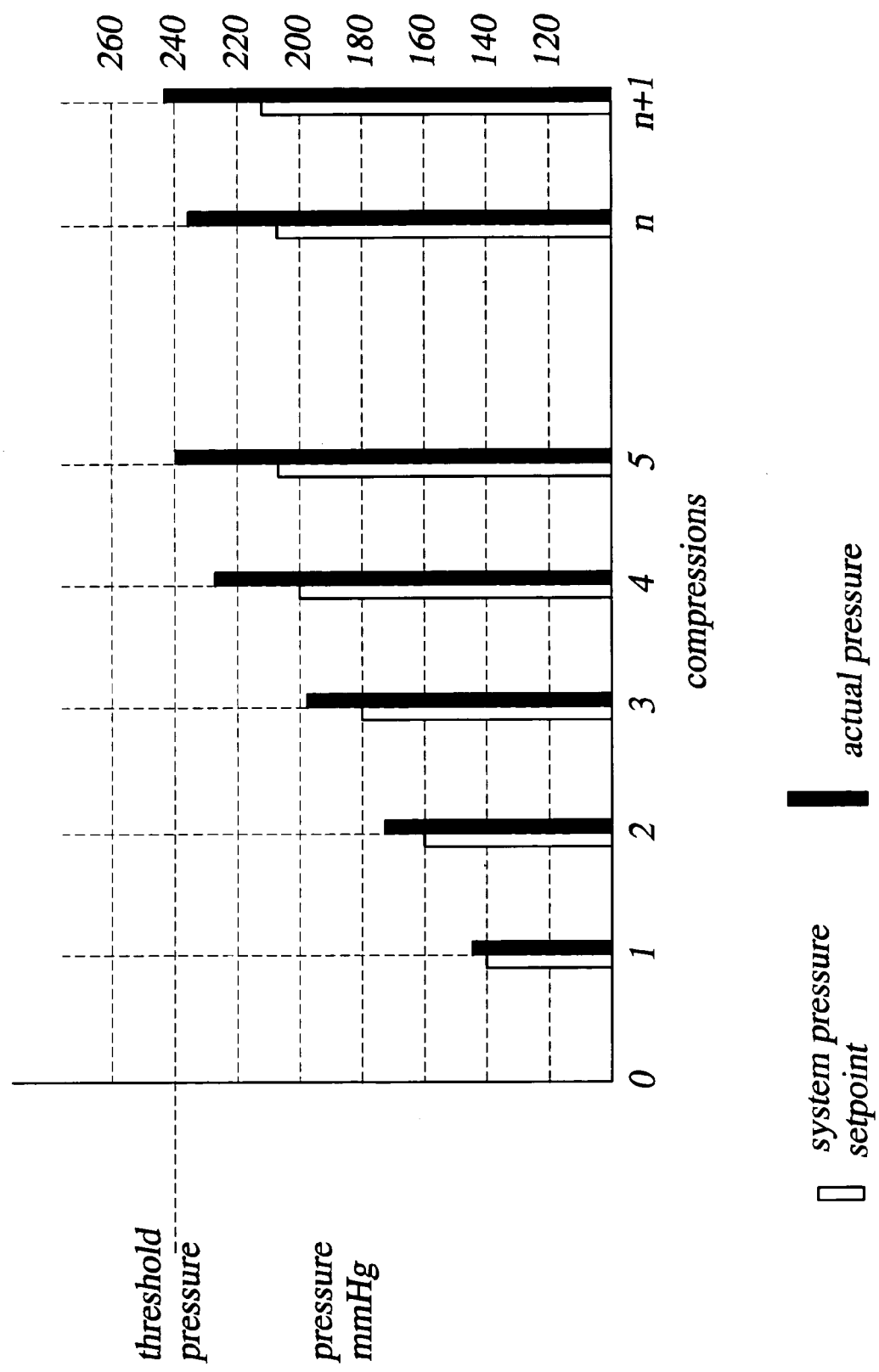
FIG. 53 is a graph of the actual and setpoint pressures for a series of compressions performed by the system for calibration purposes.

As shown in FIG. 53, in compression 1, the system selects a relatively low set-point, for example 140 mmHg in the bladder. By the time the system senses 140 mmHg in the bladder and stops compression, bladder pressure overshoots the setpoint substantially. The control system compares this actual pressure to its predetermined threshold of desired pressure on the patient of, for example, 240 mmHg, and determines that the overshoot is insufficient to meet the threshold, so the setpoint of 140 mmHg is insufficient to use as a setpoint. In the next compression, the control system selects a slightly higher setpoint of 160 mmHg, compresses to that setpoint, and observes the overshoot in the actual pressure reach about 200 mmHg, and determines that the overshoot is insufficient to meet the threshold, so the setpoint of 140 mmHg is insufficient to use as a setpoint. The control system continues testing in this manner until it observes, in a compression such as compression 5 in the chart, that a set-point of 220 mmHg leads to an overshoot to the desired threshold of 240 mmHg, and then selects 220 mmHg as a setpoint to be used by the system to achieve the desired threshold of 240 mmHg in subsequent compressions.

During the course of CPR, the overshoot may vary for numerous reasons, including changing elasticity of the patient's chest, temperature of the bladder, etc. The system continues to compare the actual pressure with the setpoint pressure, and adjusts accordingly. For example, in compression n in the chart, the actual pressure does not reach the threshold of 240 mmHg, so the system raises the setpoint slightly in compression n+1 and thereafter. Conversely, if the system observes that the actual pressure exceeds the threshold, the setpoint is lowered until actual pressure registers at the threshold. In this manner, the battery used to power the system is not consumed by the application of wasted pressure on the patient, but is not wasted by conservative and unproductive application of force below the threshold.

Many embodiments of CPR devices and control methods have been described above. While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for compressing the chest of a patient, said device comprising:
   a platform upon which a patient can rest;
   a belt operably connected to the platform and adapted to extend at least partially, around the chest of the patient, said belt further adapted for anterior-posterior compression of the patient;
   a motor operatively connected to the belt, wherein the motor is capable of driving the belt with sufficient force such that the belt can compresses the chest of the patient with an anteriorposterior compression;
   a drive spool operatively attached to the motor and to the belt;
   a spindle operably connected to the platform;
   wherein the belt is disposed around the patient and then around the spindle disposing the spindle between the belt and the patient; and
   a bladder disposed between the belt and the patient's sternum, said bladder being filled with a pressure transmitting medium.

2. A device for compressing the chest of a patient, said device comprising:
   a platform upon which a patient can rest;
   a belt operably connected to the platform and adapted to extend at least partially around the chest of the patient, said belt further adapted for anterior-posterior compression of the patient;
   a motor operatively connected to the belt, wherein the motor is capable of driving the belt with sufficient force such that the belt can compresses the chest of the patient;
   a drive spool operatively connected to the motor and the belt;
   a first spindle operably connected to the platform and disposed to the right of the patient, a second spindle operably connected to the platform and disposed to the left of the patient, and a third spindle operatively connected to the platform and disposed beneath the patient;
   wherein the belt is disposed around the first spindle, around the patient, around the second spindle, and around the third spindle; and
   a bladder disposed between the belt and the patient said bladder being filled with a pressure transmitting medium.

3. The device of claim 2 wherein the distance between the first spindle and the second spindle is in the range of about 12 inches to about 20 inches.

4. The device of claim 2 wherein the first spindle and the second spindle are disposed such that the device, when used on the patient, will perform anterior-posterior compressions on the patient.

5. The device of claim 2 wherein the first spindle and the second spindle are disposed posterior of the spine of the patient when the patient is placed on the device.

6. The device of claim 2 wherein the first spindle and the second spindle are disposed laterally of the spine and are disposed posterior of the scapula of the patient when the patient is placed on the device.

7. The device of claim 2 wherein the first spindle is disposed about in the area of the left axilla of the patient and the second spindle is disposed about in the area of the right axilla of the patient when the patient is placed on the device.

* * * * *